(12) United States Patent
Chorghade et al.

(10) Patent No.: US 10,265,692 B2
(45) Date of Patent: Apr. 23, 2019

(54) EX VIVO METHODS FOR PREDICTING AND CONFIRMING IN VIVO METABOLISM OF PHARMACEUTICALLY ACTIVE COMPOUNDS

(71) Applicant: Empiriko Corporation, Newton, MA (US)

(72) Inventors: Mukund Chorghade, Somerset, NJ (US); Chiara Chapman, Boston, MA (US)

(73) Assignee: Empiriko Corporation, Newton, MA (US)

( * ) Notice: Subject to any disclaimer, the term of this patent is extended or adjusted under 35 U.S.C. 154(b) by 0 days.

(21) Appl. No.: 15/101,088

(22) PCT Filed: Dec. 9, 2014

(86) PCT No.: PCT/US2014/069370
§ 371 (c)(1),
(2) Date: Jun. 2, 2016

(87) PCT Pub. No.: WO2015/089089
PCT Pub. Date: Jun. 18, 2015

(65) Prior Publication Data
US 2016/0303553 A1    Oct. 20, 2016

Related U.S. Application Data

(60) Provisional application No. 61/913,711, filed on Dec. 9, 2013.

(51) Int. Cl.
*B01J 31/18* (2006.01)
*G01N 33/15* (2006.01)
(Continued)

(52) U.S. Cl.
CPC ......... *B01J 31/2295* (2013.01); *A61K 31/194* (2013.01); *A61K 31/196* (2013.01);
(Continued)

(58) Field of Classification Search
CPC .......................... B01J 31/2295; A61K 31/194
(Continued)

(56) References Cited

U.S. PATENT DOCUMENTS

| 5,760,216 A | 6/1998 | Chorghade et al. |
| 6,370,478 B1 | 4/2002 | Stoughton et al. |

(Continued)

FOREIGN PATENT DOCUMENTS

| WO | 2013/086183 | 6/2013 |
| WO | 2013/123513 | 8/2013 |

OTHER PUBLICATIONS

International Search Report and Written Opinion dated Mar. 4, 2015 in International Application No. PCT/US14/69370, 17 pgs.
(Continued)

*Primary Examiner* — Brian J. Sines
(74) *Attorney, Agent, or Firm* — Fish & Richardson P.C.

(57) ABSTRACT

Methods and compositions for the catalytic oxidation of pharmaceutically active compounds, and more particularly to ex vivo methods for predicting in vivo metabolism of pharmaceutically active compounds, including predicting in vivo interaction between two or more pharmaceutically active compounds.

32 Claims, 21 Drawing Sheets

(51) Int. Cl.
| | |
|---|---|
| A61K 31/196 | (2006.01) |
| B01J 31/22 | (2006.01) |
| C07D 487/22 | (2006.01) |
| A61K 31/194 | (2006.01) |
| A61K 31/341 | (2006.01) |
| A61K 31/366 | (2006.01) |
| A61K 31/40 | (2006.01) |
| A61K 31/4015 | (2006.01) |
| A61K 31/4025 | (2006.01) |
| A61K 31/403 | (2006.01) |
| A61K 31/4355 | (2006.01) |
| A61K 31/4418 | (2006.01) |
| A61K 31/4422 | (2006.01) |
| A61K 31/4439 | (2006.01) |
| A61K 31/4995 | (2006.01) |
| A61K 31/505 | (2006.01) |
| A61K 31/506 | (2006.01) |
| A61K 31/5365 | (2006.01) |
| A61K 31/585 | (2006.01) |
| C07F 15/00 | (2006.01) |

(52) U.S. Cl.
CPC .......... *A61K 31/341* (2013.01); *A61K 31/366* (2013.01); *A61K 31/40* (2013.01); *A61K 31/403* (2013.01); *A61K 31/4015* (2013.01); *A61K 31/4025* (2013.01); *A61K 31/4355* (2013.01); *A61K 31/4418* (2013.01); *A61K 31/4422* (2013.01); *A61K 31/4439* (2013.01); *A61K 31/4995* (2013.01); *A61K 31/505* (2013.01); *A61K 31/506* (2013.01); *A61K 31/5365* (2013.01); *A61K 31/585* (2013.01); *B01J 31/18* (2013.01); *C07D 487/22* (2013.01); *C07F 15/0053* (2013.01); *G01N 33/15* (2013.01); *B01J 2231/70* (2013.01); *B01J 2531/821* (2013.01); *B01J 2531/842* (2013.01)

(58) Field of Classification Search
USPC .......................................................... 436/80
See application file for complete search history.

(56) References Cited

U.S. PATENT DOCUMENTS

2015/0038688 A1* 2/2015 Chorghade .............. C07C 37/00
534/588
2015/0274755 A1* 10/2015 Krska ..................... C07C 17/10
506/12

OTHER PUBLICATIONS

Chorghade et al. "Metalloporphyrins as Chemical Mimics of Cytochrome P-450 Systems", Bioorganic & Medicinal Chemistry Letters, 1994, vol. 4, pp. 2867-2890.
Chinese Office Action in Application No. 201480075205.4, dated Nov. 1, 2017, 35 pages (with English translation).

* cited by examiner

EX VIVO METHODS FOR PREDICTING AND CONFIRMING IN VIVO METABOLISM OF PHARMACEUTICALLY ACTIVE COMPOUNDS

CROSS-REFERENCE TO RELATED APPLICATIONS

This application is a 371 application of International Application No. PCT/US2014/069370, filed Dec. 9, 2014, which claims the benefit of U.S. Provisional Application No. 61/913,711, filed Dec. 9, 2013, the disclosures of which are incorporated herein by reference in their entireties.

TECHNICAL FIELD

This invention relates to methods and compositions for the catalytic oxidation of pharmaceutically active compounds, and more particularly to ex vivo methods for predicting in vivo metabolism of pharmaceutically active compounds, including predicting in vivo interaction between two or more pharmaceutically active compounds.

BACKGROUND

Today's pharmaceutical industry faces tremendous financial and competitive pressures to discover and select promising drug candidates more quickly and cost-effectively. Metabolism profiling is a widely used means of identifying toxicity and potential side effects, and selecting the best drug candidates for further study. According to some estimates, 90% of drug metabolites are implicated in adverse drug reactions, and metabolic processes of drugs are always the subject of intense scrutiny in pharmaceutical companies. However, the present-day process of studying metabolites involves animal studies, is labor-intensive and produces results that are chemically inconclusive. For numerous reasons, animal studies are sub-optimal for metabolite profiling. For example, animal studies entail animal sacrifice, often involve liver slice preparations as well as primary cultures of slow reacting hepatocytes and microsomes (e.g., S9 subfractions) that vary in potency, and the resulting metabolites are difficult to predict, confirm and quantify. Several alternate methods have also been explored with varying success, including using cultured cell lines (e.g., HepG2 or Huh7), nuclear receptor assays, cell lines stably or transiently expressing appropriate transcription factors and reporter genes, isolated perfused liver cells, plasma membrane vesicles, expressed hepatic proteins (e.g., one or more recombinant cytochrome P450 enzymes, transporters or receptors), and similar biological systems. These have met with limited success and the methods have not ameliorated the problems seen with biological systems.

Clearly, in vitro and ex vivo metabolism profiling are areas where breakthrough technology can be used to overcome current shortcomings.

SUMMARY

At least in part, the present invention is based on the discovery that synthetic biomimetic catalysts (e.g., sterically hindered and electronically activated metallotetraphenylporphyrins, metallophthalocyanines and metallosalen complexes) are useful tools for ex vivo prediction of in vivo drug metabolism and in vivo drug-to-drug interaction.

In one aspect, this disclosure provides ex vivo methods for predicting an in vivo interaction between two or more pharmaceutically active compounds, the method comprising contacting a first pharmaceutically active compound with an oxidizing agent and a catalyst selected from the group consisting of sterically hindered and electronically activated metallotetraphenylporphyrins, metallophthalocyanines and metallosalen complexes in an aqueous solution under conditions suitable for the formation of oxidative metabolites, and identifying the oxidative metabolites formed, to produce a compound metabolite profile, contacting, in combination, the first pharmaceutically active compound and at least one other pharmaceutically active compound with an oxidizing agent and a catalyst selected from the group consisting of sterically hindered and electronically activated metallotetraphenylporphyrins, metallophthalocyanines and metallosalen complexes in an aqueous solution under conditions suitable for the formation of oxidative metabolites, and identifying the oxidative metabolites formed, to produce a combination metabolite profile, comparing the compound metabolite profile with the combination metabolite profile, and predicting, establishing and validating in-vitro/in-vivo correlation between an in vivo interaction between the pharmaceutically active compounds based on the presence of a difference between the compound metabolite profile as compared with the combination metabolite profile.

In one or more embodiments, the catalyst is a sterically hindered and electronically activated metallotetraphenylporphyrin of formula 1:

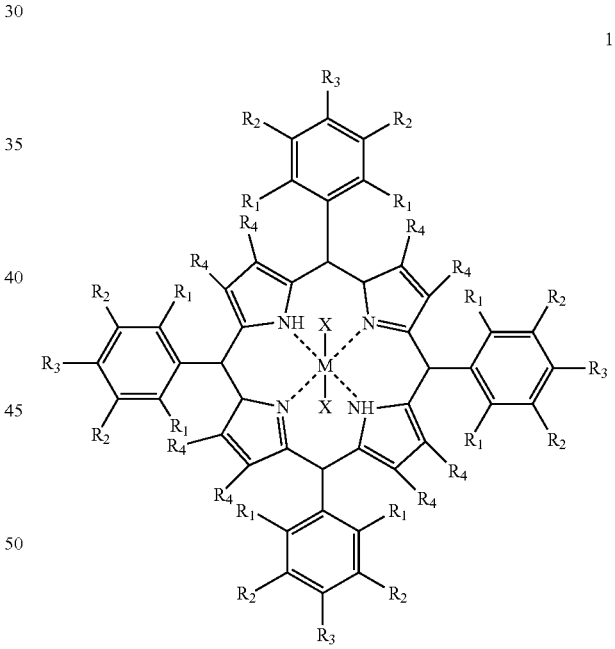

wherein $R_1$ is selected from the group consisting of Cl, Br, $CH_3$, $SO_3^-$, CN, $[N(R')_3]^+$, COOR', —OCONR'$_2$, —OMOM, CON—R', CONR'$_2$, CH=NR', $SO_2NR'_2$, $SO_2R$, CF and $NO_2$;

$R_2$ is selected from the group consisting of H, Cl, Br, $CH_3$, $SO_3^-$, CN, $[N(R')_3]^+$, COOR', —OCONR'$_2$, —OMOM, CON—R', CONR'$_2$, CH=NR', $SO_2NR'_2$, $SO_2R$, CF and $NO_2$;

$R_3$ is selected from the group consisting of H, Cl, Br, $CH_3$, $SO_3^-$, CN, $[N(R')_3]^+$, COOR', —OCONR'$_2$, —OMOM, CON—R', CONR'$_2$, CH=NR', $SO_2NR'_2$, $SO_2R$, CF and $NO_2$;

$R_4$ is selected from the group consisting of H, Cl, Br, $CH_3$, $SO_3^-$, CN, $[N(R')_3]^+$, COOR', —OCONR'$_2$, —OMOM, CON—R', CONR'$_2$, CH=NR', $SO_2NR'_2$, $SO_2R$, CF and $NO_2$;

R' is H or a C1-C6 alkyl;

M is a transition metal, such as Fe, Zn, Co, Ni, Cu, Mn, Rh, Mg, Ru, Pt, and Pd; and optionally wherein one or more axial ligands X selected from the group consisting of halogens (F, Cl, Br), OH, OCl, CO, $[N(R')_3]^+$, and substituted or unsubstituted nitrogen- or sulfur-containing amino acid derivatives selected from the group consisting of imidazole, alkyl-substituted imidazoles, mercapto-substituted imidazoles, trifluormethyl-substituted imidazoles, pyridine, alkyl-substituted pyridines, mercapto-substituted pyridines, trifluoromethyl-substituted pyridines, pyrimidine, alkyl-substituted pyrimidines, mercapto substituted pyrimidines, trifluoromethyl-substituted pyrimidines, isoquinoline, alkyl-substituted isoquinolines, mercapto-substituted isoquinolines, trifluoromethyl-substituted isoquinolines, acridine, alkyl-substituted acridines, mercapto-substituted acridine, trifluoromethyl-substituted acridine, quinoline, benzoquinolines, alkyl-substituted quinolines, mercapto-substituted quinolines, trifluormethyl-substituted quinolines, benzylmercaptan and thiophenol and/or a counter ion is included to maintain charge neutrality.

In one embodiment, $R_1$ is Cl, $R_2$ is H, $R_3$ is H, $R_4$ is Cl, M is Fe and X is Cl.

In another embodiment $R_1$ is Cl, $R_2$ is H, $R_3$ is H, $R_4$ is Br, M is Fe and X is Cl.

In yet another embodiment, $R_1$ is Cl, $R_2$ is H and one $R_2$ is $SO_3Na$, $R_3$ is H, $R_4$ is Br, M is Fe and X is Cl.

In another embodiment, $R_1$ is Cl, $R_2$ is H, $R_3$ is H, $R_{a4}$ is Cl or Br, M is Ru and X is Cl.

In another aspect, the catalyst is a metallophthalocyanine compound of formula 2:

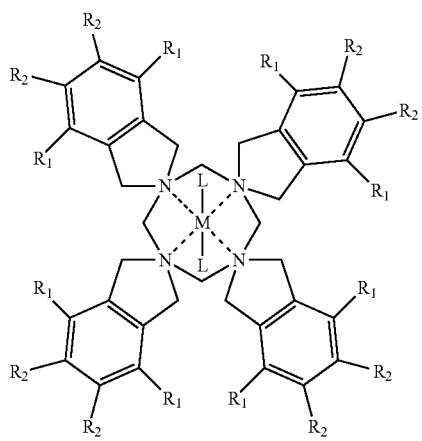

2 wherein $R_1$ is selected from the group consisting of Cl, Br, $CH_3$, $SO_3^-$, CN, $[N(R')_3]^+$, COOR', —OCONR'$_2$, —OMOM, CON—R', CONR'$_2$, CH=NR', $SO_2NR'_2$, $SO_2R$, CF and $NO_2$;

$R_2$ is selected from the group consisting of H, Cl, Br, $CH_3$, $SO_3^-$, CN, $[N(R')_3]^+$, COOR', —OCONR'$_2$, —OMOM, CON—R', CONR', CH=NR', $SO_2NR'_2$, $SO_2R$, CF and $NO_2$;

$R_3$ is selected from the group consisting of H, Cl, Br, $CH_3$, $SO_3^-$, CN, $[N(R')_3]^+$, COOR', —OCONR'$_2$, —OMOM, CON—R', CONR'$_2$, CH=NR', $SO_2NR'_2$, $SO_2R$, CF and $NO_2$;

$R_4$ is selected from the group consisting of H, Cl, Br, $CH_3$, $SO_3^-$, CN, $[N(R')_3]^+$, COOR', —OCONR'$_2$, —OMOM, CON—R', CONR'$_2$, CH=NR', $SO_2NR'_2$, $SO_2R$, CF and $NO_2$;

wherein R' is H or a C1-C6 alkyl,

M is a transition metal, such as Fe, Zn, Co, Ni, Cu, Mn. Rh, Mg, Ru, Pt, and Pd;

and optionally wherein one or more axial ligands L selected from the group consisting of halogens (F, Cl, Br), OH, OCl, CO, $[N(R')_3]^+$, and substituted or unsubstituted pyrimidine or imidazole bases, is included and/or a counter ion is included to maintain charge neutrality.

In one embodiment, the $R_1$ and $R_2$ are Cl.

In another embodiment, $R_1$ and $R_2$ are H.

In another aspect, the catalyst is a metallosalen complex compound of formula 3:

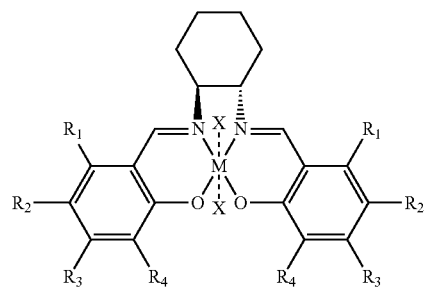

3 wherein $R^1$ is selected from the group consisting of Cl, Br, $CH_3$, $SO_3^-$, CN, $[N(R')_3]^+$, COOR', —OCONR'$_2$, —OMOM, CON—R', CONR'$_2$, CH=NR', $SO_2NR'_2$, $SO_2R$, CF and $NO_2$, $R^2$ is the same or different and is selected from the group consisting of H, Cl, Br, $CH_3$, —$C(CH_3)_3$, $SO_3^-$, CN, $[N(R')_3]^+$, COOR', —OCONR'$_2$, —OMOM, CON—R', CONR'$_2$, CH=NR', $SO_2NR'_2$, $SO_2R$, CF and $NO_2$, $R_3$ is selected from the group consisting of H, Cl, Br, $CH_3$, $SO_3^-$, CN, $[N(R')_3]^+$, COOR', —OCONR'$_2$, —OMOM, CON—R', CONR'$_2$, CH=NR', $SO_2NR'_2$, $SO_2R$, CF and $NO_2$;

$R_4$ is selected from the group consisting of H, Cl, Br, $CH_3$, $SO_3^-$, CN, $[N(R')_3]^+$, COOR', —OCONR'$_2$, —OMOM, CON—R', CONR'$_2$, CH=NR', $SO_2NR'_2$, $SO_2R$, CF and $NO_2$;

wherein R' is H or a C1-C6 alkyl,

M is a transition metal, such as Fe, Zn, Co, Ni, Cu, Mn, Rh, Mg, Ru, Pt, and Pd, and optionally wherein one or more axial ligands X selected from the group consisting of halogens (F, Cl, Br), OH, OCl, CO, $[N(R')_3]^+$, and substituted or unsubstituted pyrimidine or imidazole bases, is included and/or a counter ion is included to maintain charge neutrality.

In one aspect, the catalyst (e.g., sterically hindered and electronically activated metallotetraphenylporphyrins, metallophthalocyanines or metallosalen complexes) is immobilized onto a polymeric resin solid support. In some embodiments, the polymeric resin solid support comprises a polymer selected from the group consisting of polyethylene, polystyrene, polycarbonate, polypropylene, polyamide, phenolic resin, epoxy resin, polycarbodiimide resin, polyvinyl chloride, polyvinylidene fluoride, polyethylene fluoride, polyimide, acrylic resin or the like.

In one aspect, the catalysts (e.g., sterically hindered and electronically activated metallotetraphenylporphyrins, metallophthalocyanines or metallosalen complexes) is encapsulated in a polymer matrix, such as, for example, a polystyrene matrix.

In one aspect, the oxidizing agent is selected from the group consisting of organic and inorganic peroxides, oxygen donor molecules, peracids, periodates, hypochlorites, ozone, potassium hydrogen persulfate, 2,6-dichloropyridine-N-oxide and molecular oxygen.

In one aspect, the methods provided herein further comprise contacting the solution containing the first pharmaceutically active compound with a co-catalyst comprising a nitrogen- or sulfur-containing amino acid derivative, such as aromatic nitrogen rings and free thiols, to act as electron donors coordinating to the center metal in situ. In some embodiments, the co-catalyst comprising a nitrogen- or sulfur-containing amino acid derivative is selected from the group consisting of imidazole, alkyl-substituted imidazoles, mercapto-substituted imidazoles, trifluoromethyl-substituted imidazoles, pyridine, alkyl-substituted pyridines, mercapto-substituted pyridines, trifluoromethyl-substituted pyridines, pyrimidine, alkyl-substituted pyrimidines, mercapto-substituted pyrimidines, trifluoromethyl-substituted pyrimidines, isoquinoline, alkyl-substituted isoquinolines, mercapto-substituted isoquinolines, trifluoromethyl-substituted isoquinolines, acridine, alkyl-substituted acridines, mercapto-substituted acridine, trifluoromethyl-substituted acridine, quinoline, benzoquinolines, alkyl-substituted quinolines, mercapto-substituted quinolines, trifluoromethyl-substituted quinolines, benzylmercaptan and thiophenol.

In one aspect, the methods provided herein further comprise contacting the solution containing the first pharmaceutically active compound with a phase-transfer agent when the solution is a biphasic mixture. In some embodiments, the phase transfer agent is selected from the group consisting of quaternary-ammonium salts, tetra-n-butylammonium bromide (TBAB), tricaprylylmethylammonium chloride, hexadecyltributylphosphonium bromide, tetrabutylphosphonium bromide, 18-crown-6, aliquat 336, benzyltriethylammonium chloride (TEBA), methyltrioctylammonium hydrogen sulfate (TOMAHS), cetylpyridinium chloride, tetrahexylammonium bromide, N-benzylcinchonidinium bromide, and N-benzylcinchoninium bromide.

In another aspect, the pharmaceutically active compound (e.g., the first pharmaceutically active compound or the at least one other pharmaceutically active compound) are selected from the group consisting of acetylcholine receptor stimulants and antagonists; adrenoreceptor-activated compounds, adrenoreceptor-blocking compounds, antihypertensive agents, vasodilators, cardiac glycosides, diuretics, histamine, serotonin, antihistamines, antihypertensives, polypeptides, antibiotics, anti-infective agents, antimicrobials, anticonvulsants, antidiabetic agents, antiemetics, steroids, sedatives, antiepileptic compounds, anesthetics, skeletal muscle relaxants, antidepressants, antipsychotics, analgesics, lithium, anticoagulants, cholinesterase inhibitors, procoagulants, HMG-CoA reductase inhibitors (statins), nonsteroidal anti-inflammatory agents, antimitotic agents, protease inhibitors, thyroid and antithyroid compounds, hypnotics, fibrinolytic agents, recombinant proteins, peptides, adrenocorticosteroids, gonadal hormones and inhibitors, immunomodulators, immunosuppressives, erectile dysfunction therapeutics, penicillins, cephalosporins, chloramphenicol, tetracyclines, polymyxins, antimyobacterial compounds, sulfonamides, narcotics, trimethoprim, antifungal agents, antiviral agents, non-steroidal anti-inflammatory compounds, anticancer agents, vaccines, antiprotozoal compounds, antacids, antiarythmics, and antihelminthic compounds. In an exemplary embodiment, the pharmaceutically active compound is selected from the lovastatin, amlodipine, atorvastatin, rosuvastatin, simvastatin, fluvastatin, pitavastatin, pravastatin, pioglitazone, lidocaine, odipipam, aminopyrine, metformin, glimepiride, spironolactone, nifedipine, furosemide, saxagliptin, and drugs for X syndrome application.

The disclosure also provides methods for preparing oxidative metabolites for a pharmaceutically active compound, the method comprising contacting a solution comprising one or more pharmaceutically active compounds with one or more catalysts immobilized on a substrate for a period sufficient for catalytic oxidation of the one or more pharmaceutically active compounds by the catalyst, separating the solution from the one or more catalysts immobilized on a substrate, and identifying the oxidative metabolites for the one or more pharmaceutically active compounds, wherein the one or more catalysts are selected from the group consisting of sterically hindered and electronically activated metallotetraphenylporphyrins, metallophthalocyanines and metallosalen complexes.

The disclosure also provides a sample processing device for the systemic preparation of oxidative products of a pharmaceutically active compound in a sample solution, the device comprising at least one inlet that receives flow of a sample solution and directs the sample solution flow to flow chamber, a flow chamber comprising one or more catalysts immobilized on a substrate, and at least one outlet that receives the sample solution flow from the flow chamber, wherein the one or more catalysts immobilized on the substrate are selected from the group consisting of sterically hindered and electronically activated metallotetraphenylporphyrins, metallophthalocyanines and metallosalen complexes.

The term "pharmaceutically active compound," "active pharmaceutical ingredient (API)," "pharmaceutically active agent," "active agent," "bioactive agent," "pharmaceutical," "drug compound," and "drug" mean any chemical compound that is useful in the prevention, diagnosis, treatment, or cure of disease for the relief of pain or to control or improve the underlying cause or symptoms associated with any physiological or pathological disorder in humans or animals. The term "pharmaceutically active compound," "pharmaceutically active agent," "active pharmaceutical ingredient (API)," "active agent," "bioactive agent," "pharmaceutical," "drug compound," and "drug" may be used interchangeably to refer to an agent or substance that has measurable specified or selected physiologic activity when administered to a subject in a significant or effective amount. As used herein, these terms are intended to be consistent with the Food and Drug Administration's definition of an API, including "any substance or mixture of substances intended to be used in the manufacture of a drug product and that, when used in the production of a drug, becomes an active ingredient in the drug product. Such substances are intended to furnish pharmacological activity or other direct effect in the diagnosis, cure, mitigation, treatment or prevention of disease or to affect the structure and function of the body." APIs include substances manufactured by processes such as (1) chemical synthesis; (2) fermentation; (3) recombinant DNA or other biotechnology methods; (4) isolation/recovery from natural sources; or (5) any combination of these processes. The term "drug" is expressly encompassed by the present definition as many drugs and prodrugs are known to have specific physiologic activities. These terms of art are well known in the pharmaceutical and medicinal arts. The terms "drug", and "prodrug" as used herein all include pharmaceutically acceptable salts, solvates, hydrates, polymorphs, co-crystals, enantiomers, diastereoisomers, tautomers, regioisomers, racemates and the like of the compounds.

As used herein, the term "drug product" is intended to mean a finished dosage form, for example, a tablet, capsule or solution that contains an active pharmaceutical ingredient, generally, but not necessarily, in association with inactive ingredients.

As used herein "CYP" is intended to mean Cytochrome P, and more specifically Cytochrome P450, the major phase I metabolizing enzyme of the liver constituting of many different isoenzymes, such as CYP1A1, CYP1A2, CYP1B1, CYP2A6/2A7/2A13, CYP2B6, CYP2C8, CYP2C9, CYP2C19, CYP2D6, CYP2E1, CYP3A4, CYP3A5, CYP3A7 and CYP7A1.

The section headings used herein are for organizational purposes only and are not to be construed as limiting the described subject matter in any way. When definitions of terms in incorporated references appear to differ from the definitions provided in the present teachings, the definition provided in the present teachings shall control. It will be appreciated that there is an implied "about" prior to metrics such as temperatures, concentrations, and times discussed in the present teachings, such that slight and insubstantial deviations are within the scope of the present teachings herein. In this application, the use of the singular includes the plural unless specifically stated otherwise. Also, the use of "comprise," "comprises," "comprising," "contain," "contains," "containing," "include," "includes," and "including" are not intended to be limiting. It is to be understood that both the foregoing general description and the following detailed description are exemplary and explanatory only and are not restrictive of the invention. The articles "a" and "an" are used herein to refer to one or to more than one (i.e., to at least one) of the grammatical object of the article. By way of example, "an element" means one element or more than one element.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DETAILED DESCRIPTION

Figure 1:
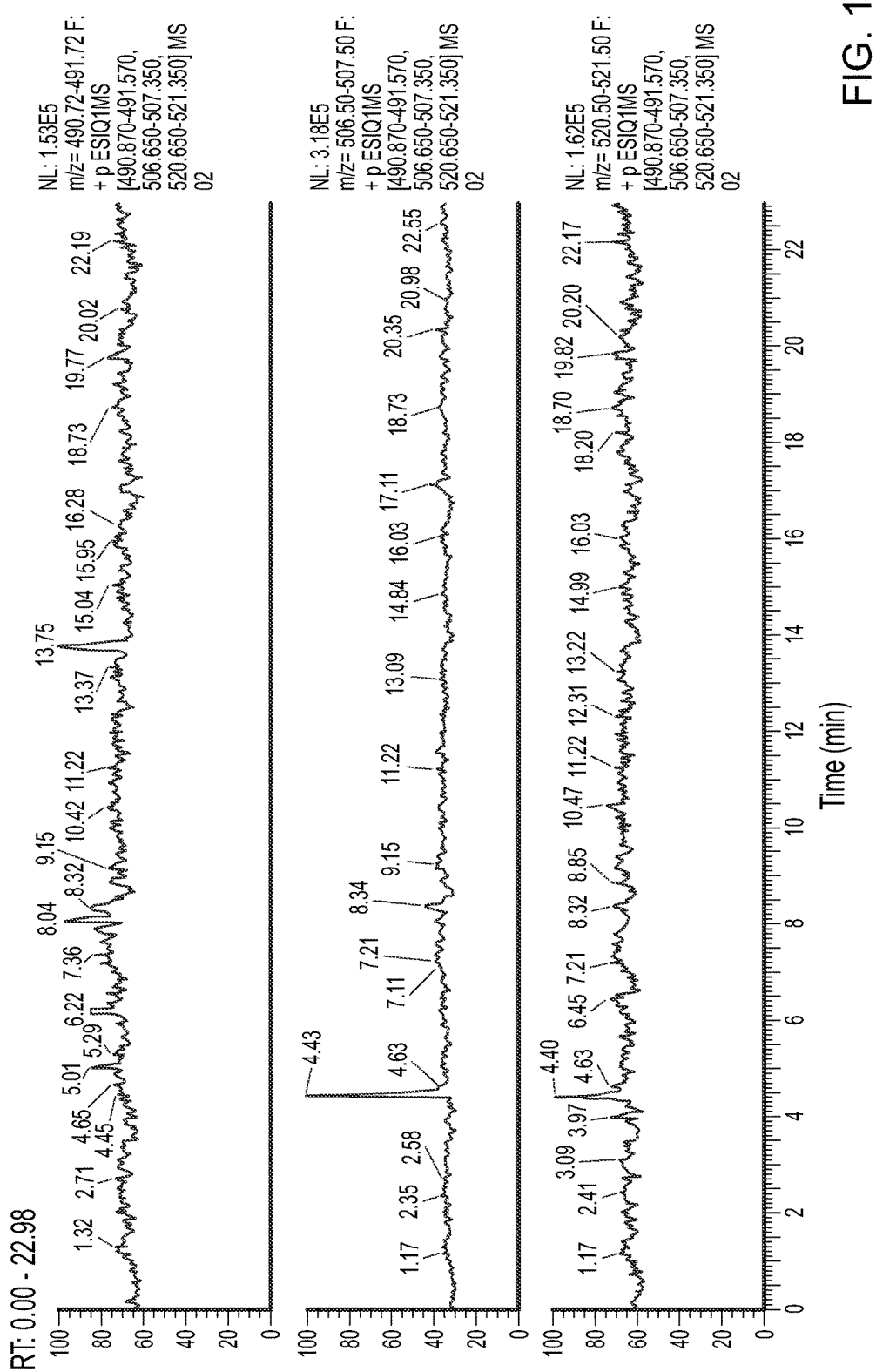
FIG. 1 is a representative MS-SIM chromatogram demonstrating representative glimepiride metabolites produced following microwave reaction in the presence of Octabromo tetrakis(2,6-dichlorophenyl)porphyrin Fe(III)Cl.

In humans and other animals most drugs (e.g., pharmaceutically active compounds) are metabolized in the liver. Metabolizing enzymes transform these drugs into metabolites. The primary purpose for drug metabolism is to detoxify, inactivate, solubilize and eliminate these drugs. As a result, the amount of the drug in its original form that reaches systemic circulation is reduced due to this first-pass metabolism. Of these, the cytochrome P450-dependent monooxygenases provide the primary catalysis in most biological oxidations (cf., Cytochrome P-450: Structure, Mechanism and Biochemistry, P. R. Ortiz de Montellano, ed., Plenum Press, N.Y., 1986).

The metabolic process that a drug compound undergoes in the body may contribute to the safety and efficacy of the compound and to the presence or absence of toxicity or undesirable biological activity of its metabolites. These factors are major contributors to the success or failure of a pharmaceutical compound; many metabolites are implicated in toxicity and adverse reactions. Pharmacologists attempt to identify and isolate such compounds as early as possible in the drug development process, but are constrained by lack of predictive knowledge about the structure of the chemical products. They have traditionally tried to obtain sufficient quantities of these metabolites in order to conduct further toxicological and pharmacological studies on them.

Several problems are associated with the use of biological systems in studying drug metabolism: both animal and in vitro, metabolic studies produce very small amounts of metabolites, thus making identification of these metabolites difficult. These metabolites must be isolated from aqueous systems to be identified. Metabolism studies with large numbers of animals are notoriously expensive to conduct, and even when identified, the metabolites may not be easily or efficiently synthesized for further testing. Consequently, scientists obtain a limited picture of metabolites, unidentified side effects and unpredictable patient outcomes.

Drug metabolites are formed in the liver by oxidative mechanisms catalyzed primarily by heme and cytochrome containing enzymes. Most biological oxidations involve primary catalysis provided by the cytochrome P450 monooxygenase enzymes. All heme proteins that are activated by hydrogen peroxide, including catalases, peroxidases and ligninases function via a two electron oxidation of the ferric resting state to an oxoferryl porphyrin cation radical.

While this oxidation state has yet to be conclusively characterized for the cytochromes P450, most of their reactions and those of the biomimetic analogs can be accounted for by oxygen transfer from Compound I (heme high-valent active intermediate) to a variety of substrates to give characteristic reactions such as hydroxylation, epoxidation and heteroatom oxidation. Other products resulting from hydroxyl and hydroperoxyl radicals have also been detected. It is important to note that such products cannot be readily prepared by classical modes of oxidation Investigators initially studied model systems of the biological oxidations in which synthetic metalloporphyrins were utilized as mimics of the cytochrome P450-dependent monooxygenase enzymes. A limited number of reviews of the literature were published, including those by Xie and Dolphin ("Biological Oxidations with Heme Proteins," in Metalloporphyrins Catalyzed Oxidations, F. Montanari and L. Casella, eds., Kluwer Academic Publishers, The Netherlands, 1994, pp 269-306); and Montanari et al. (Rev. Heteroat. Chem., 6:94-141 (1992)).

The first catalysts studied were found to be unstable, due to formation of peroxy dimers, and catalytic turnovers and reaction rates were uniformly low. Improvements in molecular stability, with concomitant increases in the turnover of catalytic reactions, have been obtained with the introduction of additional atoms into the synthetic azamacrocycle molecules. The work of Dolphin and others has shown that addition of halogen atoms onto the aryl groups and the β-pyrrolic positions of meso-tetraarylporphyrins makes intermediate oxo-porphyrin complexes more electron deficient and more sterically protected and provides for more effective oxidation catalysis (see, for example, Xie and Dolphin, op. cit.) as it increases the turnover of catalytic reactions by decreasing the rate of porphyrin destruction.

Some uses of synthetic metalloporphyrins for the study of the oxidative metabolism of drugs have been reported. Carrier et al. (Bull. Soc. Chim. Fr., 130:405-416 (1993)), who studied lidocaine oxidation with various cytochrome P450 model systems and produced thereby some of the known primary metabolites of lidocaine, have suggested that reaction conditions and the metalloporphyrins themselves might be varied to give varying yields of oxidation products, or at times, different products entirely. In contrast, by applying methods described herein, the remaining known metabolites, as well as some additional oxidation products which are being considered as possible additional metabolites, have been produced. This is particularly useful for metabolites that are transiently produced in aqueous systems and are inherently unstable to isolation and storage.

In a multiple-drug scenario, physicians lack the information they need to accurately evaluate drug-to-drug interactions for effectiveness and safety issues. Too often, physicians rely on trial and error when prescribing new drugs for their patients, wasting precious time and money. Currently, there are no ex vivo methods available for clinicians to dynamically predict or measure a patient's response (drug-to-drug interactions, dosing levels and regimens) to a spectrum of drugs, and incorporate the results into more effective patient treatment.

The present inventors have developed new in vitro methods of metabolism profiling that mimic the in vivo metabolism of pharmaceutically active compounds, with catalysts serving as a "chemosynthetic liver" for predicting metabolism patterns, pathways and profiles. In developing the chemosynthetic liver, the inventors sought to solve a number of the problems surrounding metabolism studies in drug discovery. Traditional methodologies involve significant animal sacrifice, and lack the speed, stability, scalability and predictability needed to design new chemical entities (NCEs) with confidence. Present-day metabolism profiling is slow and inconclusive, making it nearly impossible to predict the success or failure of a drug candidate. The typical screening process takes days, and sometimes weeks. Animal derived samples (liver slices, hepatocytes and microsomes) vary in potency, react slowly and produce insufficient amounts of metabolites for ongoing pharmacological testing. Conventional chromatography and spectroscopy on aqueous systems (used in current-day metabolite profiling) do not cleanly detect, characterize and quantify water-soluble metabolites, providing an incomplete profile. Undetected metabolites can lead to adverse side effects, prolonged trial and error during patient treatment, and increased potential for late-stage drug withdrawals. Animal-based models fail to accurately mimic biological receptor interactions and human reactions to drugs, leaving significant margin for error.

Thus, the present methods can be used to systematically and efficiently predict, produce and identify metabolites of drug candidates, e.g., to allow the determination to be made as to whether these metabolites possess any unacceptable toxicity profiles and/or have either desirable or undesirable biological activity as early as possible in the expensive drug development process.

Also provided herein are methods for producing and identifying oxidative products of an exploratory pharmaceutical active compound (e.g., a drug candidate) from which the metabolites of the compound could be identified before animal or biological studies are done.

In addition, provided herein are methods for producing large quantities of oxidation products of drug candidates, which products may have been identified as metabolites by biological testing, in quantities sufficient to allow for toxicological and further biological tests for key characteristics such as interference with liver enzymes (toxicologic, pathologic, histopathalogic, genotoxic), membrane permeability, water solubility, chemical stability thereon, at an early stage in the discovery process.

The methods described herein also to provide acceptable ways of reducing the amount of animal testing required in the development of a drug candidate.

Accordingly, the methods described herein establish a new ex vivo paradigm for metabolism profiling, enabling scientists and clinicians to reduce the attrition rate of new chemical entities (NCEs) by conducting early metabolism studies, generating quantitative measures of toxicity before administration of a new drug to a patient, and predicting the effectiveness of the new drug within the context of a patient's existing therapies. These chemistry-based methods provide physicians the information they need to confidently predict the safety of a new drug within the context of a patient's existing drug regimen. The catalysts and methods disclosed herein serve as models of oxidative catalysts in biological systems.

Identifying and Predicting Metabolites Ex Vivo

The methods disclosed herein can be used to provide information to predict the safety of a pharmaceutically active compound prior to administration to a patient or as part of a patient's existing drug regimen. Pharmaceutically active compounds are reacted with an oxidizing agent and a catalyst selected from the group consisting of sterically hindered and electronically activated metallotetraphenylporphyrins, metallophthalocyanines and metallosalen complexes in an aqueous solution under conditions suitable for the formation of oxidative metabolites, to produce, detect and identify metabolites of the pharmaceutically active compounds, e.g., to allow the determination to be made as to whether these metabolites possess any unacceptable toxicity profiles and/or have either desirable or undesirable biological activity as early as possible in the expensive drug development process. The methods disclosed herein can be may further include the isolation and identification of metabolites. In those instances in which a metabolite has been detected, a sufficient amount of that molecule is isolated to evaluate its specificity, selectivity, efficacy, and, possibly its toxicity, in addition to a determination of its chemical structure.

Predicting Drug-Drug Interactions

Physicians face an uphill battle when prescribing new drugs to patients who are already taking a plethora of other medications. In this multiple-drug scenario, physicians lack the information they need to accurately evaluate drug-to-drug interactions, effectiveness and safety issues. Too often, physicians rely on trial and error when prescribing random new drugs for their patients, wasting precious resources of time, money and peace of mind.

The methods disclosed herein can be used to provide information to predict the safety of a new drug within the context of combination therapy, e.g., in a patient's existing drug regimen. Combinations of drugs (e.g., pharmaceutically active compounds) are reacted with an oxidizing agent and a catalyst selected from the group consisting of sterically hindered and electronically activated metallotetraphenylporphyrins, metallophthalocyanines and metallosalen complexes in an aqueous solution under conditions suitable for the formation of oxidative metabolites, to detect favorable or unfavorable interactions between drugs and metabolites in a patient's blood, serum or plasma. The metabolic patterns are compared with those of single drugs to determine enhancement, attenuation or suppression of metabolites, in order to assess the safety of a specific drug for the patient. The metabolic patterns can be further analyzed within the context of clinical history of the patient to assess drug-to-drug interactions and efficacy associated with adding a new drug to a patient's drug regimen. In the examples below, protocols for generating metabolites for clinical testing and profiling have been developed with exemplary catalysts. Initial experiments for generating and predicting metabolic profiling (ex vivo) of metformin have yielded encouraging preliminary results indicating that the present methods can be used with other drugs for clinical research and patient outcomes, e.g., for: (1) Evaluation of the inhibition/induction of the most common CYPs by observing whether the metabolism of the NCE is inhibited/induced by co-administration with known strong CYP inhibitors; (2) Evaluation of the interaction as a substrate of the most common CYPs by observing whether the NCE substantially changes the metabolism of sensitive substrates of known CYP enzymes; and (3) Evaluation of whether the NCE significantly affects the metabolic elimination of drugs already in the marketplace because it inhibits or induces a co-administered drug's metabolism CYO pathway.

Metabolite Production

The methods described herein can also be used for the preparation of oxidative products of a pharmaceutically active compound, comprising reacting the compound with a series of combinations of a member of a group of catalysts (e.g., sterically hindered and electronically activated metallotetraphenylporphyrins, metallophthalocyanines or metallosalen complexes), as defined below, with a member of a group of co-oxidizing reagents, as defined below, with a member of a group of co-catalysts, in the presence of a suitable solvent, such as, for example, methylene chloride, acetonitrile, acetonitrile/water, methanol/water, buffered aqueous solutions thereof, or the like, for a period of up to twenty-four (24) hours, at a temperature from 0° C. to reflux temperature of the solvent, or under microwave irradiation in a manner such that each sample of drug compound is reacted with a different combination of synthetic catalyst, co-oxidizing reagent and solvent, followed by separating and isolating each resulting oxidative product by gas, liquid/liquid, or solid/liquid chromatography, HPLC, or the like. The oxidative products can then be identified by NMR, $C^{13}$ NMR, MS, HRMS, IR, or UV spectroscopy. In some embodiments, these oxidative products can then be used as predictors of safety and efficacy of the drug candidate compound in studies with appropriate animal models. The actual metabolites can also be subjected (e.g., in larger quantities prepared by methods according to the processes described herein optimized to prepare these specific metabolites) to various biological tests in order to identify toxicity and/or other desirable or undesirable biological activity of these metabolites as early as possible in the very expensive drug development process.

Catalysts

Disclosed herein are methods for preparing oxidative metabolites of a pharmaceutically active compound that include contacting the pharmaceutically active compound with an oxidizing agent and one or more catalysts. The catalysts can be, e.g., metalloporphyrins, metallophthalocyanines, and/or metallosalen complexes, as described herein.

Metalloporphyrins

In some embodiments, the catalyst is a sterically hindered and electronically activated metallotetraphenylporphyrin of formula 1:

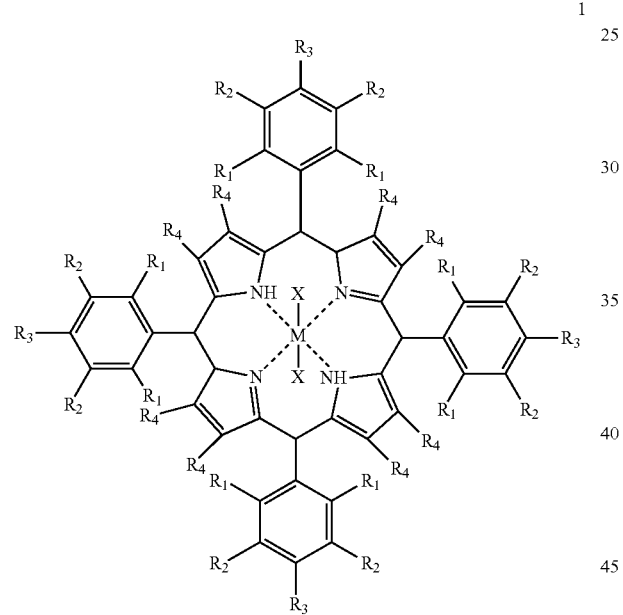

wherein $R_1$ is selected from the group consisting of Cl, Br, $CH_3$, $SO_3^-$, CN, $[N(R')_3]^+$, COOR', —OCONR'$_2$, —OMOM, CON—R', CONR'$_2$, CH=NR', $SO_2NR'_2$, $SO_2R$, CF and $NO_2$;

$R_2$ is selected from the group consisting of H, Cl, Br, $CH_3$, $SO_3^-$, CN, $[N(R')_3]^+$, COOR', —OCONR'$_2$, —OMOM, CON—R', CONR'$_2$, CH=NR', $SO_2NR'_2$, $SO_2R$, CF and $NO_2$;

$R_3$ is selected from the group consisting of H, Cl, Br, $CH_3$, $SO_3^-$, CN, $[N(R')_3]^+$, COOR', —OCONR'$_2$, —OMOM, CON—R', CONR'$_2$, CH=NR', $SO_2NR'_2$, $SO_2R$, CF and $NO_2$;

$R_4$ is selected from the group consisting of H, Cl, Br, $CH_3$, $SO_3^-$, CN, $[N(R')_3]^+$, COOR', —OCONR'$_2$, —OMOM, CON—R', CONR'$_2$, CH=NR', $SO_2NR'_2$, $SO_2R$, CF and $NO_2$;

R' is H or a C1-C6 alkyl;

M is a transition metal, such as Fe, Zn, Co, Ni, Cu, Mn, Rh, Mg, Ru, Pt, and Pd; and optionally wherein one or more axial ligands X selected from the group consisting of halogens (F, Cl, Br), OH, OCl, CO, $[N(R')_3]^+$, and substituted or unsubstituted pyrimidine or imidazole bases, is included and/or a counter ion is included to maintain charge neutrality.

In some embodiments, $R_1$ is Cl, $R_2$ is H, $R_3$ is H, $R_4$ is Cl, M is Fe and X is Cl.

In some embodiments. $R_1$ is Cl, $R_2$ is H, $R_3$ is H, $R_4$ is Br, M is Fe and X is Cl.

In some embodiments, $R_1$ is Cl, $R_2$ is H and one $R_2$ is $SO_3Na$, $R_3$ is H, $R_4$ is Br, M is Fe and X is Cl.

In some embodiments, $R_1$ is Cl, $R_2$ is H, $R_3$ is H, $R_4$ is Cl or Br, M is Ru and X is Cl.

In some embodiments, the sterically hindered and electronically activated metallotetraphnylporphyrin is selected from the group consisting of

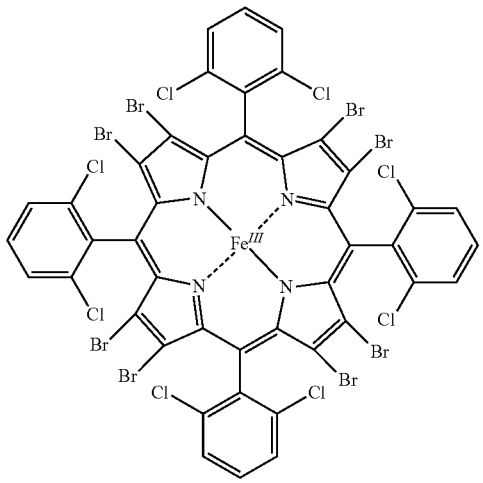

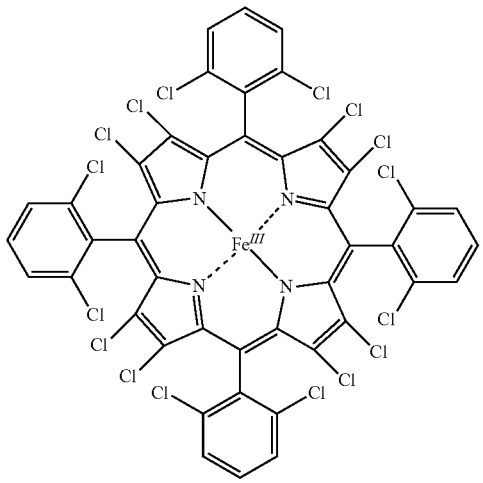

-continued

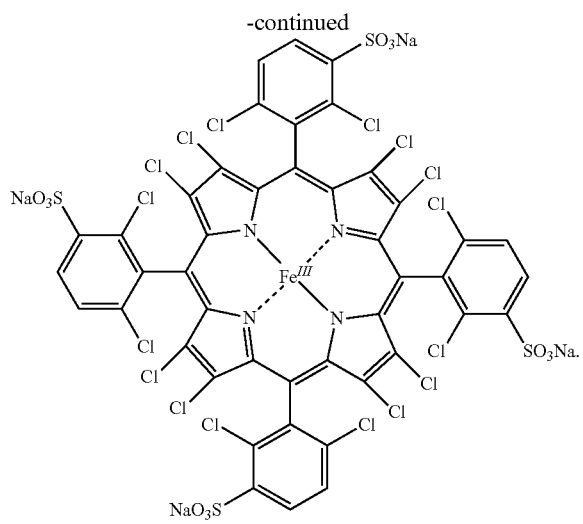

Exemplary synthetic metalloporphyrins for use herein are the compounds wherein M is iron or manganese, and are selected from the group comprising octachloro-octabromo Fe(III) porphyrin, octachloro-octabromo Mn(II) porphyrin, octachloro-octachloro Ru (III) porphyrin, octachloro-octabromo Ru (III) porphyrin, octachloro-octachloro Fe(III) porphyrin octachloro-octachloro Mn (II) porphyrin, octachloro-octabromo tetrasulfonato Fe(III) porphyrin, octachloro-octabromo tetrasulfonato Mn(II) porphyrin, octachloro-octachloro tetrasulfonato Fe(III) porphyrin, and octachloro-octachloro tetrasulfonato Mn(II) porphyrin.

In some embodiments of this process, the synthetic metalloporphyrins are selected from the group comprising octachloro-octabromo Fe(III) porphyrin, octachloro-octabromo Mn(II) porphyrin, octachloro-octachloro tetrasulfonato Fe(III) porphyrin, and octachloro-octachloro tetrasulfonato Mn(II) porphyrin; the co-oxidizing reagents are selected from the group comprising iodosobenzene, sodium hypochlorite, tert-butyl hydroperoxide, and potassium monopersulfate; and the solvents are those selected from the group comprising $CH_2Cl_2$, 20% $CH_3CN$ in $H_2O$, and buffered aqueous solutions.

The synthetic metalloporphyrins can be prepared by known methods (see the references cited in the Background, above) wherein a suitable zinc-containing metalloporphyrin, such as meso-tetrakis (2,6-dihalophenyl)-porphyrinato-zinc (II), wherein "halo" is chloro, bromo, fluoro, or indo, is reacted with one of several active halogenating agents, followed by removal and replacement of the zinc atom with the desired active metal ion. They can also be prepared by an improved method for the preparation of a porphyrin-ring halogenated synthetic metalloporphyrin, wherein the halogenating agent may be a free halogen, such as $Cl_2$ or $Br_2$, in a suitable polar solvent, such as methanol, ethanol, and the reaction may be performed at lower temperatures, thus resulting in enhanced yields of the desired product.

Such a synthetic metalloporphyrin can be prepared by reacting a suitable zinc-containing metalloporphyrin, such as meso-tetrakis(2,6-dichlorophenyl)-porphyrinato-zinc(II), for example, with a free halogen, such as $Cl_2$ or $Br_2$, in a suitable polar solvent, such as methanol, ethanol, or the like, at a temperature of from 0° C. to ambient, followed by removal and replacement of the zinc atom with the desired active metal ion.

Metallophthalocyanines

Also disclosed herein are methods for preparing oxidative metabolites of a pharmaceutically active compound that include contacting the pharmaceutically active compound with an oxidizing agent and a catalyst, wherein the catalyst is a metallophthalocyanine compound of formula 2:

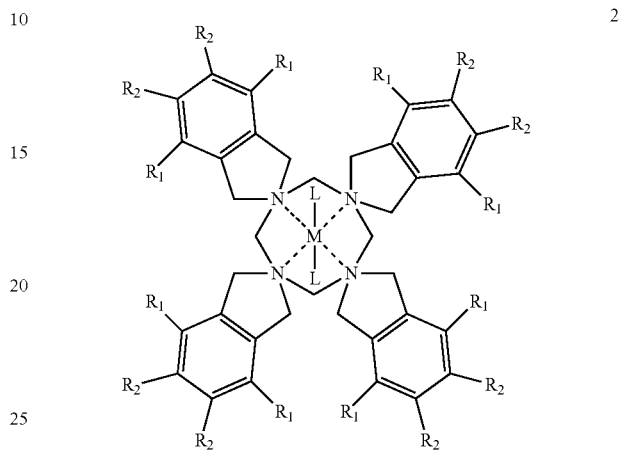

wherein $R_1$ is selected from the group consisting of Cl, Br, $CH_3$, $SO_3^-$, CN, $[N(R')_3]^+$, COOR', —OCONR'$_2$, —OMOM, CON—R', CONR'$_2$, CH=NR', $SO_2NR'_2$, $SO_2R$, CF and $NO_2$;

$R_2$ is selected from the group consisting of H, Cl, Br, $CH_3$, $SO_3^-$, CN, $[N(R')_3]^+$, COOR', —OCONR'$_2$, —OMOM, CON—R', CONR'$_2$, CH=NR', $SO_2NR'_2$, $SO_2R$, CF and $NO_2$;

$R_3$ is selected from the group consisting of H, Cl, Br, $CH_3$, $SO_3^-$, CN, $[N(R')_3]^+$, COOR', —OCONR'$_2$, —OMOM, CON—R', CONR'$_2$, CH=NR', $SO_2NR'_2$, $SO_2R$, CF and $NO_2$;

$R_4$ is selected from the group consisting of H, Cl, Br, $CH_3$, $SO_3^-$, CN, $[N(R')_3]^+$, COOR', —OCONR'$_2$, —OMOM, CON—R', CONR'$_2$, CH=NR', $SO_2NR'_2$, $SO_2R$, CF and $NO_2$;

wherein R' is H or a C1-C6 alkyl,

M is a transition metal, such as Fe, Zn, Co, Ni, Cu, Mn, Rh, Mg, Ru, Pt, and Pd; and optionally wherein one or more axial ligands L selected from the group consisting of halogens (F, Cl, Br), OH, OCl, CO, $[N(R')_3]^+$, and substituted or unsubstituted pyrimidine or imidazole bases, is included and/or a counter ion is included to maintain charge neutrality.

In some embodiments, the $R_1$ and $R_2$ are Cl.

In some embodiments, $R_1$ and $R_2$ are H.

Metallosalen Complexes

Also disclosed herein are methods for preparing oxidative metabolites of a pharmaceutically active compound that include contacting the pharmaceutically active compound with an oxidizing agent and a catalyst, wherein the catalyst is a modified Jacobson (salen) catalyst.

In some embodiments, the catalyst is a metallosalen complex compound of formula 3:

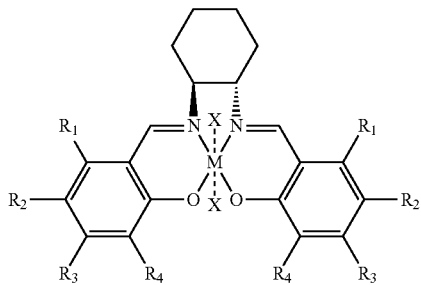

wherein $R^1$ is selected from the group consisting of Cl, Br, $CH_3$, $SO_3^-$, CN, $[N(R')_3]^+$, COOR', —OCONR'$_2$, —OMOM, CON—R', CONR'$_2$, CH=NR', $SO_2NR'_2$, $SO_2R$, CF and $NO_2$, $R^2$ is the same or different and is selected from the group consisting of H, Cl, Br, $CH_3$, —$C(CH_3)_3$, $SO_3^-$, CN, $[N(R')_3]^+$, COOR', —OCONR'$_2$, —OMOM, CON—R', CONR'$_2$, CH=NR', $SO_2NR'_2$, $SO_2R$, CF and $NO_2$, $R_3$ is selected from the group consisting of H, Cl, Br, $CH_3$, $SO_3^-$, CN, $[N(R')_3]^+$, COOR', —OCONR'$_2$, —OMOM, CON—R', CONR'$_2$, CH=NR', $SO_2NR'_2$, $SO_2R$, CF and $NO_2$;

$R_4$ is selected from the group consisting of H, Cl, Br, $CH_3$, $SO_3^-$, CN, $[N(R')_3]^+$, COOR', —OCONR'$_2$, —OMOM, CON—R', CONR'$_2$, CH=NR', $SO_2NR'_2$, $SO_2R$, CF and $NO_2$;

wherein R' is H or a C1-C6 alkyl,

M is a transition metal, such as Fe, Zn, Co, Ni, Cu, Mn, Rh, Mg, Ru, Pt, and Pd, and optionally wherein one or more axial ligands X selected from the group consisting of halogens (F, Cl, Br), OH, OCl, CO, $[N(R')_3]^+$, and substituted or unsubstituted pyrimidine or imidazole bases, is included and/or a counter ion is included to maintain charge neutrality.

In some embodiments, the metallosalen complex compound has the following structure:

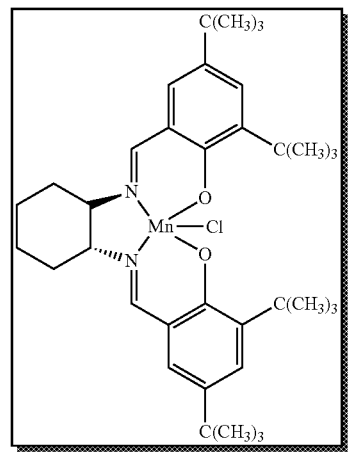

In some embodiments, the modified Jacobson (salen) catalyst can be prepared according to Scheme 1 or Scheme 2.

Scheme 1.
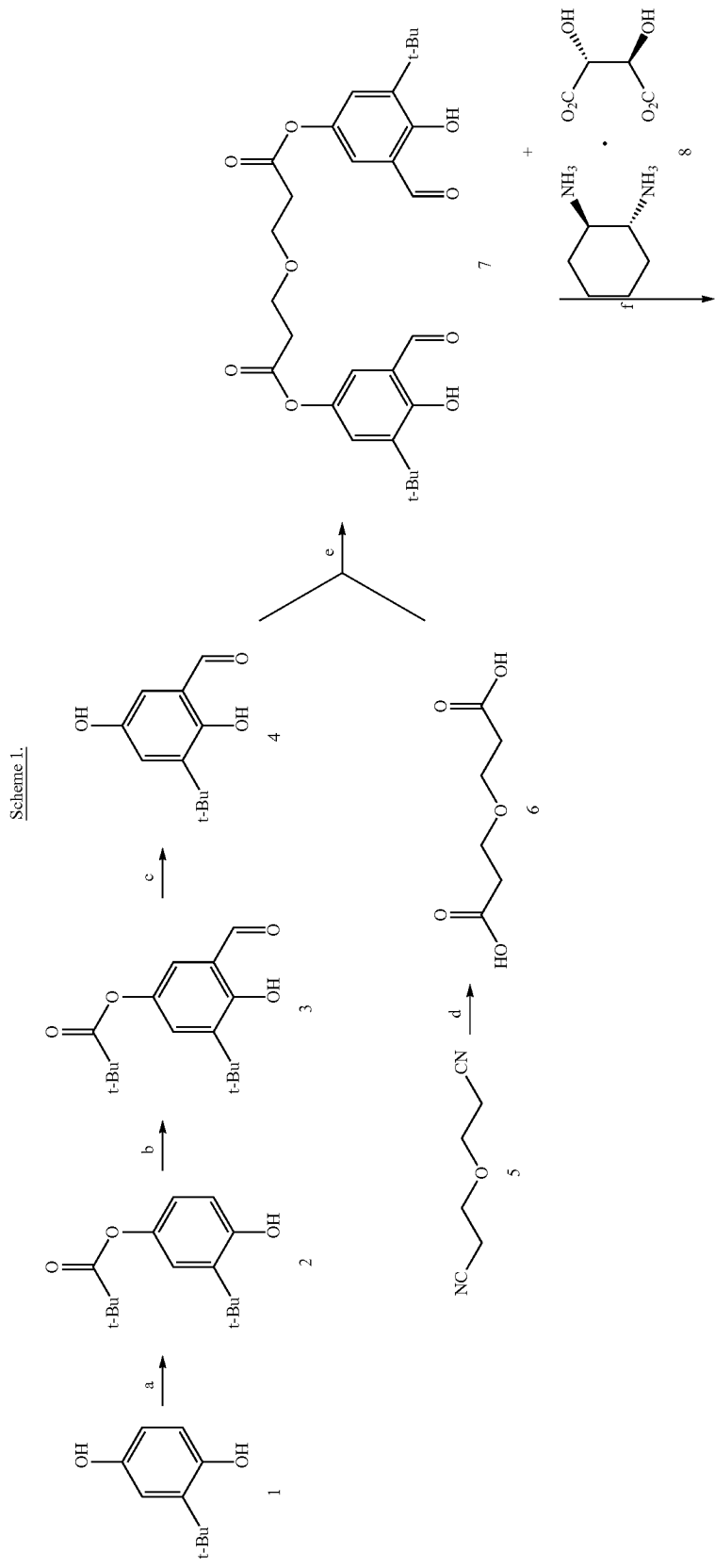

-continued
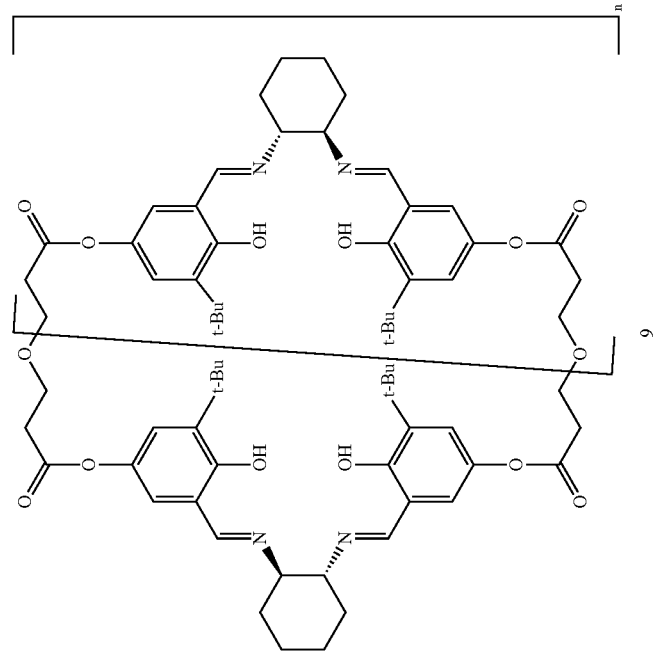
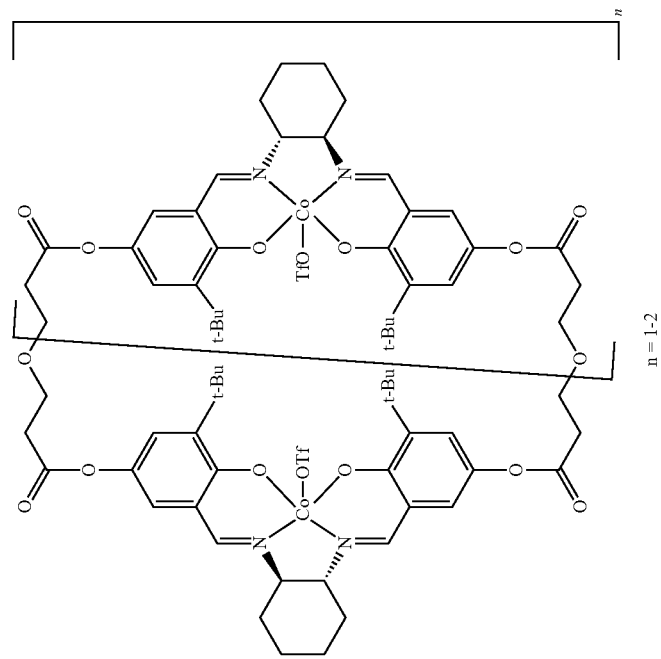
n = 1-2

Scheme 2

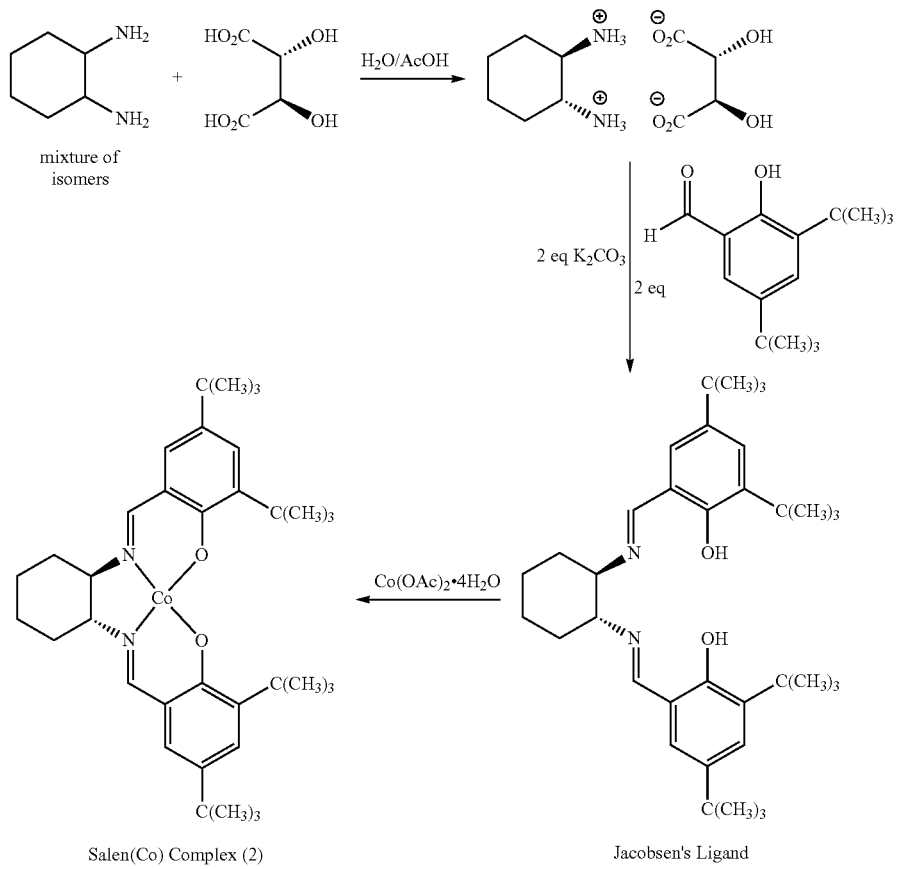

Co-Catalysts

Sulfur is known as a strong electron donor that is easily oxidized, therefore heme-enzymes that are bound to cysteine might not possess optimal characteristics for an oxidizing active site. In the mid-1980's the first X-ray structure of a cytochrome P450 enzyme was published, showing definitively for the first time that these enzymes are in fact bound by a cysteinate ligand (Mansuy, D. C. R. Chimie, 10, 392-413 (2007)). This evidence, proving that sulfur is indeed present at the active site for oxidation, has lead many researchers to investigate how this is accomplished.

In a February 2014 Nature article, Groves discusses recent data on enzymatic C—H bond activation and how heme-enzymes from the cytochrome P450 superfamily are able to accomplish the incredible feat of oxidizing these strong, inert bonds (Groves, J. T. Nature, 6, 89-91 (2014)).

Noted therein is a Science publication where Yosca et al. examined CYP158 and 119, members of the superfamily, in order to understand the Fe(IV)=O and Fe(IV)—OH states of the enzymes (Yosca, T. H., et al. Science, 342, 825-829 (2013)). It was found that the transformation of iron from being doubly-bound to oxygen to the protonated singly-bound species lengthened the iron-oxygen bond while shortening the iron-sulfur bond from cysteine. This is significant because the Fe(IV)OH species is formed when the C—H bond of the substrate is broken. The strength of the O—H bond formed then creates the thermodynamics for this hydrogen transfer step.

This phenomenon has been coined the 'push-pull' effect. The push of electrons from the sulfur of cysteine onto the iron-active site creates a greater pull for the oxygen on the opposite side; increasing basicity and promoting C—H bond cleavage (Id).

These findings suggest a use for a cysteine-like mimic (e.g., a co-catalyst) when creating an enzymatic oxidative model. The addition of nitrogen and thiolate amino acid derivatives as co-catalysts serves to further mimic in vivo conditions as mentioned above, where heme-enzymes such as cytochrome oxidase and horseradish peroxidase are bound to the protein matrix by the sulfur of cysteine and the neutral nitrogen of histidine.

Thus, in some aspects, the methods disclosed herein further comprise adding a co-catalyst to the reaction mixture containing the pharmaceutically active compound, oxidizing agent, and catalyst. Exemplary co-catalysts include nitrogen or sulfur containing amino acid derivatives with pKa values similar to that of the conjugate acid of cysteine (e.g. having pKa values ranging from 5.0 to 10.0, i.e., pKa values of about 5.0, 5.5, 6.0, 6.5, 7.0, 7.5, 8.0, 8.5, 9.0, 9.5 or about 10.0) containing relatively inert substituent's that also do not sterically hinder access to the basic site, such as aromatic nitrogen rings and free thiols. Exemplary co-catalysts for the reactions disclosed herein include, but are not limited to, imidazole, alkyl-substituted imidazoles, mercapto-substituted imidazoles, trifluoromethyl-substituted imidazoles, pyridine, alkyl-substituted pyridines, mercapto-substituted pyridines, trifluoromethyl-substituted pyridines, pyrimidine, alkyl-substituted pyrimidines, mercapto-substituted pyrimidines, trifluoromethyl-substituted pyrimidines, isoquinoline, alkyl-substituted isoquinolines, mercapto-substituted isoquinolines, trifluoromethyl-substituted isoquinolines, acridine, alkyl-substituted acridines, mercapto-substituted acridine, trifluoromethyl-substituted acridine, quinoline, benzoquinolines, alkyl-substituted quinolines, mercapto-substituted quinolines, trifluoromethyl-substituted quinolines, benzylmercaptan and thiophenol.

Oxidizing Agents

As used herein, the terms "oxidizing agent" and "co-oxidizing agent" are used interchangeably. In some embodiments, the methods described herein include the use of an oxidizing agent. Such an oxidizing agent serves as a source of oxygen radicals to generate the oxoferryl or oxometal cation. Exemplary oxidizing agents include organic and inorganic peroxides, oxygen donor molecules, peracids, hypochlorites, ozone, potassium hydrogen persulfate, 2,6-dichloropyridine-N-oxide and molecular oxygen. In some embodiments, the oxidizing agent is, for example, iodosobenzene, sodium hypochlorite, potassium monopersulfate, ozone, or a peroxide, such as hydrogen peroxide, m-chloroperbenzoic acid, cumene hydroperoxide or tert-butyl hydroperoxide. The oxidizing reagent is preferably added to the reaction mixture gradually, in small quantities, with a fresh charge of oxidant being added later, e.g., after a period of 1, 2, 3, 4, 5, or 6 hours.

The catalytic reactions disclosed herein can be carried out using any solvent known to those skilled in the art that does not interact unfavorably with the catalyst and/or the oxidizing agent. The solvent can be selected to favor solubility of the drug compound or the synthetic metalloporphyrin, or for ease of recovery and purification of the product. For ex vivo work, an exemplary solvent is plasma derived from blood, e.g., mammalian plasma, e.g., human plasma. Exemplary solvents include $CH_2Cl_2$; $CH_3CN$; 20% methanol in $H_2O$; 20% $CH_3CN$ in H2O; or aqueous solutions buffered to various pH levels, e.g., pH 3.0, 3.5, 4.0, 4.5, 5.0, 5.5, 6.0, 6.5, 7.0, 7.5, 8.0, 8.5, 9.0, 9.5, 10.0.

The combining and reacting of the pharmaceutical active compound, the catalyst, oxidizing agent and the solvents may be achieved either simultaneously or serially with or without appropriate automated means, including the use of robotic devices. A "kit" of catalyst and oxidizing agent is also provided herein, for use in the methods described herein.

The present methods can optionally include optimization of reaction conditions by to identify the appropriate combination of solvent, catalyst, oxidant and reaction conditions that produces the maximum number and/or amount of metabolites or of one or more desired metabolites. This logically leads to a subsequent scaled-up optimal process by which large amounts of one or more desired metabolites may be produced.

The process of the invention may be used in combination with an examination of the oxidative products produced thereby in toxicity tests, such as for example, acute, subchronic, or chronic studies involving clinical pathologic, histopathologic, mechanistic or genotoxicity protocols, or in other screens or protocols in use for determining biological activity, for identifying toxic or metabolically-active metabolites of a pharmaceutically active compound (e.g., a drug candidate).

Pharmaceutically Active Compounds

The pharmaceutically active compound may include any drug belonging to any therapeutic category including but not limited to acetylcholine receptor stimulants and antagonists; adrenoreceptor-activated compounds, adrenoreceptor-blocking compounds, antihypertensive agents, vasodilators, cardiac glycosides, diuretics, histamine, serotonin, antihistamines, antihypertensives, polypeptides, antibiotics, anti-infective agents, antimicrobials, anticonvulsants, antidiabetic agents, antiemetics, steroids, sedatives, antiepileptic compounds, anesthetics, skeletal muscle relaxants, antidepressants, antipsychotics, analgesics, lithium, anticoagulants, cholinesterase inhibitors, procoagulants, HMG-CoA reductase inhibitors (statins), nonsteroidal anti-inflammatory agents, antimitotic agents, protease inhibitors, thyroid and antithyroid compounds, hypnotics, fibrinolytic agents, recombinant proteins, peptides, adrenocorticosteroids, gonadal hormones and inhibitors, immunomodulators, immunosuppressives, erectile dysfunction therapeutics, penicillins, cephalosporins, chloramphenicol, tetracyclines, polymyxins, antimyobacterial compounds, sulfonamides, narcotics, trimethoprim, antifungal agents, antiviral agents, non-steroidal anti-inflammatory compounds, anticancer agents, vaccines, antiprotozoal compounds, antacids, antiarythmics, and antihelminthic compounds.

In one aspect, the one or more pharmaceutically active compound is selected from the lovastatin, amlodipine, atorvastatin, rosuvastatin, simvastatin, fluvastatin, pitavastatin, pravastatin, pioglitazone, lidocaine, odipipam, aminopyrine, metformin, glimepiride, spironolactone, nifedipine, furosemide, saxagliptin clarithromycin, erythromycin, fluconazole, itraconazole, telithromycin, voriconazole, amiodarone, ticagrelor, imatinib, aprepitant, delavirdine, efavirenz, indinavir, nelfinavir, ritonavir, saquinavir, fluvoxamine, nefazodone, cyclosporine A, and quinine.

Supported Catalysts

In each of the above catalyst complexes, the catalyst can be used as a homogeneous catalyst in solution a reaction mixture that includes the substrate for oxidative degradation. In other embodiments, the catalyst can be a heterogeneous catalyst. Heterogeneous catalysts are typically supported, which means that the catalyst is dispersed on, encapsulated in or attached to a second material, e.g., a material that enhances the catalytic effectiveness of the catalyst, allowing for repeated use of the catalyst. A major attraction of supported catalysts is that the supported species can be separated easily, for example by filtration, from the unreacted starting materials and reaction products. This easy separation can greatly simplify product isolation procedures, and it may allow the supported reactions to be automated. Because it is possible to reuse or recycle supported reactants and because they are insoluble and nonvolatile, they are easily handled, and easily recovered. In addition, supported reactants are also attractive from an environmental point of view. Lastly, the use of supported catalysts permits adaptation of the process to a continuous flow process. Flow chemistry can be adapted to micro reactors that reduce waste and provide a 'greener' reaction process.

The present methods can optionally include immobilization of the catalysts, (e.g., metalloporphyrins, metallophthalocyanines, and metallosalen complexes) to a solid support. It is anticipated that immobilization of the catalysts will stabilize and/or modify the catalytic performance by influencing the chemo selectivity, regioselectivity and shape selectivity of the reaction. Supported catalysts, e.g., metalloporphyrins, can provide oxidation catalysts that combine the versatility of homogeneous metalloporphyrins with the advantages of heterogeneous systems, such as prevention of catalytic intermolecular self-oxidation, dimerization of sterically unhindered metalloporphyrins and easy recovery and reuse of the catalyst. Furthermore, heterogeneous catalysts have become an important attractive target to 'clean technology' since they present the possibility to minimize the problem of industrial waste treatment and disposal.

The catalysts can be anchored through electronic interactions between the π electrons of the aromatic rings of the polymers and vacant d orbitals of catalysts. For example, metalloporphyrins comprising iron, cobalt and copper have been successfully immobilized/encapsulated on a polystyrene matrix, rendering them highly dispersible in common organic solvents. The encapsulated catalysts were found to be stable and more active than their unencapsulated counterparts. These encapsulated catalysts showed enhanced activity for oxidation of substrates. These catalysts not only have high turnover frequencies but could be recovered quantitatively by simple filtration and reused without loss of activity.

Suitable supports include porous materials with a high surface area. The solid support can include, for example, polymers, metal oxides and other ceramics such as silica, titania, calcium carbonate, zeolites, molecular sieves, clay and alumina, and carbons such as activated carbon or carbon nanotubes, polymers and sulfonated or fluorinated resins. In particular, the catalyst can be immobilized onto a polymer support using known techniques. Exemplary polymer beads include polystyrene, styrene-divinylbenzene, fluorinated polymers such as TEFLON, polyethylene glycol. In particular, polystyrene having an average molecular weight of 30 kDa to 240 kDa can be used. The polymers can be halogenated. Exemplary polymer supports include, but are not limited to polyethylene, polystyrene, polycarbonate, polypropylene, polyamide, phenolic resin, epoxy resin, polycarbodiimide resin, polyvinyl chloride, polyvinylidene fluoride, polyethylene fluoride, polyimide, acrylic resin or the like.

In order to tether the catalyst to the support, the catalyst can be attached to a polymer support by reaction at one or more locations on the porphyrin or salen ring structure. The catalyst can be tethered directly or through a linker (such as an alkyl or polyalkoxy chains to the catalysts. In some embodiments, the catalytically active species are immobilized or encapsulated through chemical bonds or weaker interactions such as hydrogen bonds or donor acceptor interactions. The aryl rings of the meso-tetrakis phenyl porphinato complexes and the benzo rings of the phthalocyanine complexes provide useful locations for functional groups that can link the catalyst to a solid support. Exemplary functional groups include amino, hydroxyl and sulfonate, sulfonyl, sulfonamide, carboxylate groups. Amino groups can be introduced onto the porphyrin ring or salen ring by direct nitration, followed by reduction to the corresponding amine. The amine is used as a functional group to link to reactive species a functionalized polymer support using well-known techniques. Scheme 3 shows a reaction pathway for the nitration and sulfonation reactions useful to generate reaction nitrate and sulfonate groups.

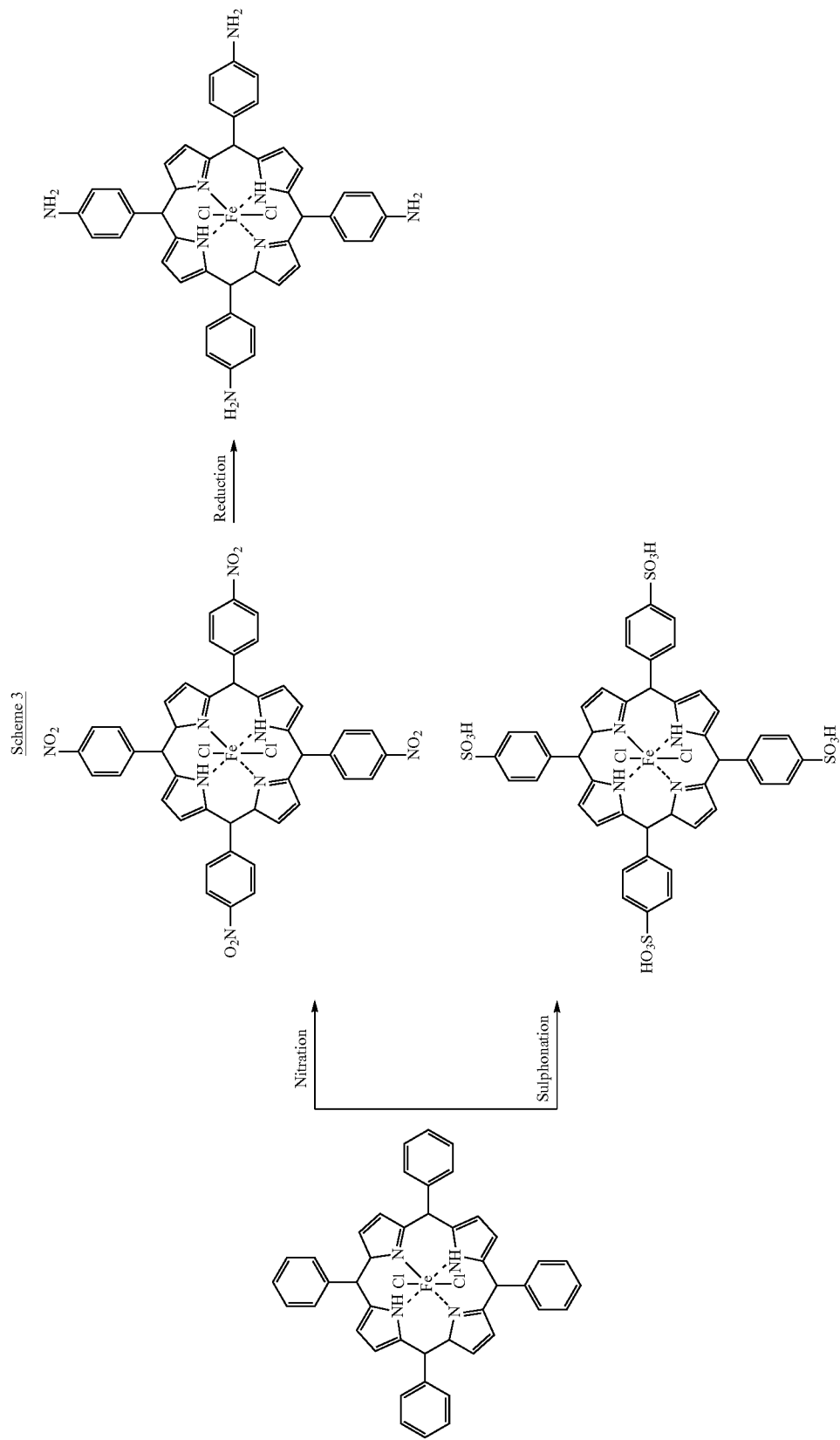

Figure 10:
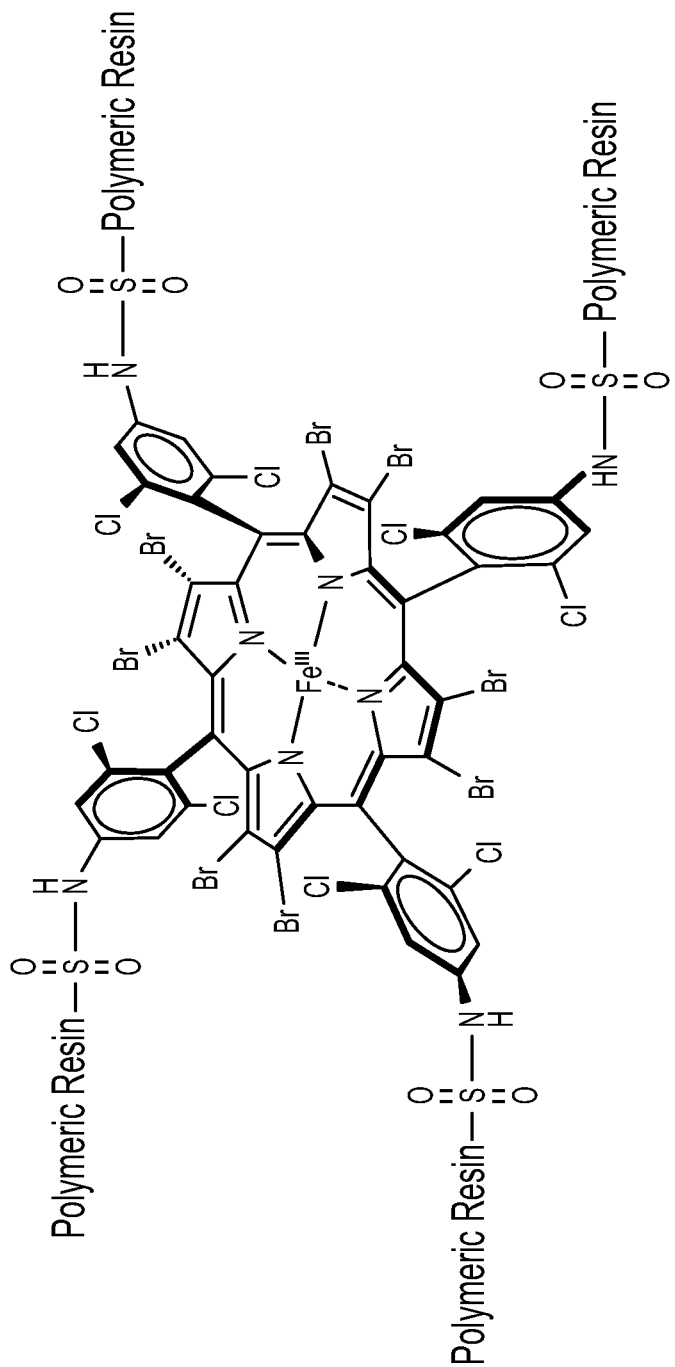
FIG. 10 shows a supported polymer complex using [Octachloro Octabromo Fe+3 TPP] 1c as the catalyst, attached to a polymeric resin solid support through sulfonamide groups (~$SO_2NH$~).
Figure 11:
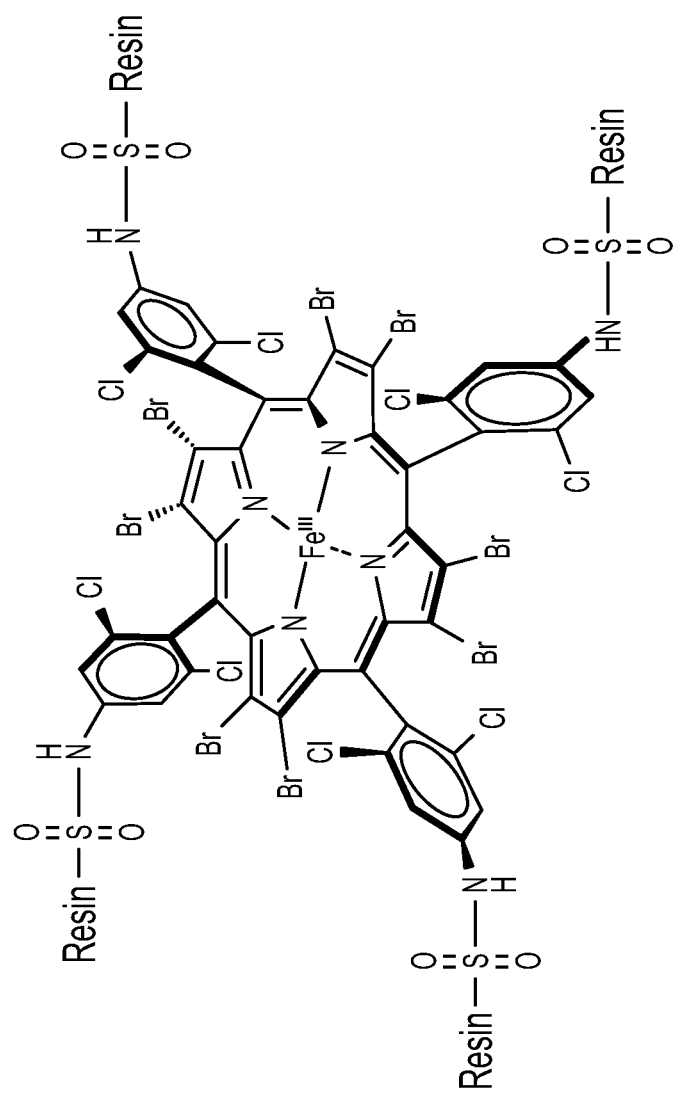
FIG. 11 shows a supported polymer complex using [Octachloro Octabromo Fe+3 TPP] 1c as the catalyst, attached to a polymeric resin solid support through aminosulfonato groups (~$NHSO_2$~).
Figure 12:
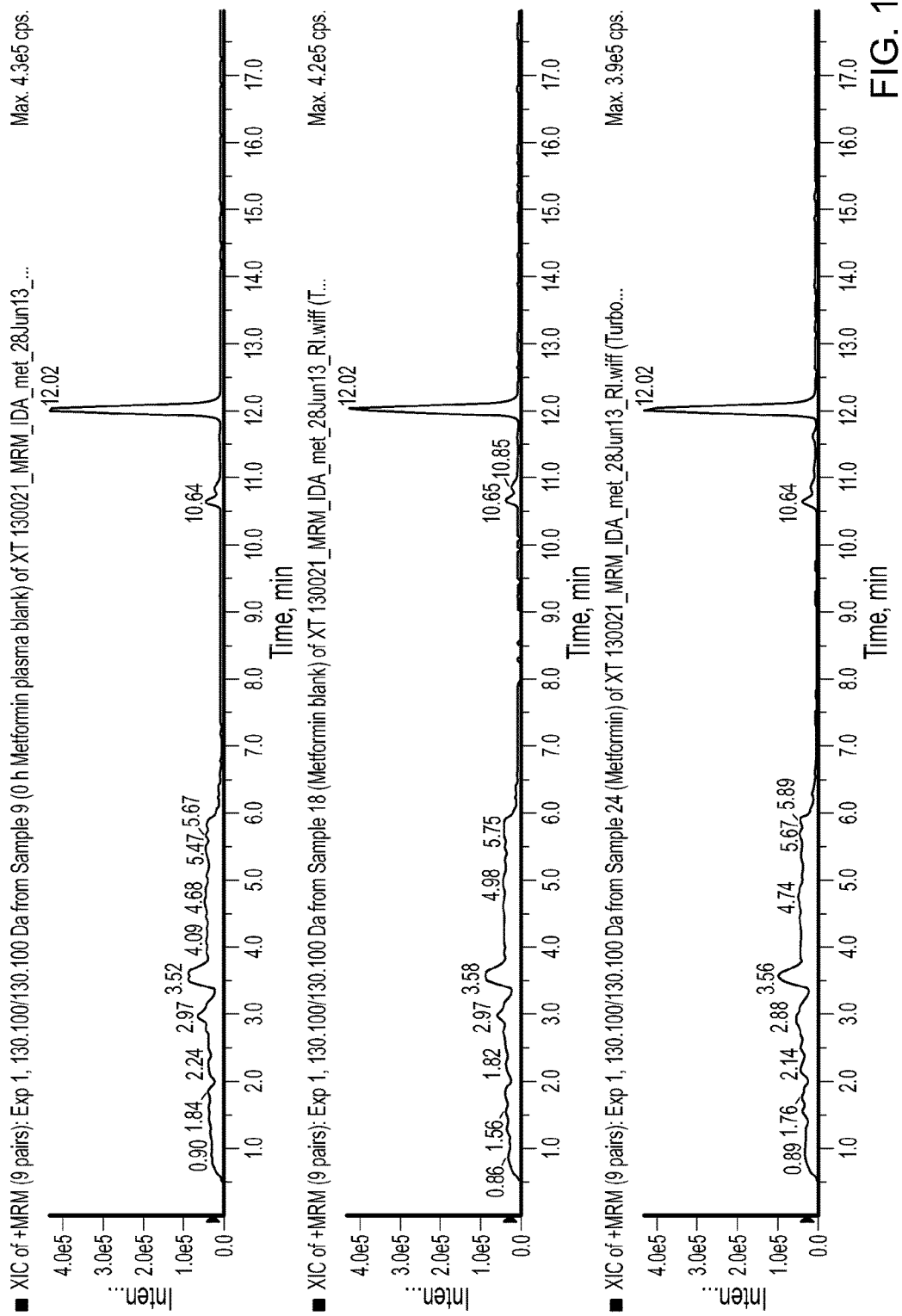
FIG. 12 provides a series of graphs showing extracted MRM chromatograms of metformin, mass transition 130.1/130.1, detected in plasma incubated with metformin (20.0 µg/mL) for 0 hour (upper) and 1 hour in the absence of catalyst (center), and 1 hour in the presence of catalyst (lower).
Figure 13:
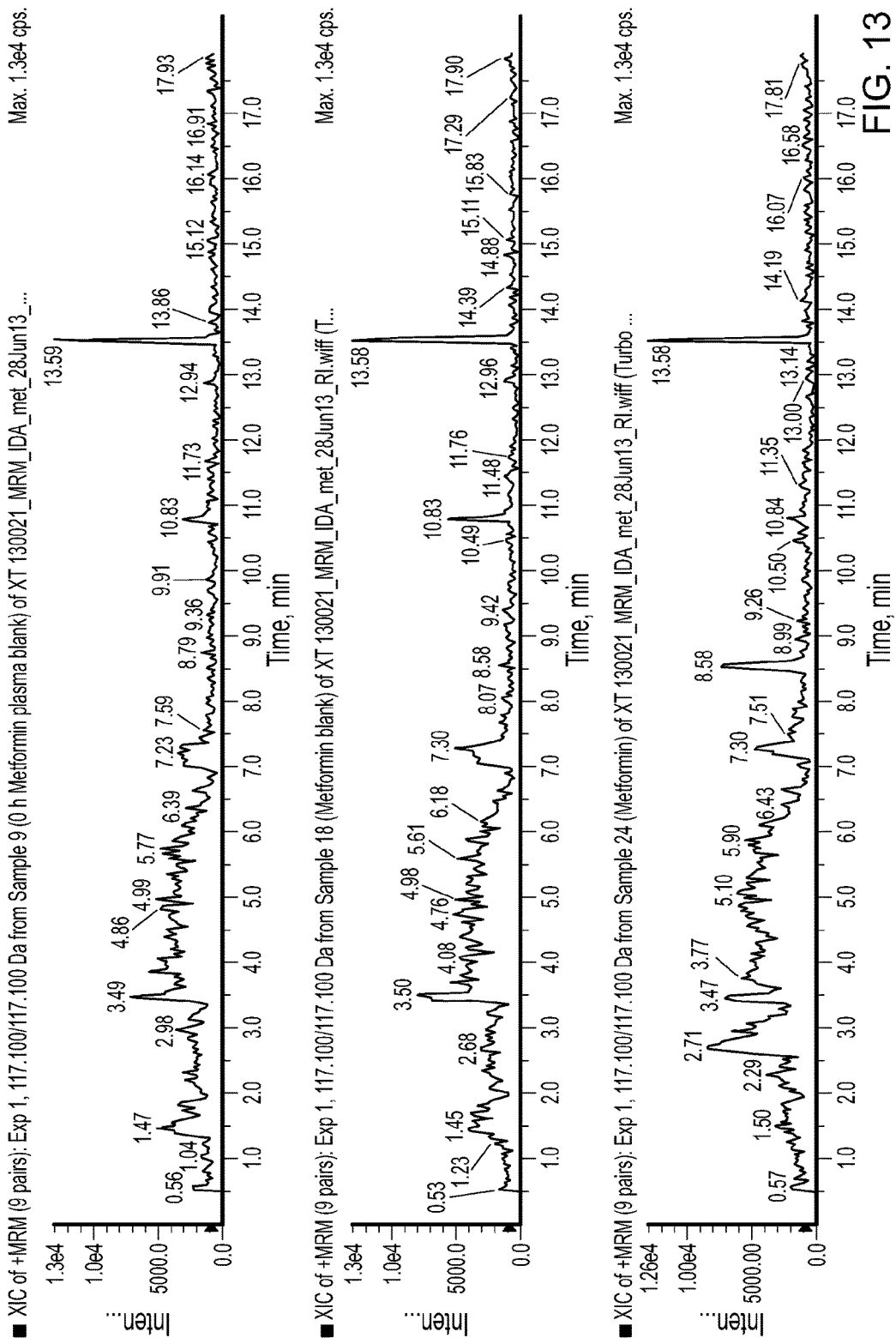
FIG. 13 provides a series of graphs showing extracted MRM chromatograms of C1, mass transition 117.1/117.1, detected in plasma incubated with metformin (20.0 µg/mL) for 0 hour (upper) and 1 hour in the absence of catalyst (center) and 1 hour in presence of catalyst (lower).
Figure 14:
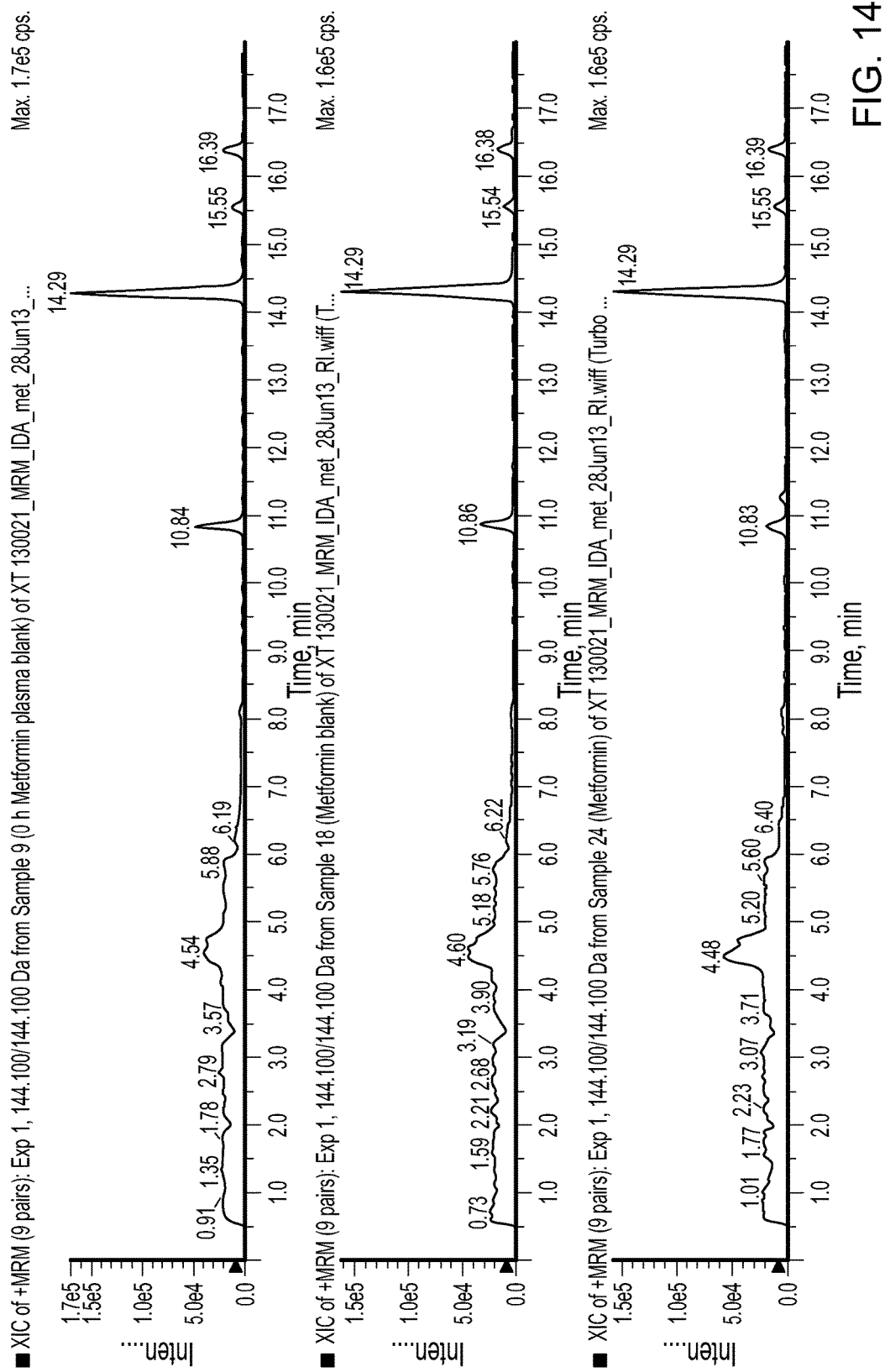
FIG. 14 provides a series of graphs showing extracted MRM chromatograms of C2 and C3, mass transition 144.1/144.1, detected in plasma incubated with metformin (20.0 µg/mL) for 0 hour (upper) and 1 hour in the absence of catalyst (center) and 1 hour in presence of catalyst (lower).
Figure 15:
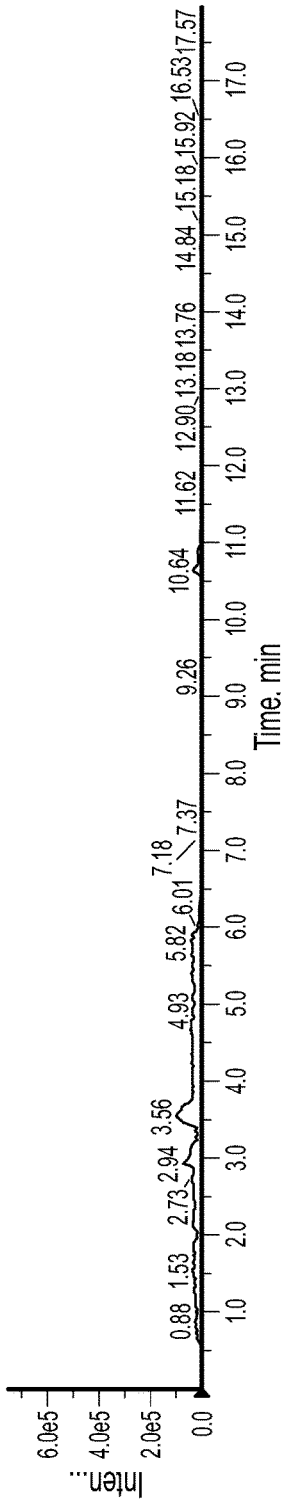
FIG. 15 provides a series of graphs showing extracted MRM chromatograms of metformin, mass transition 130.1/130.1, detected in blank plasma after 1 hour incubation (upper), 0 hour incubation of metformin in water (center) and in 50:50 water:acetonitrile (double blank) (lower).
Figure 15:
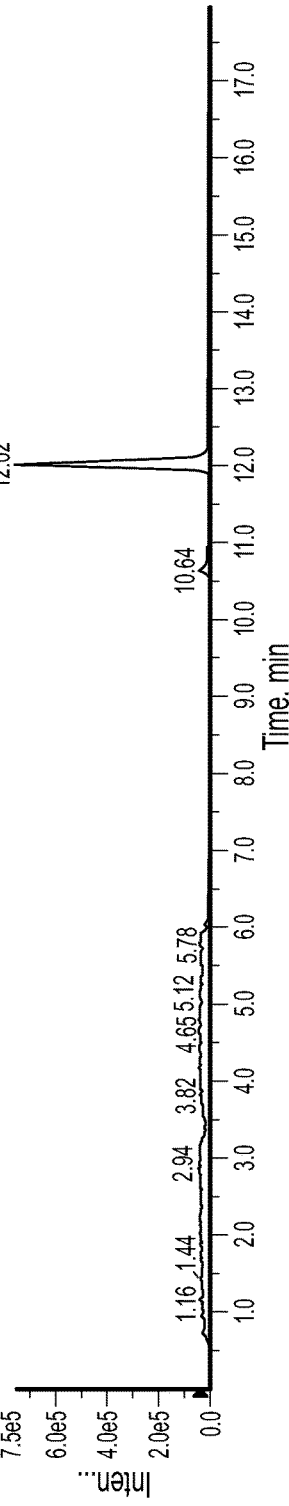
Figure 15:
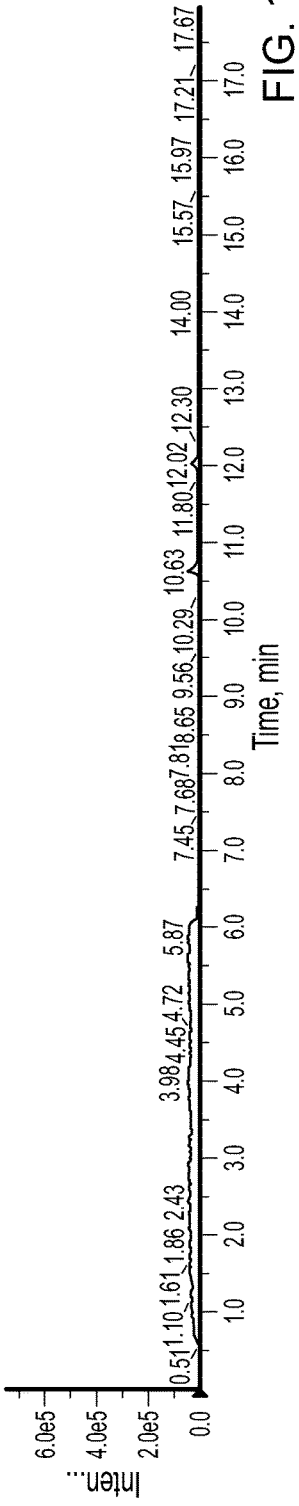
Figure 16:
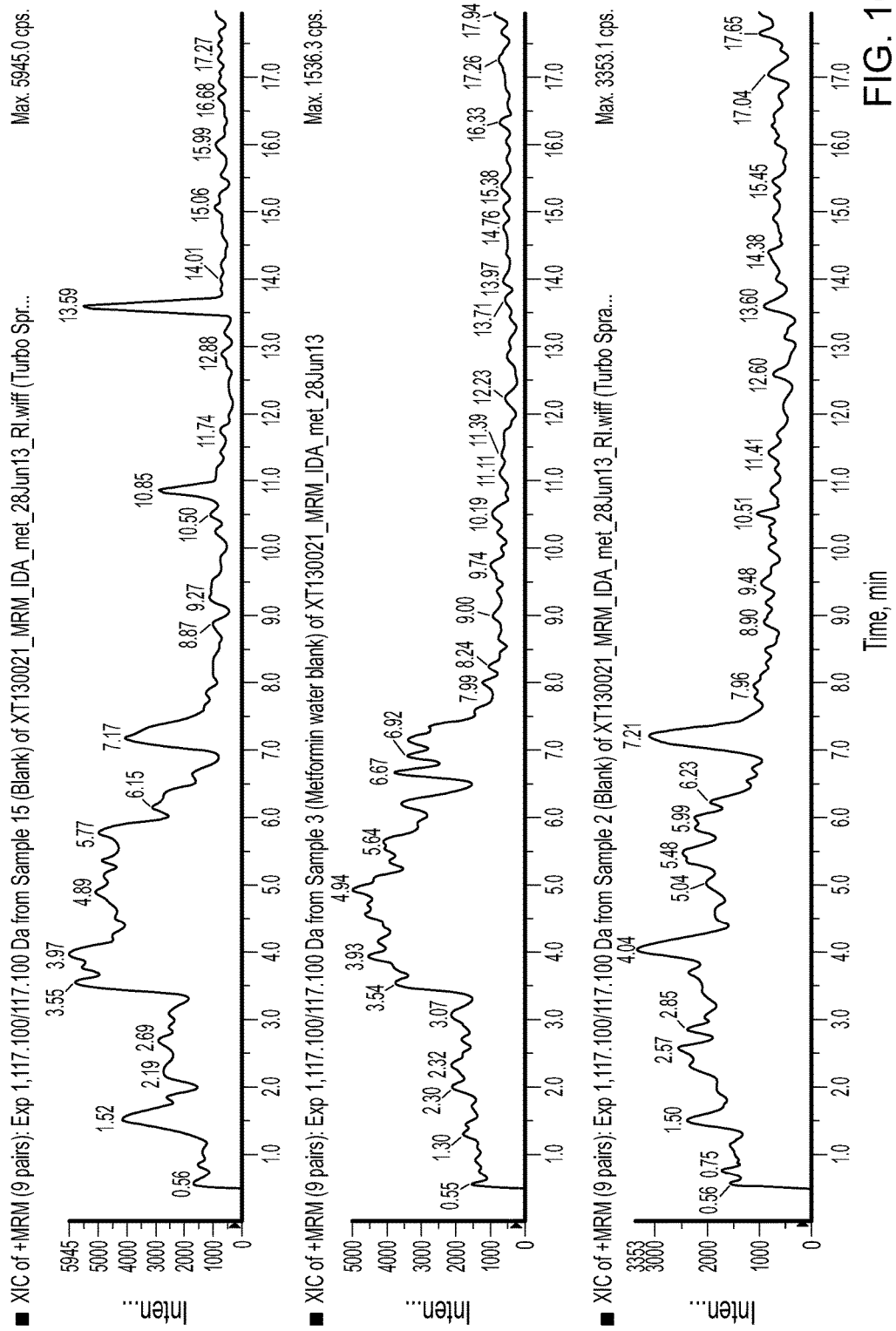
FIG. 16 provides a series of graphs showing extracted MRM chromatograms of C1, mass transition 117.1/117.1, detected in blank plasma after 1 hour incubation (upper), 0 hour incubation of metformin in water (center) and in 50:50 water:acetonitrile (double blank) (lower).
Figure 17:
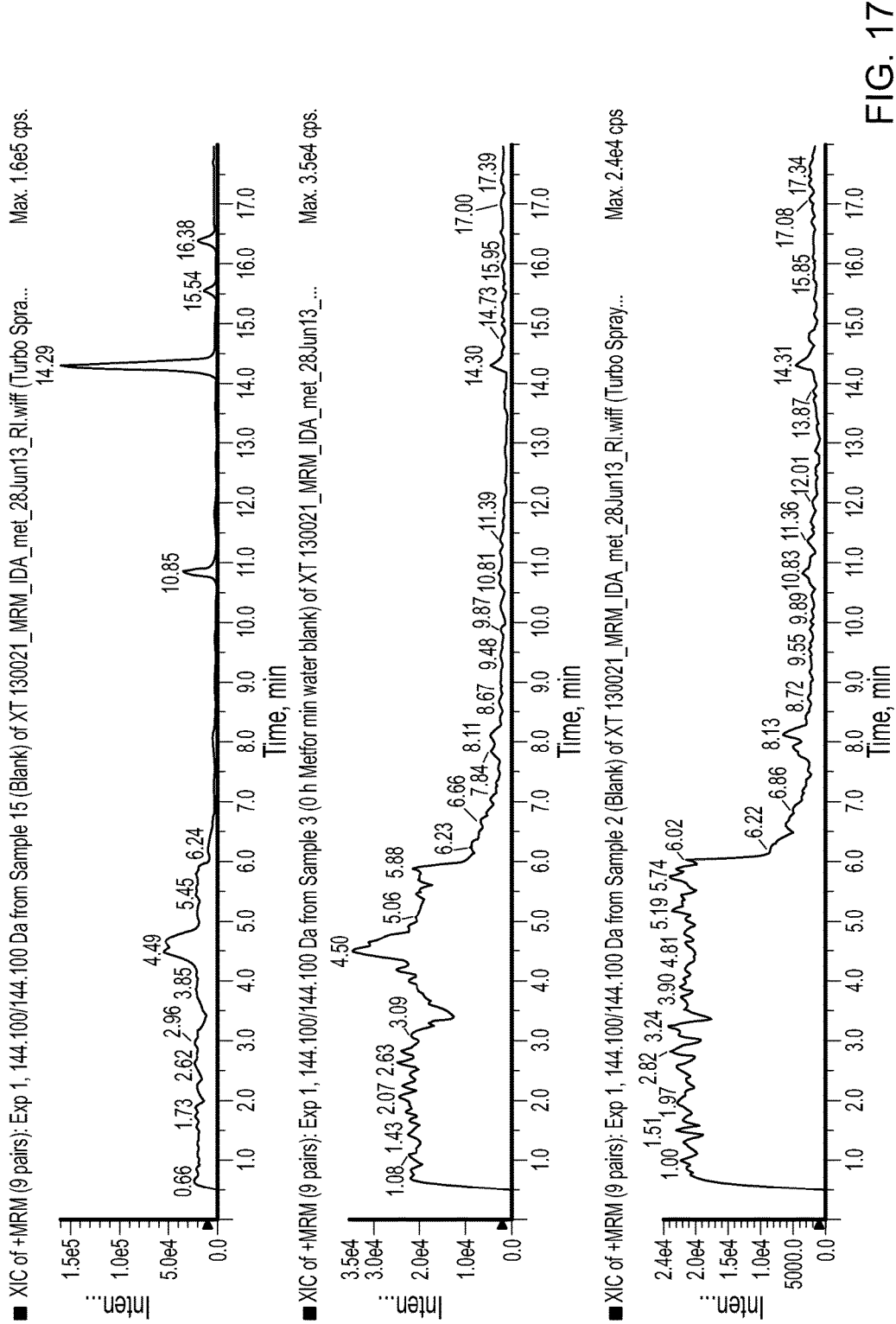
FIG. 17 provides a series of graphs showing extracted MRM chromatograms of C2 and C3, mass transition 144.1/144.1, detected in blank plasma after 1 hour incubation (upper), 0 hour incubation of metformin in water (middle) and in 50:50 water:acetonitrile (double blank) (lower).

FIG. 10 shows a supported polymer complex using [Octachloro Octabromo Fe+3 TPP] 1c as the catalyst, attached to a polymeric resin solid support through sulfonamide groups (~SO$_2$NH~). Similarly, FIG. 11 shows a supported polymer complex using [Octachloro Octabromo Fe+3 TPP] 1c as the catalyst, attached to a polymeric resin solid support through aminosulfonato groups (~NHSO$_2$~).

In other embodiments, the polymer support can be in the shape of a ribbon, gels, beads, strips, coils and the like. Polymer-supported catalyst can be prepared in the form of beads of about 50-100 micrometers diameter. The beads are functionalized (on the interior and/or exterior surfaces) with groups that react with and tether the catalyst to the solid support. The catalysts can be made into spheres, ribbons, flat sheets, immobilized matrices of one layer thickness, tubular coils, which are available in a range of materials. These are readily replaced or interchanged. Sections of coil are interchangeable with cartridges that can be loaded with solid supported catalysts or reagents.

Further, the immobilized catalysts disclosed herein are ideally suited for flow systems (e.g., microfluidic and lab-on-a-chip devices) and flow-through processes (e.g., continuous flow processes). Continuous flow systems and methods allow for the immobilized catalyst to permanently reside in the system where it transforms the entering starting materials (e.g., pharmaceutical compounds) into the desired products (e.g., metabolites). Thus, in one aspect, the polymer support is part of a fluidic flow system.

In one aspect, the present disclosure provides a fluidic flow system (e.g., a sample processing device) comprising an inlet that receives flow of a sample solution and directs the sample solution flow to flow chamber, a flow chamber comprising one or more catalysts immobilized on a substrate, and at least one outlet that receives the sample solution flow from the flow chamber.

These immobilized systems have obvious advantages because the catalysts are more easily separated from products and recycled which is especially important when dealing with fairly expensive catalysts, (e.g., metalloporphyrins, metallophthalocyanines, and metallosalen complexes).

In one or more embodiments, the catalyst can be supported using encapsulation technology. Immobilization methods can include physical envelopment of the catalyst in a polymer matrix. e.g., in acrylic polymers and copolymers, carboxyvinyl polymer, polyamides, polystyrene, polyvinyl acetate, polyvinyl acetate phthalate, polyvinylpyrrolidone, and combinations thereof. During catalytic oxidation using metalloporphyrins or metallophthalocyanines under homogeneous conditions, the system can encounter challenges such as catalysts separation, dimerization and catalyst destruction. These challenges can be avoided by using a polymer microencapsulated catalyst. Microencapsulation is a method for immobilizing catalysts onto polymers such as ionic resins and polystyrene on the basis of physical entrapment in the polymer matrix. The catalysts are firmly anchored through the electronic interactions between the π electrons of the benzene rings of the polystyrene-based polymers and the vacant d orbitals of the catalyst. This is an efficient and easy method for immobilization of commercially available metalloporphyrins and metallophthalocyanines onto polystyrenes in general, which gives stable, reusable and highly efficient catalysts for aerobic oxidation of alcohols and exhibit enhanced activity over their unencapsulated counterparts.

The method of encapsulation was standardized using different types of polystyrene polymers as well as different metallophthalocyanines. Metallophthalocyanines of iron, cobalt and copper have been successfully encapsulated on polystyrene matrices, rendering them highly dispersible in common organic solvents. An exemplary reaction scheme for the encapsulation of metallophthalocyanines is shown in Scheme 4.

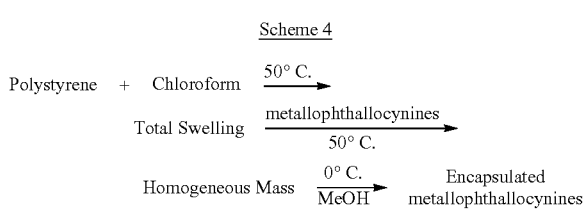

Scheme 4

Using this micro encapsulation technique (Scheme 4), metalloporphyrins of manganese have been successfully encapsulated in polystyrene matrix. The manganese porphyrins have been anchored onto polymer on the basis of physical envelopment by the polystyrene fibers, rendering them highly dispersible in common organic solvents.

Phase-Transfer Agents

Under certain conditions, the reaction mixtures disclosed herein can form biphasic reaction mixtures. For biphasic reaction mixtures, the disclosure further provides the use of phase-transfer agents (e.g., phase-transfer catalysts) to facilitate the migration of a reactant from one phase into another phase where reaction occurs. Phase-transfer catalysts include, but are not limited to, quaternary-ammonium salts, tetra-n-butylammonium bromide (TBAB), tricaprylylmethylammonium chloride, hexadecyltributylphosphonium bromide, tetrabutylphosphonium bromide, 18-crown-6, aliquat 336, benzyltriethylammonium chloride (TEBA), methyltrioctylammonium hydrogen sulfate (TOMAHS), cetylpyridinium chloride, tetrahexylammonium bromide. N-benzylcinchonidinium bromide, and N-benzylcinchoninium bromide.

EXAMPLES

The invention is further described in the following examples, which do not limit the scope of the invention described in the claims.

In the following examples, the ability of selected catalysts to generate major human metabolites of compounds related to the treatments of diabetes, hypertension and dyslipidemia were evaluated. All of those drugs have published metabolite profile data that were used to compare observed experimental results against.

Example 1. Glimepiride Microwave Protocol

Glimepiride API (20.0 mg, 0.04076 mmol) extracted using 50 mL 1:1 methanol:ethanol, filtered and concentrated in vacuo. The resulting solid taken up in 2:0.25 mL acetonitrile:water and transferred to a microwave tube. Octabromo tetrakis(2,6-dichlorophenyl)porphyrin Fe(III)Cl (3.28 mg, 0.002038 mmol) then added, followed by sodium hypochlorite (50.3 uL, 0.10191 mmol). The reaction is carried out in the microwave at 80° C. for 50 minutes. (representative, see table below for additional conditions).

Workup: Reaction diluted with 40 mL chloroform. Washed 3×40 mL water. Washed 3×40 mL brine. Back-extracted aqueous layer with 40 mL chloroform. Organic layers combined and dried over MgSO4, filtered and concentrated in vacuo. Details of analysis are found below.

Representative HPLC-ESI-MS Parameters:
HPLC Parameters: Agilent 1200 HPLC, Binary pump, DAD, 100 tray autosampler. Column: Waters Xterra C18-MS, 4.6×5 cm, 3.5 um particle size, mobile phase A: water+0.1% formic acid, mobile phase B: ACN+0.1% formic acid, Flow rate: 1.0 mL/min,
Injection volume: 25 uL. Gradient 0 min 10% B hold for 1 minute, 10-80% B in 20 min. hold for 2 min.
Positive mode ESI parameters: Thermo TSQ Quantum Ultra, standard ESI source, Spray voltage: 4000V, Sheath gas pressure: 50 psi N2. Ion sweep gas pressure: 0.0 psi, Aux gas pressure: 0 psi, Capillary temperature: 325 C, Capillary offset: 35V, Tune lens offset: 117V, Skimmer offset: 0V, Collision Pressure: 1.5 mTorr Ar.
Positive mode MS/MS parameters: Thermo LCQ Deca XP Plus 3D linear ion trap. Spray voltage: 3.5 kV. Desolvation gas: 40.
Selective Reaction Monitoring (SRM) Parameters:
Scan events: 1, Scan Type: SRM, Scan Time: 0.9 s, Coll. energy: 28V, Q1 Peak width: 2.0 m/z FWHM, Q3 Peak width: 1.0 m/z FWHM, Scan width: 1.0 m/z.

Identification of glimepiride metabolites following optimal microwave reaction in the presence of Octabromo tetrakis(2,6-dichlorophenyl)porphyrin Fe(III)Cl are provided in Table 1 and FIG. 1.

TABLE 1

Glimepiride Microwave results

| Spec. Reference | Scan Range: Respective Metabolite | MS MODE | Optimal µwave Conditions | Retention Time (min) |
|---|---|---|---|---|
| 1 | m/z 490.72 → 491.72: GLM | SIM | N/A | 8.55 |
| 2 | m/z 506.50 → 507.50: OH-GLM | SIM | 80° C., 50 min. | 4.43 |
| 3 | m/z 520.50 → 521.50: CO$_2$H-GLM | SIM | 80° C., 50 min. | 4.40 |

Glimepiride Metabolite Structures:

| Compound | Structure |
|---|---|
| Glimepiride (GLM) Chemical Formula: C$_{24}$H$_{34}$N$_4$O$_5$S Exact Mass: 490.22 | 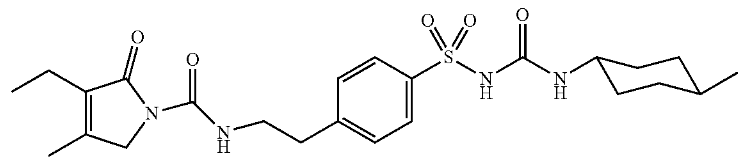 [SMILES: CCC1=C(C)CN(C(=O)NCCc2ccc(S(=O)(=O)NC(=O)NC3CCC(C)CC3)cc2)C1=O] |
| cis/trans-Hydroxyglimepiride Chemical Formula: C$_{24}$H$_{34}$N$_4$O$_6$S Exact Mass: 506.22 | 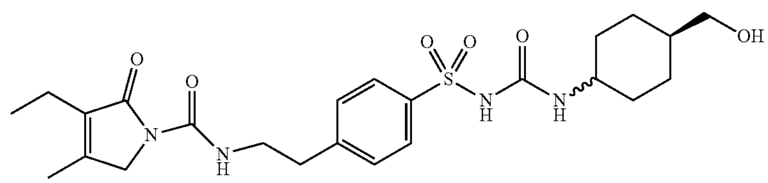 |
| Carboxyglimepiride Chemical Formula: C$_{24}$H$_{32}$N$_4$O$_7$S Exact Mass: 520.20 | 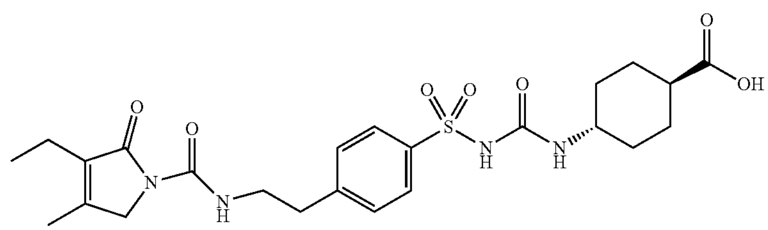 [SMILES: CCC1=C(C)CN(C(=O)NCCc2ccc(S(=O)(=O)NC(=O)N[C@H]3CC[C@H](C(=O)O)CC3)cc2)C1=O] |

Example 2. Spironolactone Microwave Protocol

Spironolactone API (100.0 mg, 0.2401 mmol) extracted using 100 mL 1:1 methanol:ethanol, filtered and concentrated in vacuo. The resulting solid taken up in 3:0.5 mL acetonitrile:water and transferred to a microwave tube. Octabromo tetrakis(2,6-dichlorophenyl)porphyrin Fe(III)Cl (19.33 mg, 0.012 mmol) then added, followed by sodium hypochlorite (296 uL, 0.0.6001 mmol). Reaction run in the microwave at 80° C. for 50 minutes (representative, see table below for additional conditions).

Workup: Reaction diluted with 40 mL chloroform. Washed 3×40 mL water. Washed 3×40 mL brine. Back-extracted aqueous layer with 40 mL chloroform. Organic layers combined and dried over MgSO4, filtered and concentrated in vacuo. Samples analyzed according to parameters provided in Example 1.

Figure 2:
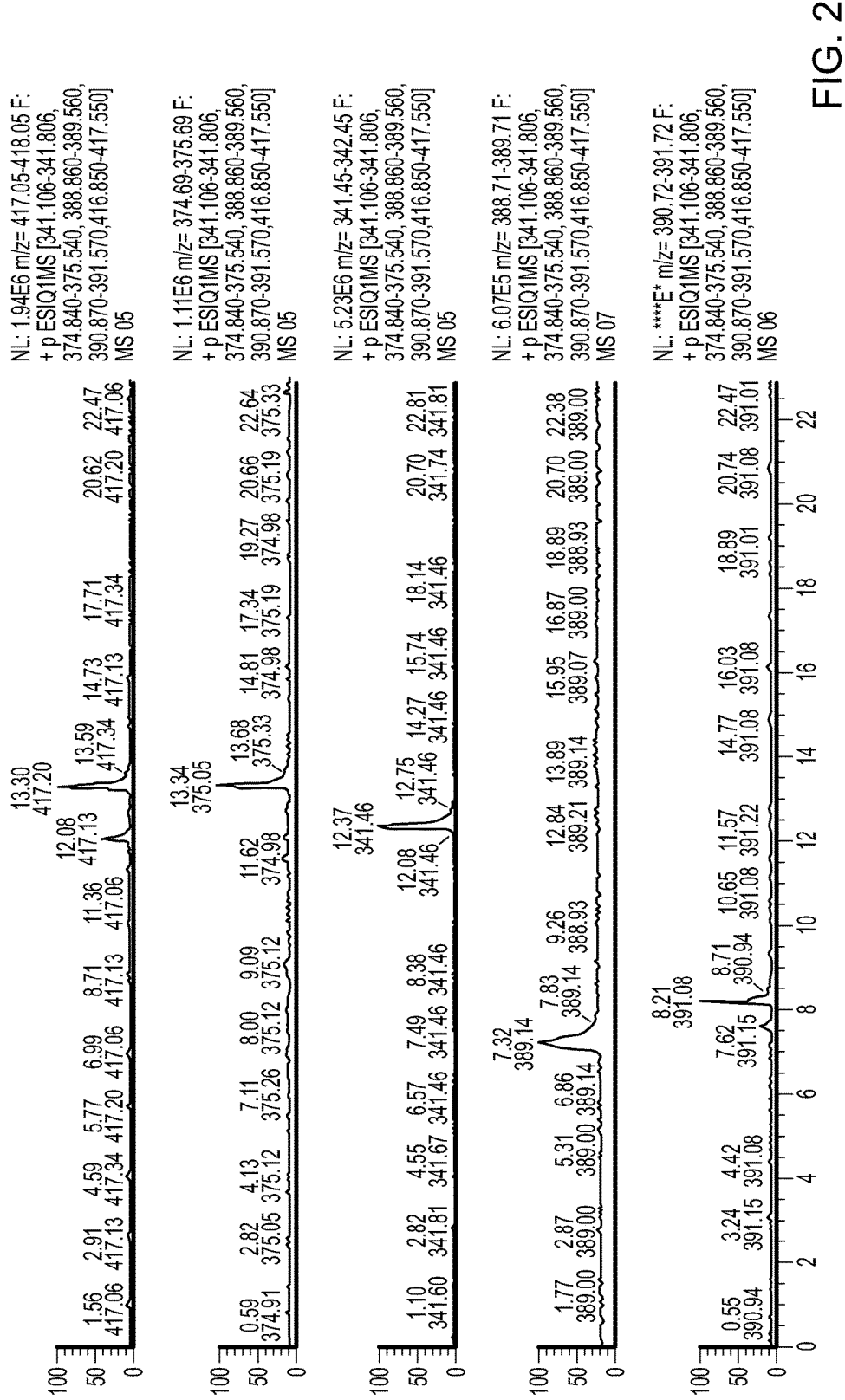
FIG. 2 is a representative MS-SIM chromatogram demonstrating representative spironolactone metabolites produced following microwave reaction in the presence of Octabromo tetrakis(2,6-dichlorophenyl)porphyrin Fe(III)Cl.

Identification of spironolactone metabolites following optimal microwave reaction in the presence of Octabromo tetrakis(2,6-dichlorophenyl)porphyrin Fe(III)Cl are provided in Table 2 and FIG. 2.

TABLE 2

Spironolactone Microwave results:

| Spec. Reference | Scan Range: Respective Metabolite | MS MODE | Optimal µwave Conditions | Retention Time (min) |
|---|---|---|---|---|
| 1 | m/z 417.05→418.05: Spironolactone | SIM | N/A | 13.30 |
| 2 | m/z 374.69→375.69: TH | SIM | 80° C., 50 min. | 13.34 |
| 3 | m/z 341.45→342.45: Canrenone | SIM | 80° C., 50 min. | 12.37 |
| 4 | m/z 388.71→389.71: TM | SIM | 80° C., 10 min. | 7.28 |
| 5 | m/z 390.72→391.72: 3-α/β-hydroxy-TM | SIM | 80° C., 30 min. | 7.66/8.21 |

Spironolactone Metabolite Structures:

| Compounds | Structure |
|---|---|
| Spironolactone (SP) Chemical Formula: $C_{24}H_{32}O_4S$ Exact Mass: 416.20 | 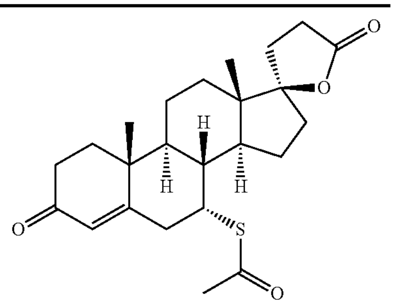 |
| TH Chemical Formula: $C_{22}H_{30}O_3S$ Exact Mass: 374.19 | 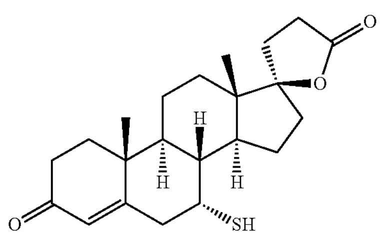 |
| Canrenone (CAN) Chemical Formula: $C_{22}H_{28}O_3$ Exact Mass: 340.20 | |
| TM Chemical Formula: $C_{23}H_{32}O_3S$ Exact Mass: 388.21 | 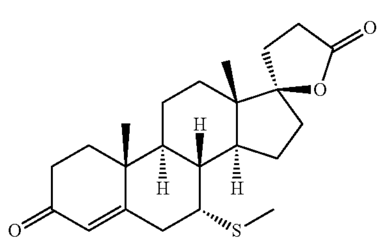 |
| 3α-Hydroxy-TM Chemical Formula: $C_{23}H_{34}O_3S$ Exact Mass: 390.22 | |
| 3β-Hydroxy-TM Chemical Formula: $C_{23}H_{34}O_3S$ Exact Mass: 390.22 | |

Example 3. Nifedipine Microwave Protocol

Nifedipine API (30.0 mg, 0.08662 mmol) extracted using 60 mL 1:1 methanol:ethanol, filtered and concentrated in vacuo. The resulting solid taken up in 2:0.25 mL acetonitrile: water and transferred to a microwave tube. Octabromo tetrakis(2,6-dichlorophenyl)porphyrin Fe(III)Cl (6.98 mg, 0.004331 mmol) then added, followed by sodium hypochlorite (106.9 uL, 0.21655 mmol). Reaction run in the microwave at 80° C. for 50 minutes. (representative, see table below for additional conditions).

Workup: Reaction diluted with 40 mL chloroform. Washed 3×40 mL water. Washed 3×40 mL brine. Back-extracted aqueous layer with 40 mL chloroform. Organic layers combined and dried over MgSO4, filtered and concentrated in vacuo. Samples analyzed according to parameters provided in Example 1.

Figure 3:
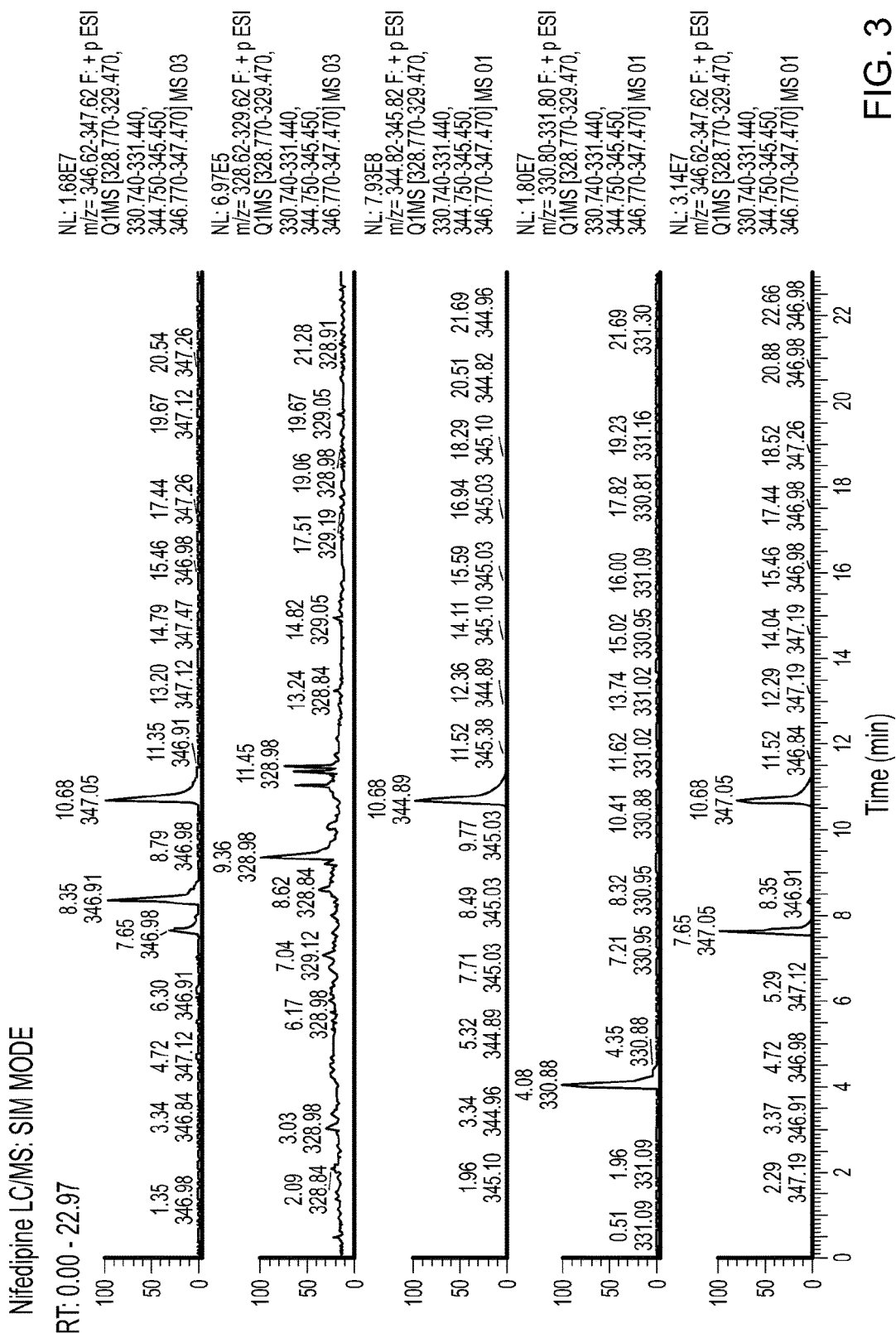
FIG. 3 is a representative MS-SIM chromatogram demonstrating representative nifedipine metabolites produced following microwave reaction in the presence of Octabromo tetrakis(2,6-dichlorophenyl)porphyrin Fe(III)Cl.

Identification nifedipine metabolites following optimal microwave reaction in the presence of Octabromo tetrakis (2,6-dichlorophenyl)porphyrin Fe(III)Cl are provided in Table 3 and FIG. 3.

TABLE 3

Nifedipine Microwave Results:

| Spec. Reference | Scan Range: Respective Metabolite | MS MODE | Optimal µwave Conditions | Retention Time (min) |
|---|---|---|---|---|
| 1 | m/z 346.62 → 347.62: Nifedipine | SIM | N/A | 8.35 |
| 2 | m/z 328.62 → 329.47: NIF1 | SIM | 80° C., 10 min | 9.36 |
| 3 | m/z 344.82 → 345.82: NIF2 | SIM | 80° C., 50 min | 10.68 |
| 4 | m/z 330.80 → 331.80: NIF3 | SIM | 80° C., 50 min | 4.08 |
| 5 | m/z 346.62 → 347.62: NIF4 | SIM | 80° C., 50 min | 7.65 |

Nifedipine Metabolite Structures:

| Compound | Structure |
|---|---|
| Nifedipine (NIF) Chemical Formula: $C_{17}H_{18}N_2O_6$ Exact Mass: 346.1165 | 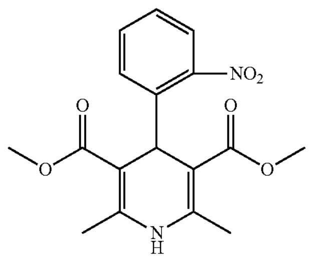 |
| Hydroxy-Dehydronifedipin-lactone (NIF1) Chemical Formula: $C_{16}H_{12}N_2O_6$ Exact Mass: 328.0695 | 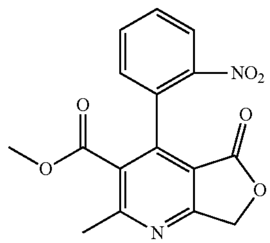 [SMILES: COC(=O)c1c(C)nc2c(c1-c1ccccc1[N+](=O)[O-])C(=O)OC2] |
| Dehydro-nifedipine (NIF2) Chemical Formula: $C_{17}H_{16}N_2O_6$ Exact Mass: 344.1008 | 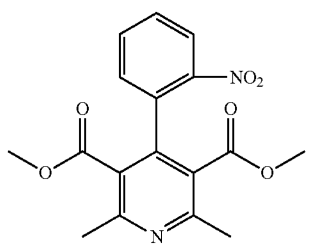 |
| Dehydro-nifidipinic Acid (NIF3) Chemical Formula: $C_{16}H_{14}N_2O_6$ Exact Mass: 330.0852 | 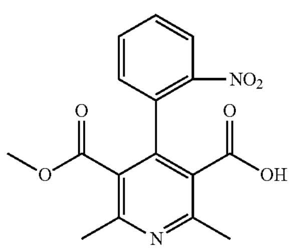 [SMILES: COC(=O)c1c(C)nc(C)c(C(=O)O)c1-c1ccccc1[N+](=O)[O-]] |
| Dehydronifedipin-lactone (NIF4) Chemical Formula: $C_{16}H_{14}N_2O_7$ Exact Mass: 346.0801 | 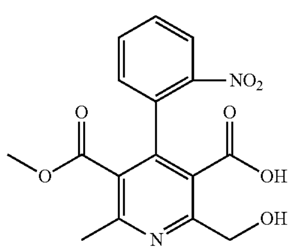 [SMILES: COC(=O)c1c(C)nc(CO)c(C(=O)O)c1-c1ccccc1[N+](=O)[O-]] |

Example 4. Amlodipine Microwave Protocol

Amlodipine API (20.0 mg, 0.04891 mmol) extracted using 50 mL 1:1 methanol:ethanol, filtered and concentrated in vacuo. The resulting solid taken up in 2:0.25 mL acetonitrile:water and transferred to a microwave tube. Octabromo tetrakis(2,6-dichlorophenyl)porphyrin Fe(III)Cl (3.94 mg, 0.00245 mmol) then added, followed by sodium hypochlorite (60.4 uL, 0.12228 mmol). Reaction run in the microwave at 80° C. for 50 minutes. (representative, see table below for additional conditions).

Workup: Reaction diluted with 40 mL chloroform. Washed 3×40 mL water. Washed 3×40 mL brine. Back-extracted aqueous layer with 40 mL chloroform. Organic layers combined and dried over MgSO4, filtered and concentrated in vacuo. Samples analyzed according to parameters in Example 1.

Figure 4:
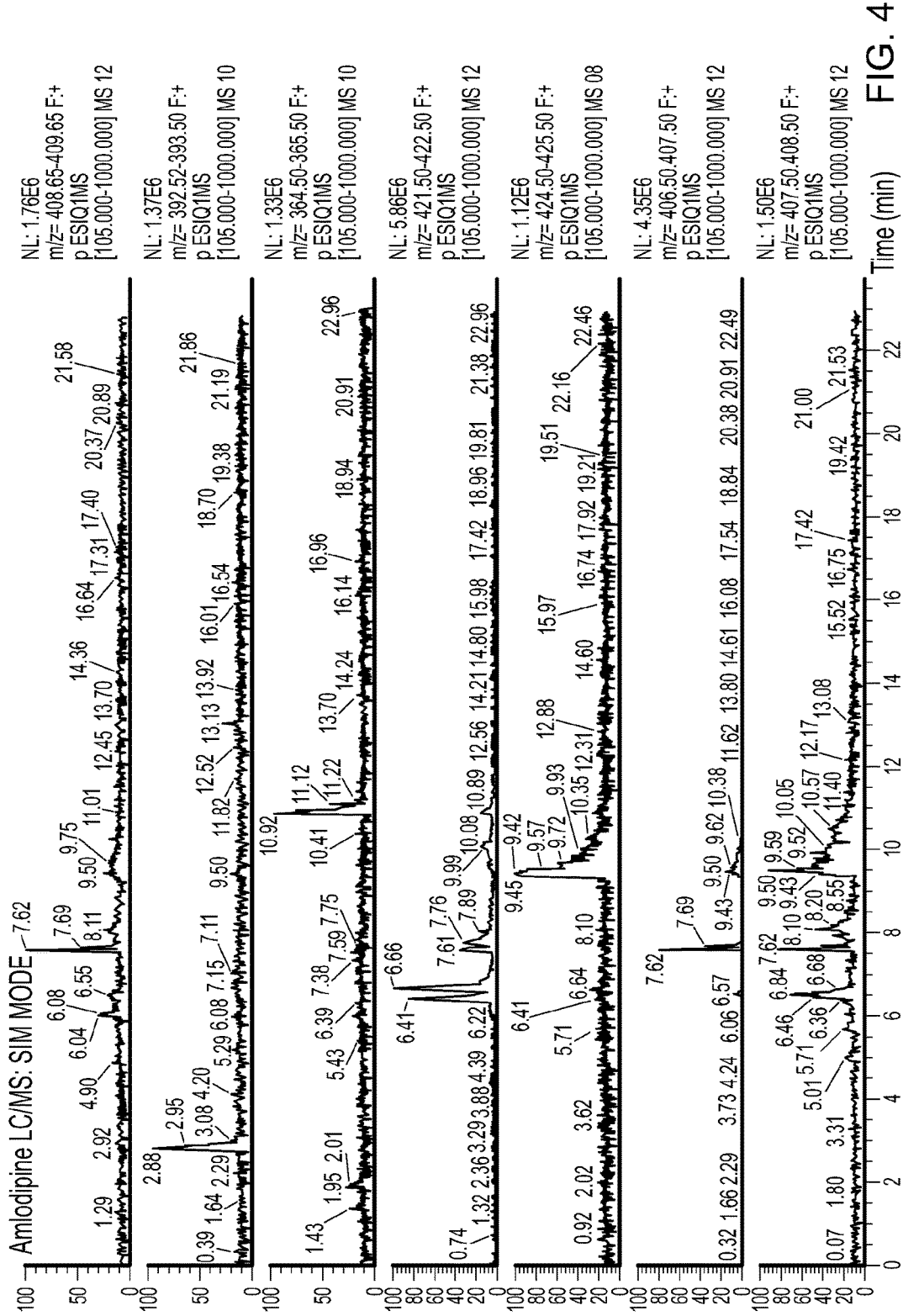
FIG. 4 is a representative MS-SIM chromatograms demonstrating representative amlodipine metabolites produced following microwave reaction in the presence of Octabromo tetrakis(2,6-dichlorophenyl)porphyrin Fe(III)Cl.

Identification of amlodipine metabolites following optimal microwave reaction in the presence of Octabromo tetrakis(2,6-dichlorophenyl)porphyrin Fe(III)Cl are provided in Table 4 and FIG. 4.

TABLE 4

Amlodipine Microwave Results:

| Spec. Reference | Scan Range: Respective Metabolite | MS MODE | Optimal µwave Conditions | Retention Time (min) |
|---|---|---|---|---|
| 1 | m/z 408.65→ 409.65: Amlodipine API | SIM | N/A | 7.63 |
| 2 | m/z 392.50→ 393.50: AML1 | SIM | 80° C., 30 min | 2.88 |
| 3 | m/z 364.50→ 365.50: AML2 | SIM | 80° C., 30 min | 10.92 |
| 4 | m/z 421.50→ 422.50: AML3 | SIM | 80° C., 10 min | 6.41, 6.66 |
| 5 | m/z 424.50→ 425.50: AML4 | SIM | 80° C., 50 min | 9.40 |
| 6 | m/z 406.50→ 407.50: AML5 | SIM | 80° C., 10 min | 7.69 |
| 7 | m/z 407.50→ 408.50: AML6 | SIM | 80° C., 10 min | 8.10 |

Amlodipine Metabolite Structures:

| Compound | Structure |
|---|---|
| Amlodipine (AML) Chemical Formula: $C_{20}H_{25}ClN_2O_5$ Exact Mass: 408.15 | 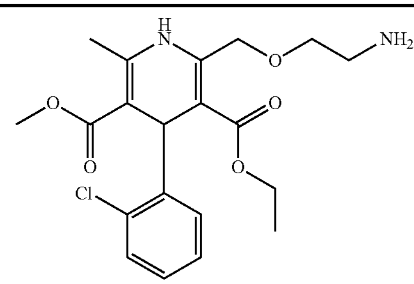 |
| AML1 Chemical Formula: $C_{19}H_{21}ClN_2O_5$ Exact Mass: 392.11 | 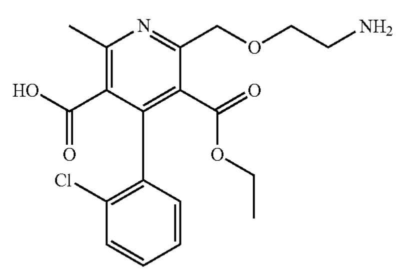 [SMILES: CCOC(=O)c1c(COCCN)nc(C)c(C(=O)O)c1-c1ccccc1Cl] |
| AML2 Chemical Formula: $C_{18}H_{18}ClNO_5$ Exact Mass: 363.09 | 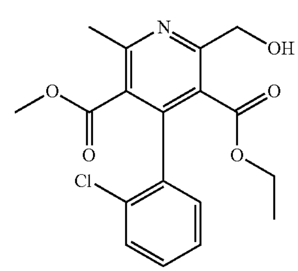 [SMILES: CCOC(=O)c1c(CO)nc(C)c(C(=O)OC)c1-c1ccccc1Cl] |

| Compound | Structure |
|---|---|
| AML3 Chemical Formula: $C_{20}H_{20}ClNO_7$ Exact Mass: 421.09 | 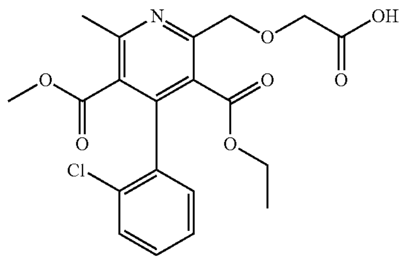 [SMILES: CCOC(=O)c1c(COCC(=O)O)nc(C)c(C(=O)OC)c1-c1ccccc1Cl] |
| AML4 Chemical Formula: $C_{19}H_{18}ClNO_8$ Exact Mass: 423.07 | 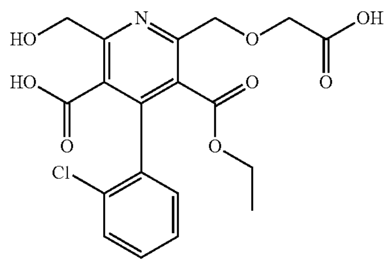 [SMILES: CCOC(=O)c1c(COCC(=O)O)nc(CO)c(C(=O)O)c1-c1ccccc1Cl] |
| AML5 Chemical Formula: $C_{20}H_{23}ClN_2O_5$ Exact Mass: 406.13 | 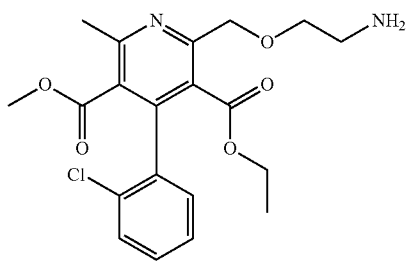 [SMILES: CCOC(=O)c1c(COCCN)nc(C)c(C(=O)OC)c1-c1ccccc1Cl] |
| AML6 Chemical Formula: $C_{19}H_{18}ClNO_7$ Exact Mass: 407.08 | 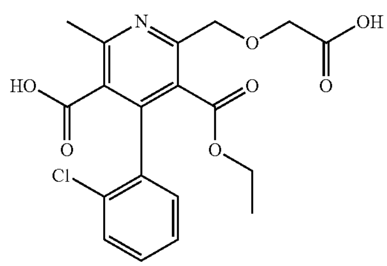 [SMILES: CCOC(=O)c1c(COCC(=O)O)nc(C)c(C(=O)O)c1-c1ccccc1Cl] |

Example 5. Atorvastatin Microwave Protocol

Atorvastatin API (40.0 mg, 0.07160 mmol) extracted using 80 mL 1:1 methanol:ethanol, filtered and concentrated in vacuo. The resulting solid taken up in 2:0.25 mL acetonitrile:water and transferred to a microwave tube. Octabromo tetrakis(2,6-dichlorophenyl)porphyrin Fe(III)Cl (5.77 mg, 0.00358 mmol) then added, followed by sodium hypochlorite (88.4 uL, 0.17901 mmol). Reaction run in the microwave at 80° C. for 50 minutes. (representative, see table below for additional conditions).

Workup: Reaction diluted with 40 mL chloroform. Washed 3×40 mL water. Washed 3×40 mL brine. Back-extracted aqueous layer with 40 mL chloroform. Organic layers combined and dried over MgSO4, filtered and concentrated in vacuo. Samples analyzed according to parameters in Example 1.

Figure 5:
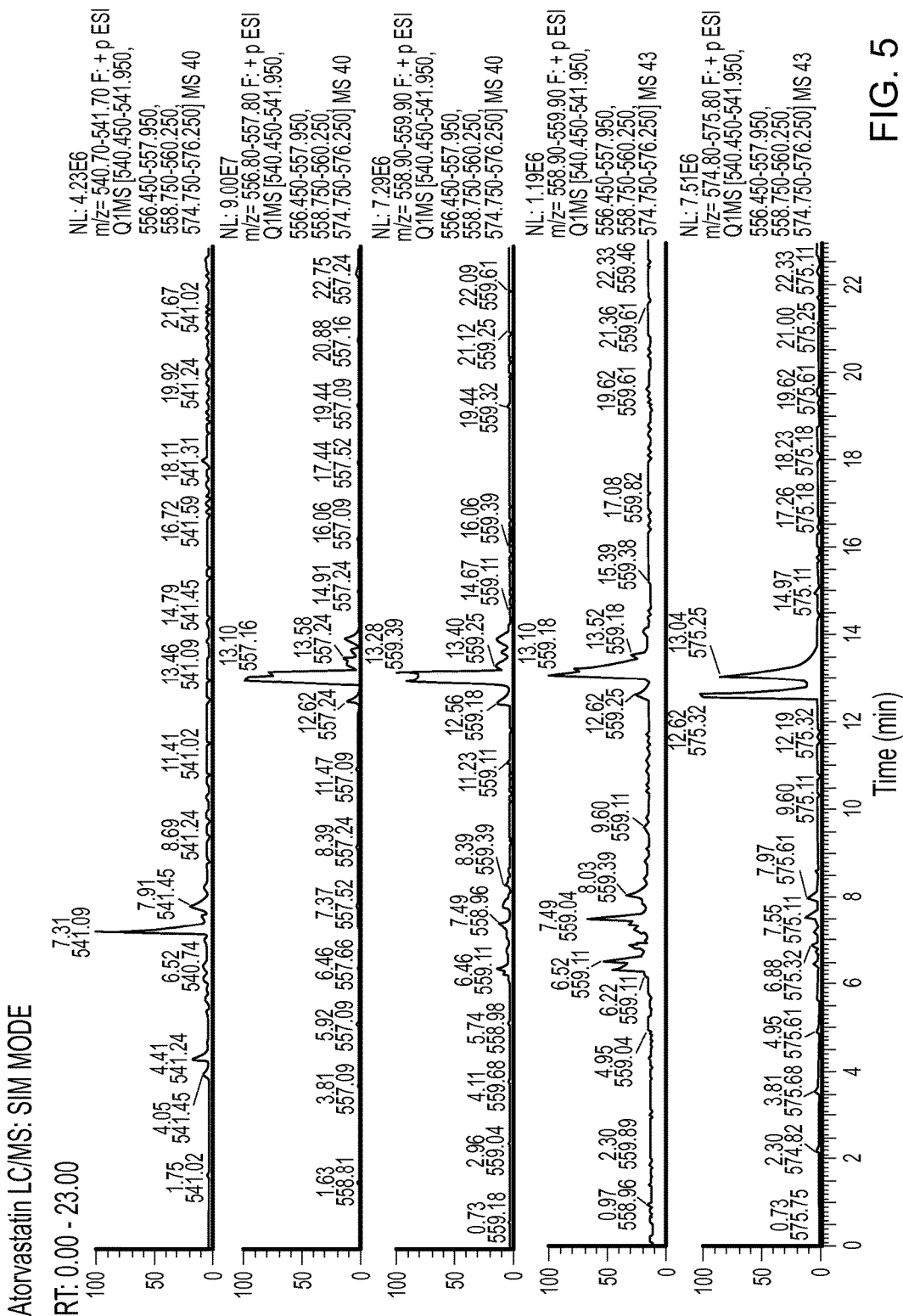
FIG. 5 is a representative MS-SIM chromatogram demonstrating representative atorvastatin metabolites produced following microwave reaction in the presence of Octabromo tetrakis(2,6-dichlorophenyl)porphyrin Fe(III)Cl.

Identification of atorvastatin metabolites following optimal microwave reaction in the presence of Octabromo tetrakis(2,6-dichlorophenyl)porphyrin Fe(III)Cl are provided in Table 5 and FIG. 5.

TABLE 5

Atorvastatin Microwave Results:

| Spec. Reference | Scan Range: Respective Metabolite | MS MODE | Optimal µwave Conditions | Retention Time (min) |
|---|---|---|---|---|
| 1 | m/z 540.70 → 541.70: ATR lactone | SIM | 80° C., 50 min | 7.31 |
| 2 | m/z 556.80 → 557.80: ATR acid (API) | SIM | N/A | 13.10 |
| 3 | m/z 558.90 → 559.90: o/p-Hydroxy lactone | SIM | 80° C., 30 min | 13.28 |
| 4 | m/z 558.90 → 559.90: o/p-Hydroxy lactone | | 80° C., 50 min | 7.49 |
| 5 | m/z 574.80 → 575.80: o/p-Hydroxy acid | SIM | 80° C., 30 min | 12.62 |
| 5 | m/z 574.80 → 575.80: o/p-Hydroxy acid | | | 13.04 |

Atorvastatin Metabolite Structures:

| Compound | Structure |
|---|---|
| Atorvastatin Lactone Chemical Formula: $C_{33}H_{33}FN_2O_4$ Exact Mass: 540.2424 | 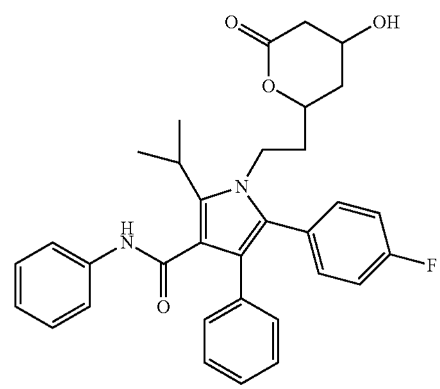 [SMILES: CC(C)c1c(C(=O)Nc2ccccc2)c(-c2ccccc2)c(-c2ccc(F)cc2)n1CCC1CC(O)CC(=O)O1] |
| Atorvastatin Acid Chemical Formula: $C_{33}H_{35}FN_2O_5$ Exact Mass: 558.2530 | 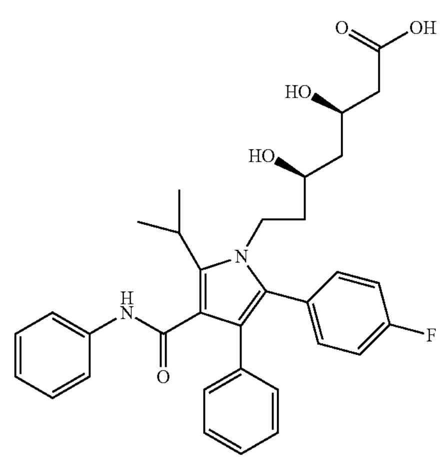 [SMILES: CC(C)c1c(C(=O)Nc2ccccc2)c(-c2ccccc2)c(-c2ccc(F)cc2)n1CC[C@@H](O)C[C@@H](O)CC(=O)O] |

-continued

| Compound | Structure |
|---|---|
| ortho-Hydroxy Lactone<br>Chemical Formula: $C_{33}H_{33}FN_2O_5$<br>Exact Mass: 556.2374 | |
| para-Hydroxy Lactone<br>Chemical Formula: $C_{33}H_{33}FN_2O_5$<br>Exact Mass: 556.2374 | |
| ortho-Hydroxy Acid<br>Chemical Formula: $C_{33}H_{35}FN_2O_6$<br>Exact Mass: 574.2479 | |
| para-Hydroxy Lactone<br>Chemical Formula: $C_{33}H_{35}FN_2O_6$<br>Exact Mass: 574.2479 | |

Example 6. Rosuvastatin Microwave Protocol

Rosuvastatin API (40.0 mg, 0.08307 mmol) extracted using 80 mL 1:1 methanol:ethanol, filtered and concentrated in vacuo. The resulting solid taken up in 2:0.5 mL acetonitrile:water and transferred to a microwave tube. Octabromo tetrakis(2,6-dichlorophenyl)porphyrin Fe(III)Cl (6.69 mg, 0.00415 mmol) then added, followed by sodium hypochlorite (102.5 uL, 0.20767 mmol). Reaction run in the microwave at 80° C. for 50 minutes. (representative, see table below for additional conditions).

Workup: Reaction diluted with 40 mL chloroform. Washed 3×40 mL water. Washed 3×40 mL brine. Back-extracted aqueous layer with 40 mL chloroform. Organic layers combined and dried over MgSO4, filtered and concentrated in vacuo. Samples analyzed according to parameters provided in Example 1.

Figure 6:
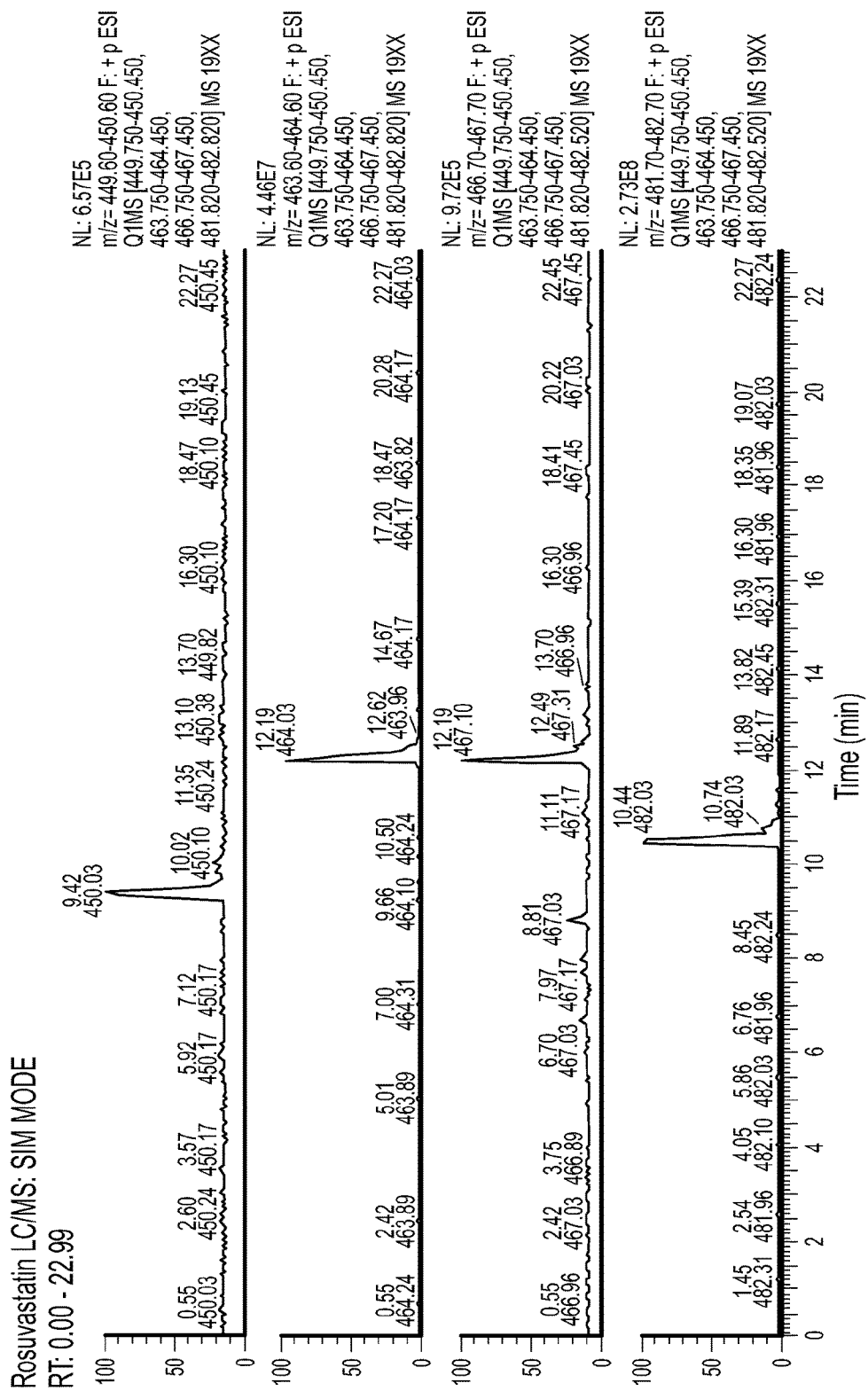
FIG. 6 is a representative MS-SIM chromatogram demonstrating representative rosuvastatin metabolites produced following microwave reaction in the presence of Octabromo tetrakis(2,6-dichlorophenyl)porphyrin Fe(III)Cl.

Identification of rosuvastatin metabolites following optimal microwave reaction in the presence of Octabromo tetrakis(2,6-dichlorophenyl)porphyrin Fe(III)Cl are provided in Table 6 and FIG. 6.

TABLE 6

Rosuvastatin Microwave results:

| Spec. Reference | Scan Range: Respective Metabolite | MS MODE | Optimal μwave Conditions | Retention Time (min) |
|---|---|---|---|---|
| 4 | m/z 481.70 → 482.70: Rosuvastatin Acid | SIM | N/A | 10.44 |
| 3 | m/z 466.70 → 467.70: Desmethyl-Acid | SIM | 80° C., 30 min | 12.19 |
| 2 | m/z 463.60 → 464.60: Rosuvastatin Lactone | SIM | 80° C., 50 min | 12.19 |
| 1 | m/z 449.60 → 450.60: Desmethyl-Lactone | SIM | 80° C., 10 min | 9.42 |

Rosuvastatin Metabolite Structures:

| Compound | Structure |
|---|---|
| Rosuvastatin acid<br>Chemical Formula: $C_{22}H_{28}FN_3O_6S$<br>Exact Mass: 481.17 | |
| Desmethyl-rosuvastatin acid<br>Chemical Formula: $C_{21}H_{26}FN_3O_6S$<br>Exact Mass: 467.15 | |

| Compound | Structure |
|---|---|
| Rosuvastatin lactone<br>Chemical Formula:<br>$C_{22}H_{26}FN_3O_5S$<br>Exact Mass:<br>463.16 | 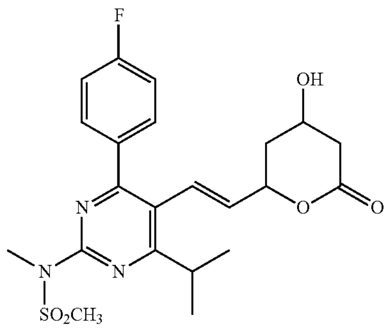 [SMILES: CC(C)c1nc(N(C)S(C)(=O)=O)nc(-c2ccc(F)cc2)c1/C=C/C1CC(O)CC(=O)O1] |
| Desmethyl-rosuvastatin lactone<br>Chemical Formula:<br>$C_{21}H_{24}FN_3O_5S$<br>Exact Mass:<br>449.14 | 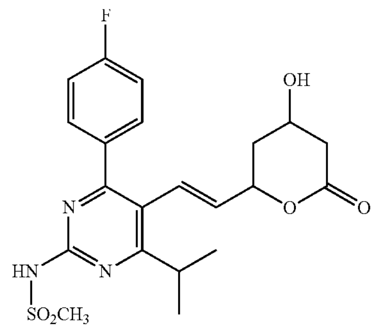 [SMILES: CC(C)c1nc(NS(C)(=O)=O)nc(-c2ccc(F)cc2)c1/C=C/C1CC(O)CC(=O)O1] |

Example 7. Simvastatin Microwave Protocol

Figure 7:
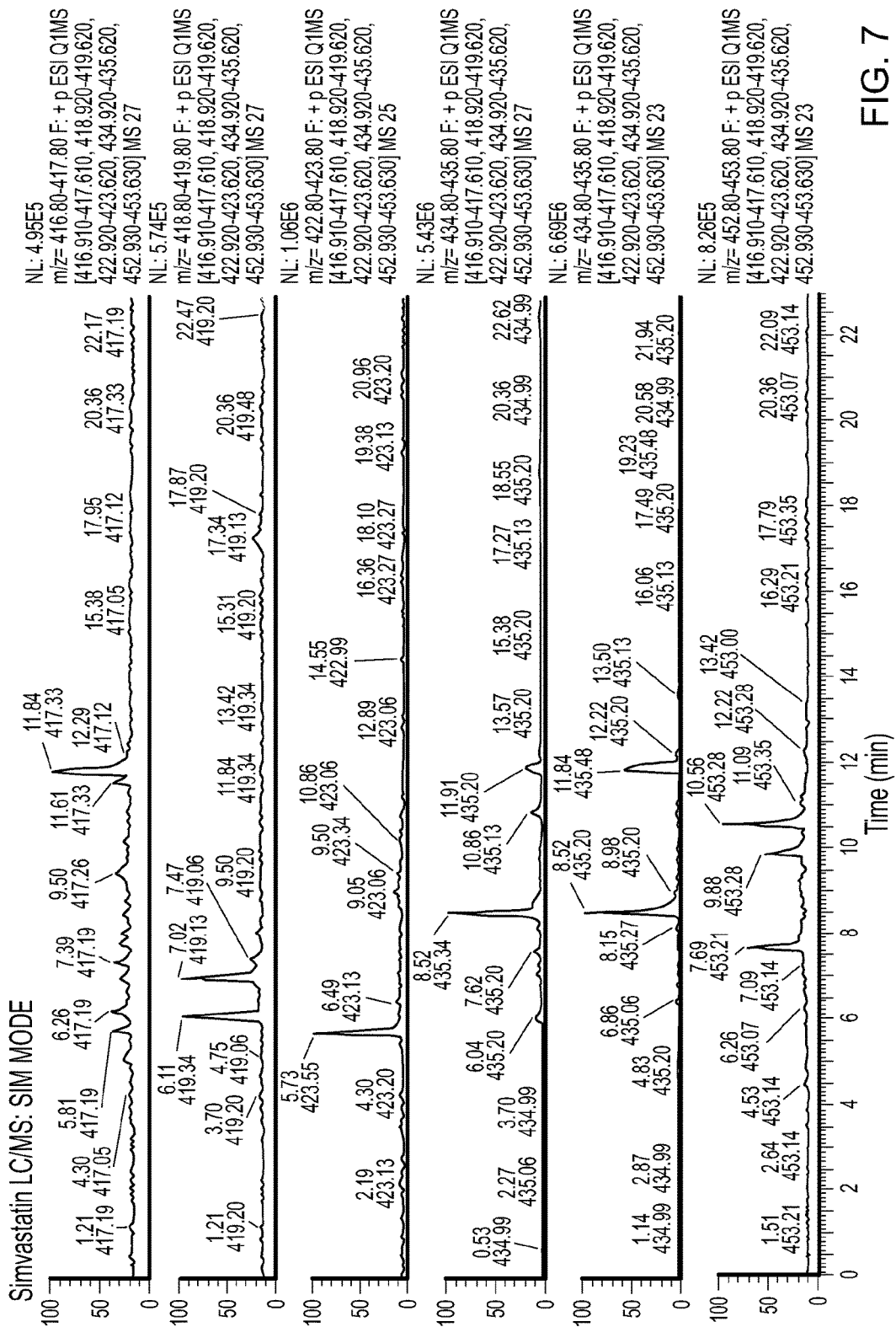
FIG. 7 is a representative MS-SIM chromatogram demonstrating representative simvastatin metabolites produced following microwave reaction in the presence of Octabromo tetrakis(2,6-dichlorophenyl)porphyrin Fe(III)Cl.

Simvastatin API (40.0 mg, 0.09556 mmol) extracted using 80 mL 1:1 methanol:ethanol, filtered and concentrated in vacuo. The resulting solid taken up in 2:0.25 mL acetonitrile:water and transferred to a microwave tube. Octabromo tetrakis(2,6-dichlorophenyl)porphyrin Fe(III)Cl (7.70 mg, 0.00478 mmol) then added, followed by sodium hypochlorite (118 uL, 0.2389 mmol). Reaction run in the microwave at 80° C. for 50 minutes. (representative, see table below for additional conditions).
Workup: Reaction diluted with 40 mL chloroform. Washed 3×40 mL water. Washed 3×40 mL brine. Back-extracted aqueous layer with 40 mL chloroform. Organic layers combined and dried over MgSO4, filtered and concentrated in vacuo. Samples analyzed according to parameters in Example 1.
Identification of simvastatin metabolites following optimal microwave reaction in the presence of Octabromo tetrakis(2,6-dichlorophenyl)porphyrin Fe(III)Cl are provided in Table 7 and FIG. 7.

TABLE 7

| Spec. Reference | Scan Range: Respective Metabolite | MS MODE | Optimal µwave Conditions | Retention Time (min) |
|---|---|---|---|---|
| 1 | m/z 416.80 → 417.80: 6'-Exomethylene SV | SIM | 80° C., 10 min | 11.84 |
| 2 | m/z 418.80 → 419.90: Simvastatin (SV) | SIM | N/A | 0.11 |
| 3 | m/z 422.80 → 423.80: Simvastatin Acid (SVA) | SIM | 80° C., 30 min | 5.73 |
| 4 | m/z 434.80 → 435.80: 6' β-Hydroxy SV | SIM | 80° C., 10 min | 11.84 |
| 5 | m/z 434.80 → 435.80: 3'-Hydroxy SV | SIM | 80° C., 50 min | 8.52 |
| 6 | m/z 452.80 → 453.80: 3',5'-Diohydrodiol SV | SIM | 80° C., 50 min | 7.69 |

Simvastatin Metabolite Structures:

| Compound | Structure |
|---|---|
| 6'-Exo-methylene SV<br>Chemical Formula:<br>$C_{25}H_{36}O_5$<br>Exact Mass:<br>416.2563 | 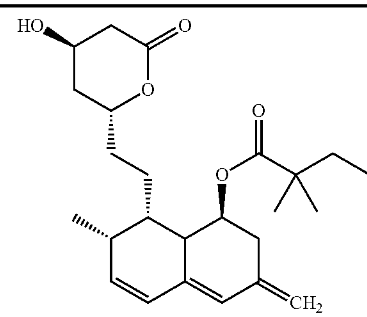 |
| Simvastatin (SV)<br>Chemical Formula:<br>$C_{25}H_{38}O_5$<br>Exact Mass:<br>418.2719 | 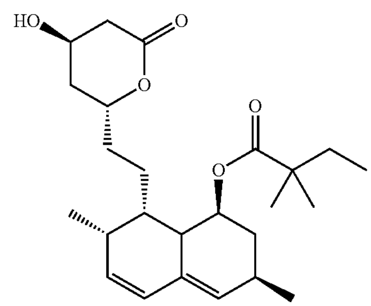 [SMILES: CCC(C)(C)C(=O)O[C@H]1C[C@@H](C)C=C2C=C[C@H](C)[C@H](CC[C@@H]3C[C@@H](O)CC(=O)O3)C21] |
| Simvastatin Acid (SVA)<br>Chemical Formula:<br>$C_{24}H_{38}O_6$<br>Exact Mass:<br>422.2668 | 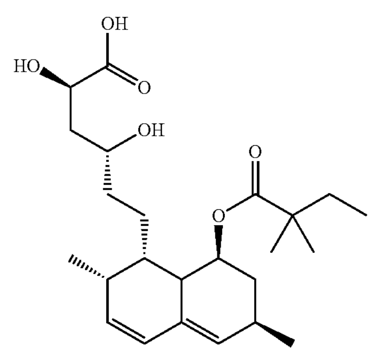 [SMILES: CCC(C)(C)C(=O)O[C@H]1C[C@@H](C)C=C2C=C[C@H](C)[C@H](CC[C@@H](O)C[C@@H](O)C(=O)O)C21] |
| 6'β-Hydroxy SV<br>Chemical Formula:<br>$C_{25}H_{38}O_6$<br>Exact Mass:<br>434.2668 | 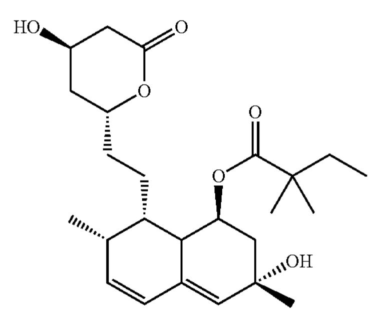 [SMILES: CCC(C)(C)C(=O)O[C@H]1C[C@](C)(O)C=C2C=C[C@H](C)[C@H](CC[C@@H]3C[C@@H](O)CC(=O)O3)C21] |

| Compound | Structure |
|---|---|
| 3'-Hydroxy SV<br>Chemical Formula:<br>$C_{25}H_{38}O_6$<br>Exact Mass:<br>434.2668 | (structure) |
| 3',5'-Dihydrodiol SV<br>Chemical Formula:<br>$C_{25}H_{40}O_7$<br>Exact Mass:<br>452.2774 | (structure) |

Example 8. Saxagliptin Microwave Protocol

Saxagliptin API (20.0 mg, 0.06341 mmol) extracted using 50 mL 1:1 methanol:ethanol, filtered and concentrated in vacuo. The resulting solid taken up in 2:0.25 mL acetonitrile:water and transferred to a microwave tube. Octabromo tetrakis(2,6-dichlorophenyl)porphyrin Fe(III)Cl (5.11 mg, 0.003171 mmol) then added, followed by sodium hypochlorite (78.3 uL, 0.1585 mmol). Reaction run in the microwave at 80° C. for 50 minutes. (representative, see table below for additional conditions).

Workup: Reaction diluted with 40 mL chloroform. Washed 3×40 mL water. Washed 3×40 mL brine. Back-extracted aqueous layer with 40 mL chloroform. Organic layers combined and dried over MgSO4, filtered and concentrated in vacuo. Samples analyzed according to parameters in Example 1.

Figure 8A:
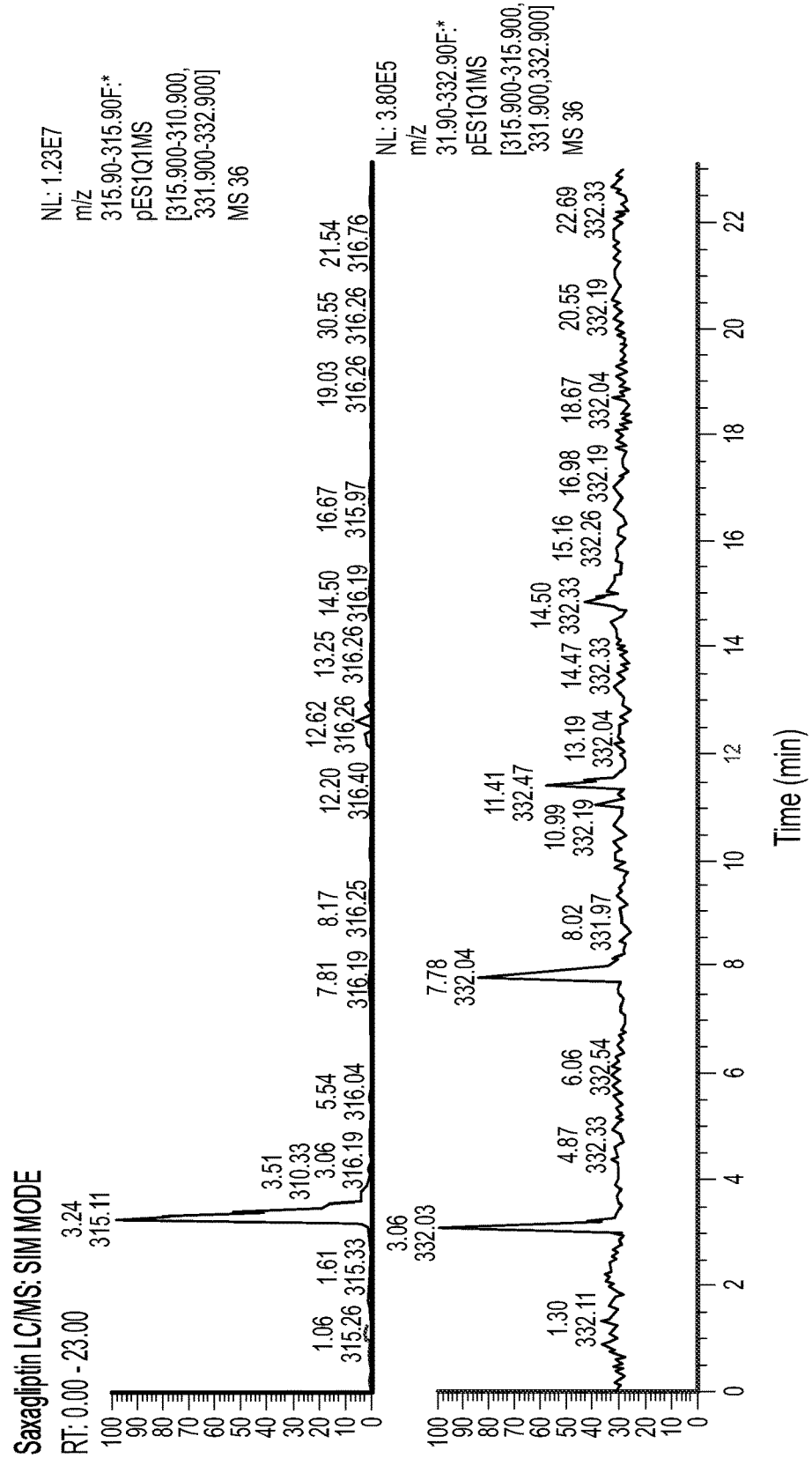
FIGS. 8A and 8B a is a representative MS-SIM (8A) and MS-SRM (8B) chromatogram demonstrating representative saxagliptin metabolites produced following microwave reaction in the presence of Octabromo tetrakis(2,6-dichlorophenyl)porphyrin Fe(III)Cl.
Figure 8B:
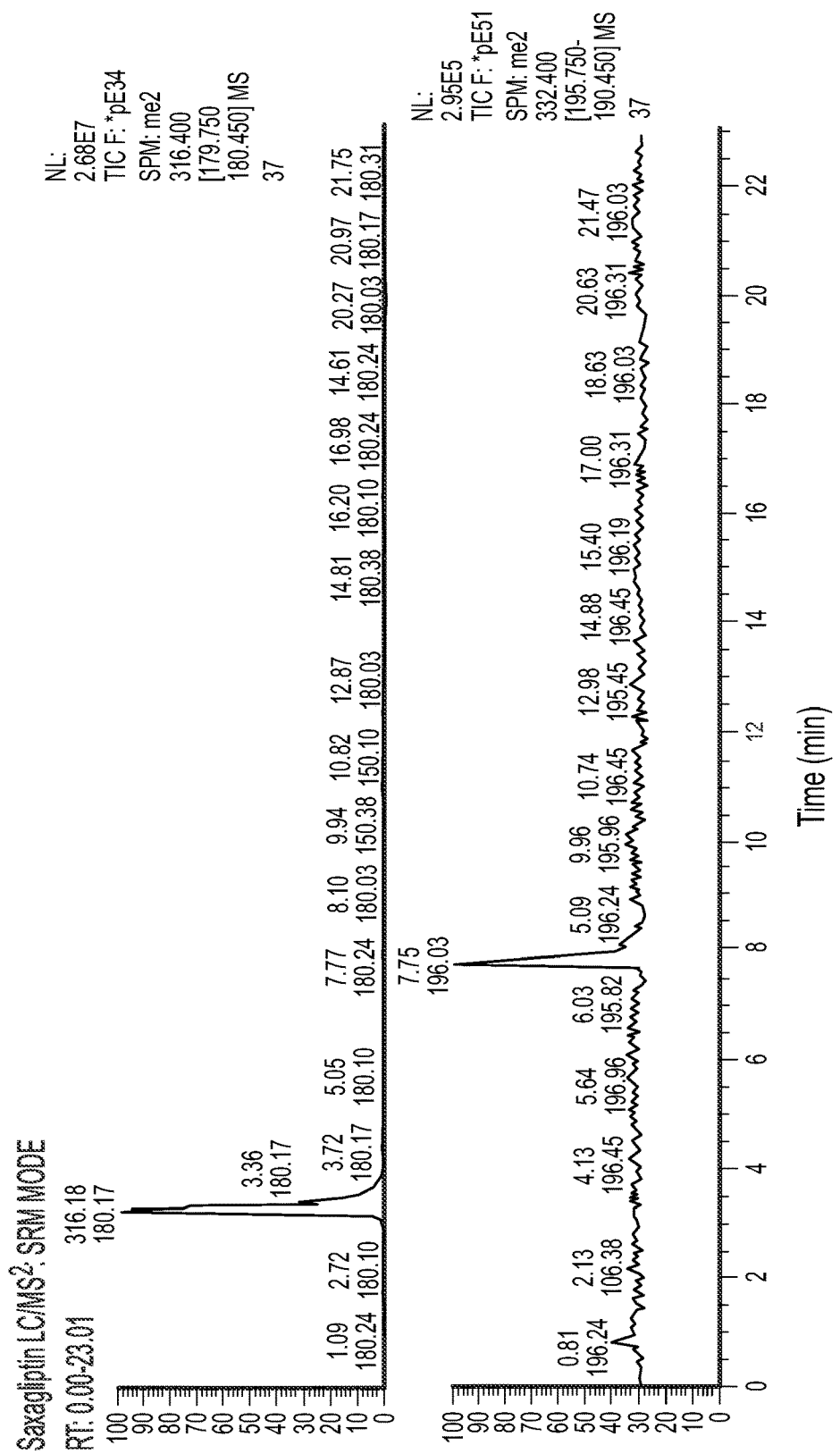

Identification of saxagliptin metabolites following optimal microwave reaction in the presence of Octabromo tetrakis(2,6-dichlorophenyl)porphyrin Fe(III)Cl are provided in Table 8 and FIG. 8.

TABLE 8

Saxagliptin Microwave Results:

| Spec. Reference | Scan Range: Respective Metabolite | MS MODE | Optimal µwave Conditions | Retention Time (min) |
|---|---|---|---|---|
| 1 | m/z 315.90→ 316.90: Saxagliptin | SIM | N/A | 3.24 |
| 2 | [ms² 316.400] m/z 179.75→ 180.45 | SRM | N/A | 3.06 |
| 3 | m/z 331.90→ 332.90: SAX1 | SIM | 80° C., 50 min. | 7.78 |
| 4 | [ms² 332.400] m/z 195.75→ 196.45 | SRM | 80° C., 50 min. | 7.78 |

Saxagliptin Metabolite Structures:

| Compound | Structure |
|---|---|
| Saxagliptin<br>Chemical Formula:<br>$C_{18}H_{25}N_3O_2$<br>Exact Mass:<br>315.19 | (structure) |
| SAX1<br>Chemical Formula:<br>$C_{18}H_{25}N_3O_3$<br>Exact Mass:<br>331.19 | (structure) |
| SAX1-rearrangement<br>Chemical Formula:<br>$C_{18}H_{25}N_3O_3$<br>Exact Mass:<br>331.19 | (structure) |

Example 9. Pioglitazone Microwave Protocol

A solution of Pioglitazone hydrochloride (20.0 mg, 0.05611 mmol) in 1:0.25 mL acetonitrile:water treated with potassium carbonate (11.63 mg, 0.08415) and left to stir for 30 minutes. Octabromo tetrakis(2,6-dichlorophenyl)porphyrin Fe(III)Cl (4.52 mg, 0.00281 mmol) was then added, followed by sodium hypochlorite (69.2 uL, 0.14028 mmol). Reaction run in the microwave at 80° C. for 50 minutes. (representative, see table below for additional conditions).

Workup: Reaction diluted with 40 mL chloroform. Washed 3×40 mL water. Washed 3×40 mL brine. Back-extracted aqueous layer with 40 mL chloroform. Organic layers combined and dried over MgSO4, filtered and concentrated in vacuo. Samples analyzed according to parameters in Example 1.

Figure 9A:
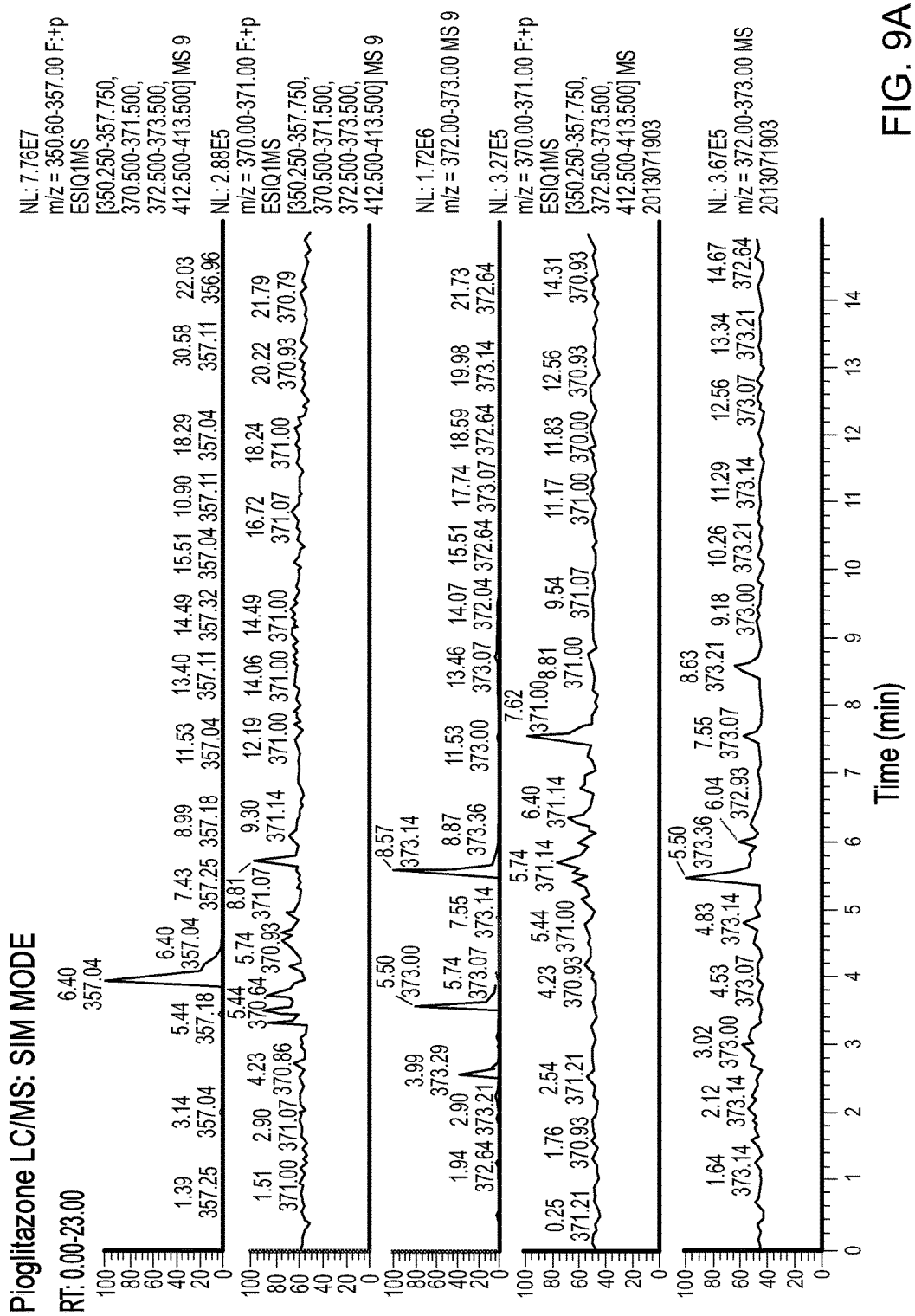
FIGS. 9A and 9B a representative MS-SIM (9A) and MS-SRM (9B) chromatograms demonstrating representative pioglitazone metabolites produced following microwave reaction in the presence of Octabromo tetrakis(2,6-dichlorophenyl)porphyrin Fe(III)Cl.
Figure 9B:
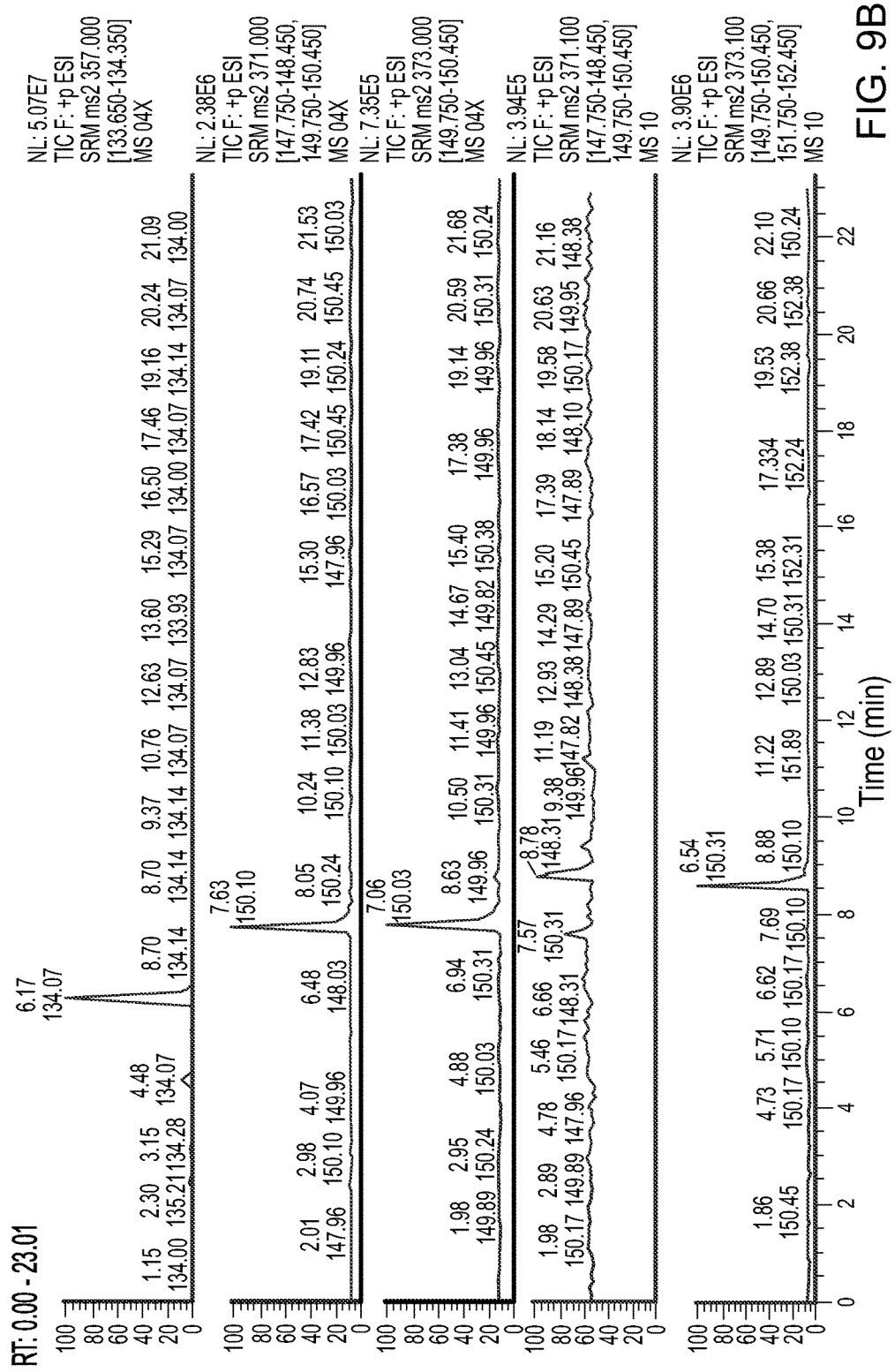

Identification of pioglitazone metabolites following optimal microwave reaction in the presence of Octabromo tetrakis(2,6-dichlorophenyl)porphyrin Fe(III)Cl are provided in Table 9 and FIG. 9.

TABLE 9

Pioglitazone Microwave results:

| Spec. Reference | Scan Range: Respective Metabolite | MS MODE | Optimal μwave Conditions | Retention Time (min) |
|---|---|---|---|---|
| 1 | m/z 356.60→ 357.60: Pioglitazone | SIM | N/A | 6.17 |
| 6 | [ms² 357.000] m/z 133.650→ 134.350 | SRM | N/A | 6.17 |
| 4 | m/z 370.60→ 371.60: 2/9-Carbonyl PIO | SIM | 80° C., 50 min; 80° C., 10 min | 7.61; 8.81 |
| 2 7 | [ms² 371.100] | SRM | 80° C., 50 min; | 7.63; |
| 9 | m/z 149.750→ 150.450 | | 80° C., 10 min | 8.78 |
| 5 | m/z 372.30→ 373.30: 2/9-Hydroxy PIO | SIM | 80° C., 50 min; 80° C., 10 min | 7.55; 8.57 |
| 3 8 | [ms² 373.100] | SRM | 80° C., 50 min; | 7.66; |
| 10 | m/z 149.750→ 150.450 | | 80° C., 10 min | 8.58 |

Pioglitazone Metabolite Structures:

| Compound | Structure |
|---|---|
| Pioglitazone (PIO) Chemical Formula: $C_{19}H_{20}N_2O_3S$ Exact Mass: 356.12 | |
| 2-Carbonyl PIO Chemical Formula: $C_{19}H_{18}N_2O_4S$ Exact Mass: 370.10 | |
| 9-Carbonyl PIO Chemical Formula: $C_{19}H_{18}N_2O_4S$ Exact Mass: 370.10 | |
| Pioglitazone Acid Chemical Formula: $C_{18}H_{16}N_2O_5S$ Exact Mass: 372.08 | |
| 2-Hydroxy PIO Chemical Formula: $C_{19}H_{20}N_2O_4S$ Exact Mass: 372.11 | |
| 9-Hydroxy PIO Chemical Formula: $C_{19}H_{20}N_2O_4S$ Exact Mass: 372.11 | |

Example 10

Materials:

Pioglitazone hydrochloride and metformin hydrochloride were obtained from Cipla Ltd., Mumbai Central Mumbai 400 008 India. The oxidants were obtained from the following: hydrogen peroxide, 50% (Fisher Scientific), sodium Hypochlorite, 12.5% available chlorine (Sigma-Aldrich), iodosylbenzene (synthesized by standard literature methods). The two metalloporphyrin catalysts, octabromo tetrakis(2,6-dichlorophenyl)porphyrin Fe(III)Cl and octachloro tetrakis(2,6-dichlorophenyl)porphyrin Fe(III)Cl were obtained synthetically by collaborators in India.

Synthesis of Pioglitazone Metabolites:

Pioglitazone hydrochloride (50.0 mg, 0.1403 mmol) in a CHCl3/H2O mixture (9:1) was treated with potassium carbonate (24.25 mg, 0.1754 mmol) and stirred for 30 minutes. At this time, the metalloporphyrin catalyst (8.80 mg, 0.00702 mmol) and the oxidant (1.25 eq.) were added. The reaction was brought to 45° C. and stirred for 2 hours, at which time an additional 1.25 eq. of oxidant was added and the mixture was left to stir at 45° C. overnight. The reaction was cooled to 25° C. and diluted with CHCl$_3$ (40 mL). The mixture was washed with 1120 (3×) and brine (3×), and the aqueous layers were back-extracted with 3:1 CHCl$_3$/IPA (3×). Organic phases were combined, dried (MgSO4), and concentrated in vacuo. The excess porphyrin was removed by alumina oxide chromatography (1:1 EtOAc/Hexanes→4:1 MeOH/DCM). The remaining reaction mixture was concentrated and prepared for analysis crude.

Synthesis of Metformin Metabolites:

Metformin hydrochloride (50.0 mg, 0.3871 mmol) in a CH$_3$CN/H2O mixture (9:1) was treated with potassium carbonate (66.9 mg, 0.4839 mmol) and stirred for 30 minutes. At this time, the metalloporphyrin catalyst (5 mol %) and the oxidant (1.25 eq) were added. The reaction was brought to 45° C. and stirred for 2 hours, at which time an additional 1.25 eq. of oxidant was added and the mixture was left to stir at 45° C. overnight. The reaction was cooled to 25° C. and diluted with CHCl3 (40 mL). The mixture was washed with H$_2$O (3×) and brine (3×), and the aqueous layers were back-extracted with 3:1 CHCl3/IPA (3×). Organic phases were combined, dried (MgSO4), and concentrated in vacuo. The excess porphyrin was removed by alumina oxide chromatography (1:1 EtOAc/Hexanes→4:1 MeOH/DCM). The remaining reaction mixture was concentrated and prepared for analysis crude.

Synthesis of Atorvastatin Metabolites:

Atorvastatin (40.0 mg, 0.0735 mmol) in a CHCl$_3$/H2O mixture (9:1) was treated with the metalloporphyrin catalyst (5 mol %) and the oxidant (1.25 eq) were added. The reaction was brought to 45° C. and stirred for 2 hours, at which time an additional 1.25 eq. of oxidant was added and the mixture was left to stir at 45° C. overnight. The reaction was cooled to 25° C. and diluted with CHCl$_3$ (40 mL). The mixture was washed with H$_2$O (3×) and brine (3×), and the aqueous layers were back-extracted with 3:1 CHCl$_3$/IPA (3×). Organic phases were combined, dried (MgSO4), and concentrated in vacuo. The excess porphyrin was removed by alumina oxide chromatography (1:1 EtOAc/Hexanes→4:1 MeOH/DCM). The remaining reaction mixture was concentrated and prepared for analysis crude.

Thin layer chromatography showed 4 products by UV-Vis with Rf-values too close for traditional silica column chromatography, LC-MS methods currently being developed for separation of products. (data not shown)

Experimental Design for Metabolite Identification (1) Pioglitazone Method—Reverse Phase HPLC Crude reaction mixture was diluted to a concentration of approximately 5 mg/mL in chloroform. For LC-MS/MS analysis, 25 μL of the 5 mg/mL sample was diluted in 975 μL 10:90 acetonitrile:water mobile phase. The LC analysis was done using an Agilent 1100 LC equipped with binary pump and diode array detector. Twenty five microliters of sample was injected into a 2.1×50 mm Thermo Accucore C18 HPLC column with a 2.6 μm particle size running at 500 μL/min. Mobile phase A was 0.1% formic acid in water and mobile phase B was 0.1% formic acid in acetonitrile. A linear gradient from 10%-90% B was run over 10 minutes. The DAD was set to monitor 254 and 280 nm as well as collecting all wavelengths between 190-400 nm for spectral analysis.

The MS/MS analysis was done using a Thermo LCQ Deca XP Plus 3D linear ion trap operated in positive ion mode. The electrospray voltage was 3.5 kV and the desolvation gas was set to 40 arbitrary units. The system was operated in several different modes to confirm the presence and identity of the metabolite. Selective ion monitoring mode (SIM) was used to quickly identify known metabolites of pioglitazone in the crude reaction mixture based on the molecular weight and retention time data reported in the literature for known metabolites of pioglitazone. Selective reaction monitoring (SRM) was used to confirm the identifications in SIM by detecting unique fragment ions derived from the MS/MS of the known metabolites and matched to literature reports. Data dependent MS/MS mode was used to collect fragmentation data on unknown metabolites. Interpretation of this data is ongoing.

(2) Metformin Method—Hydrophobic Interaction Lipophilic Interaction Chromatography (HILIC)

Crude reaction mixture was diluted to a concentration of approximately 5 mg/mL in chloroform. For LC-MS/MS analysis, 25 μL of the 5 mg/mL sample was diluted in 975 μL 95:5 acetonitrile:15 mM ammonium acetate mobile phase. The LC analysis was done using an Agilent 1100 LC equipped with binary pump and diode array detector. Twenty five microliters of sample was injected into a 2.1×100 mm Higgs Analytical CLIPEUS Silica column with 5.0 μm particle size running at 1 mL/min. Mobile phase A was 15 mM ammonium acetate in water and mobile phase B was 100% acetonitrile. The method was held at 5:95 A:B for 2 minutes then a linear gradient from 95-75% B was run over 15 minutes and then from 75-50% B over 3 minutes. The DAD was set to monitor 228, 230, 254 and 280 nm as well as collecting all wavelengths between 190-400 nm for spectral analysis. The metformin showed very good retention (retention time of ~7.5 minutes) for this method and allowed for the separation of several peaks during the chromatographic run.

The MS/MS analysis was done using a Thermo LCQ Deca XP Plus 3D linear ion trap operated in positive ion mode. The electrospray voltage was 3.5 kV and the desolvation gas was set to 40 arbitrary units. The system was operated in both full scan MS mode (50-350 m/z mass range) and data dependent MS/MS modes. Data dependent MS/MS mode was used to collect fragmentation data on unknown metabolites. As there is no published literature on the metabolites of metformin, interpretation of this data will require subsequent analysis on the Thermo XL Orbitrap which is ongoing.

Results:

LC-MS/MS method showed presence of metabolite [M+1] 373 (1) at retention time 1.10, as well as metabolite [M+1] 371 (11) at retention time 1.95.

Example 11

Experimental Design

Seven groups (21 total samples—see table below) of $K_2$EDTA blank human plasma samples were spiked with the drugs of interest, their combinations and with (OCOBFe)-Meso-tetrakis (2, 6-dichloro phenyl)-β-octabromo porphinato Iron complex. These reaction products were analyzed by simultaneous monitoring for multiple metabolite formation (metabolites fingerprinting) and for formation of known metabolites by LC/MS/MS.

Stock solutions of metformin and atorvastatin were prepared in $K_2$EDTA blank human plasma as shown in Table 10.

TABLE 10

| SS-M | metformin | 20.0 μg/mL |
|---|---|---|
| SS-A | atorvastatin | 2.0 μg/mL |
| SS-MA | metformin & atorvastatin | Combine equal amount of SS-M and SS-A (1:1 dilution) |

Stock solutions of the OCOBFe and Tetra n-butyl ammonium bromide (TBAB) are prepared as shown in Table 11.

TABLE 11

| SS-BC Meso-tetrakis (2,6-dichloro phenyl)-β-octabromo porphinato Iron complex | 1.0 μg/mL | OCOBFe is prepared in 1:1 mixture Acetonitrile (ACN) and Ethyl Acetate (EA). |
|---|---|---|
| SS-BCO 4%-5% NaOCl, in $H_2O$ | 4%-5% | Bleach solution |
| SS-TBAB | 1.0 μg/mL | Tetra n-butyl ammonium bromide (TBAB) is prepared in 1:1 mixture Acetonitrile (ACN) and Ethyl Acetate (EA). |

Typical Biomimics Catalyst assay procedure to 100 μL of blank plasma or test article plasma sample add 10.0 μL catalyst stock solution (SS-BC), 5.0 μL Phase Transfer Catalyst (SS-TBAB) and 10.0 μL of Co-oxidant (SS-BCO)
  Vortex for ~1-3 min
  Incubate at RT for 60 min
  Quench with 800 μL of ACN
  Vortex for ~1 min
  Centrifuge >5,000 rpm for 20 min at RT
  Remove supernatant into clean plate/tube
  Proceed with LC/MS analysis of organic fraction*
*To achieve desired chromatographic and/or LC/MS resolution and sensitivity, samples may require drying and reconstitution with appropriate amount of the mobile phase.

The Sample preparation and analysis scheme is provided in Table 12 below.

TABLE 12

| Test article | Samples (n) | SS-M (μL) | SS-L (μL) | SS-ML (μL) | SS-BC (μL) | SS-BCO (μL) | SS-TBAB (μL) | Blank (HP) (μL) |
|---|---|---|---|---|---|---|---|---|
| Blank plasma | 3 | — | — | — | — | — | — | 125 |
| Metformin free base | 3 | 50 | — | — | — | — | — | 75 |
| Atorvastatin | 3 | — | 50 | — | — | — | — | 75 |
| Metformin free base & Atorvastatin | 3 | — | — | 100 | — | — | — | 25 |
| Metformin free base | 3 | 50 | — | — | 10 | 10 | 5 | 25 |
| Atorvastatin free base | 3 | — | 50 | — | 10 | 10 | 5 | 25 |
| Metformin free base & Atorvastatin | 3 | — | — | 100 | 10 | 10 | 5 | — |

The goal of this study was to provide LC/MS/MS characterization for the samples described above. In-line UV detection was monitored simultaneously. Analytical methods included initial analysis by full mass scan and follow up analysis with multiple reaction monitoring (MRM) of known/predicted metabolites.

The results presented by overlaying the fingerprint profiles (total ion chromatograms, TICs) with the corresponding catalyst assay profiles on identical scales (e.g., scale to the highest peak). Indications of suppression and/or attenuation of metabolism of one drug in the presence of the other were determined by comparing the area count of individual peaks of the catalyst assay to the corresponding peaks of the actual metabolic profiles and/or selective known metabolites. Mass Spec parent ions and fragmentation patterns were studied as follows: Molecular ion for peaks ascertained, but not in the controls or blank 2) Synopsis of analytical conditions 3) Tabular summation of chromatographic and MS data (retention time, molecular ion and proposed transformation 4) Representative chromatograms and mass spectra 5) Proposed transformations and structures of metabolites, as applicable. Results are shown in FIGS. 12 to 17.

Example 12. Microwave Assisted Synthesis of Metalloporphyrins

It has been shown that the electronically activated and sterically hindered metalloporphyrins disclosed herein can be synthesized rapidly and efficiently by metal insertion into a free porphyrin ring by heating the free base in the presence of a metal source under conventional microwave at low temperature, e.g., 750 W microwave at microwave frequency of 2450 MHz, or 750 W microwave at microwave frequency of 2.45 GHz". Previously metalized derivatives of the porphyrins had a flat and planar ring, where insertion is a facile process. The sterically hindered, electronically activated porphyrins used herein as catalysts, have a saddle-shaped puckered ring system; this puckering eliminates the planar central cavity and makes the deformed ring more difficult to metallate. Moreover, the electronic activation conferred on the ring has one additional problem related to metal insertion. Previously, insertion of metals such as Ru, Rh etc., in extended reflux in a very high boiling solvent such as decane, decalin and xylene was unsuccessful. This process resulted in poor yield, as the Ru salt, serving as a Lewis acid and electrophile, methodically abstracted the halogens one after the other, degrading the compound to the tetraphenyl porphyrin. Using microwave energy insertion of Ru into a highly puckered core proceeds rapidly and with high yields.

Reaction of 4-Amino TPP with RuCl$_3$ Using Microwave Energy According to the Following Reaction:

The free base 4-amino TPP (0.025 g; 0.074 mmol), RuCl$_3$·6H$_2$O (0.009 g; 0.74 mmol), and Decalin (10 mL) were irradiated under domestic microwave at low temperature. The microwave operated at 230 V at ca. 50 Hz and produced a maximum microwave power output of 750 W at a microwave frequency of 2450 MHz. The progress of the reaction was monitored by TLC. Metal insertion was completed in 20 minutes. The reaction mixture was quenched in water and 100 ml and solid was separated out, filtered and dried to obtain 0.025 g of crude, 10,15,20-(4-amino)tetraphenylporphynato Ru(III) Chloride (4-amino Ru TPP). Formation of (4-amino Ru(III) TPP was confirmed by UV-VIS spectra (λ 428, 517, 560, 656, 762 nm).

Synthesis of 5, 10, 15, 20-(4-amino)tetraphenylporphynato Rh(III) Chloride (4-Amino Rh(III) TPP)

The title compound was prepared by reaction of 4-amino TPP with RhCl$_3$ using microwave energy according to the following reaction:

The free base 4-amino TPP (0.025 g; 0.074 mmol), RhCl3-6H2O (0.009 g; 0.74 mmol), and decalin (decahydronapthalene) (10 mL) were irradiated in domestic microwave at low temperature. The microwave operated at 230 V at ca. 50 Hz and produced a maximum microwave power output of 750 W at a microwave frequency of 2450 MHz. The progress of the reaction was monitored by TLC. Metal insertion was completed in 20 minutes. The reaction mixture was quenched in water and 50 ml and solid was separated out, filtered and dried to obtain 0.020 g of crude 5,10,15,20-(4-amino)tetraphenylporphynato Rh(II) Chloride (4-amino Rh TPP). Formation of 4-amino Rh TPP was confirmed by UV-VIS spectra (λ 432.5, 738 nm).

Preparation of Octachloro Octachloro Ruthenium (III) Chloride

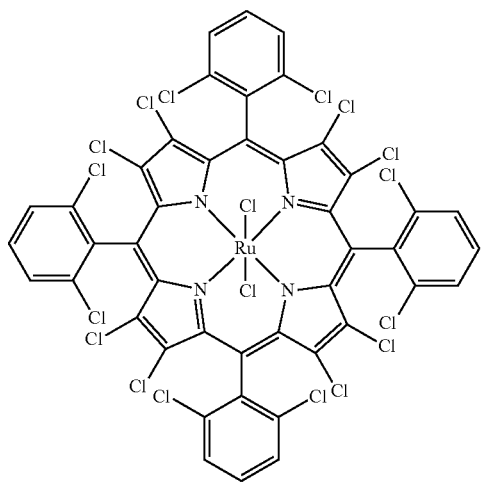

The Octachloro Octachloro free base (0.050 g), RuCl$_3$·6H$_2$O (0.100 g), and Decane (10 mL) were irradiated in a domestic microwave at low temperature. The microwave operated at 230 V at ca. 50 Hz and produced a maximum microwave power output of 750 W at a microwave frequency of 2450 MHz. The progress of the reaction was monitored by TLC. The irradiation was continued for 20 minutes. A small portion of reaction mixture was quenched in 10 ml water and extracted with 10 ml chloroform, to afford a purple solution. UV spectrum recorded after 20 min irradiation. Formation of 4 Octachloro Octachloro Ruthenium (III) Chloride was confirmed by UV-VIS spectra (λ ca. 420 nm). The Ru insertion occurs without destruction of the halogens on the pyrroles or the aromatic rings.

Preparation of Octachloro Octabromo Ruthenium (III) Chloride

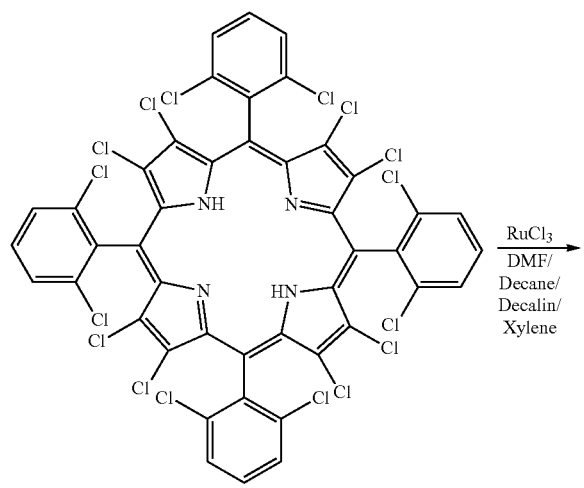

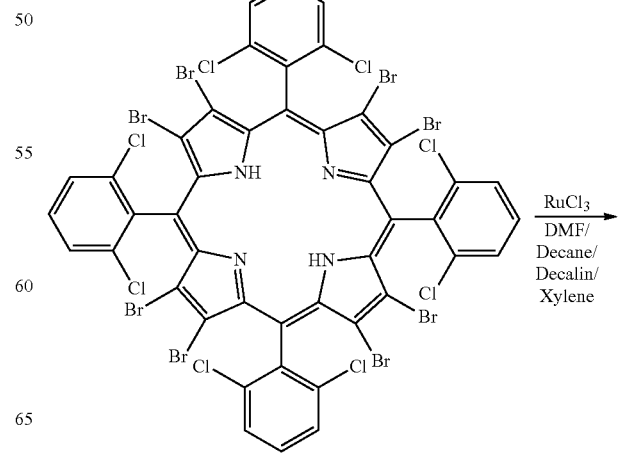

-continued

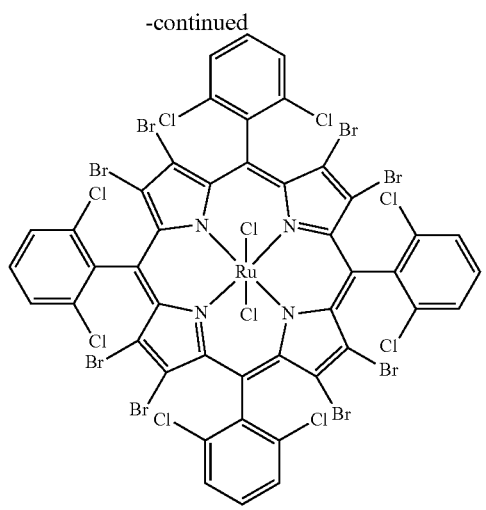

The Octachloro Octabromo free base (0.050 g), RuCl$_3$·6H2O (0.100 g), and decalin (10 mL) were irradiated in a domestic microwave at low temperature. The microwave operated at 230 V at ca. 50 Hz and produced a maximum microwave power output of 750 W at a microwave frequency of 2450 MHz. The progress of the reaction was monitored by TLC. The irradiation was continued for 20 minutes. A small portion of reaction mixture was quenched in 10 ml water and extracted with 10 ml chloroform, to afford a yellow solution. UV spectrum recorded after 20 min irradiation. Formation of 4 Octachloro Octabromo Ruthenium (III) Chloride was confirmed by UV-VIS spectra. The Ru insertion occurs without destruction of the halogens on the pyrroles or the aromatic rings.

Example 13. Ex Vivo Prediction of Drug-to-Drug Interaction

Metformin and Atorvastatin Mixture Microwave Protocol:
Metformin Hydrochloride (9.24 mg, 0.0719 mmol) in 1:0.25 mL acetonitrile:water was reacted with potassium carbonate (12.4 mg, 0.0895) and stirred at 40° C. for 30 minutes in a microwave tube. Atorvastatin API (40.0 mg, 0.07160 mmol) extracted using 80 mL 1:1 methanol:ethanol, filtered and concentrated in vacuo. The resulting solid taken up in 2:0.25 mL acetonitrile:water and transferred to microwave tube. Octabromo tetrakis(2,6-dichlorophenyl)porphyrin Fe(III)Cl (11.53 mg, 0.00716 mmol) then added, followed by sodium hypochlorite (176.8 uL, 0.3580 mmol). Reaction run in the microwave at 80° C. for 15 minutes (CC-03-145A).
(For reaction optimization, identical reactions were run at 80° C. for 30 minutes (CC-03-145B) and 80° C. for 45 minutes (CC-03-145C).)
Workup: Reaction concentrated, diluted with 10 mL chloroform. Washed 3×10 mL water. Washed 3×10 mL brine. Back-extracted aqueous layer with 10 mL chloroform. Organic layers combined and dried over MgSO4, filtered and concentrated in vacuo. Samples prepped for LC/MS/MS analysis crude.
HPLC-ESI-MS Parameters:
HPLC Parameters: Agilent 1200 HPLC, Binary pump, DAD, 100 tray autosampler
Column: Waters Xterra C18-MS, 4.6×5 cm, 3.5 um particle size, mobile phase A: water+0.1% formic acid, mobile phase B: ACN+0.1% formic acid, Flow rate: 1.0 mL/min,
Injection volume: 25 uL, Gradient 0 min 10% B hold for 1 minute, 10-80% B in 20 min. hold for 2 min.
Positive mode ESI parameters: Thermo TSQ Quantum Ultra, standard ESI source, Spray voltage: 4000V, Sheath gas pressure: 50 psi N2. Ion sweep gas pressure: 0.0 psi, Aux gas pressure: 0 psi, Capillary temperature: 325 C, Capillary offset: 35V, Tune lens offset: 117V, Skimmer offset: 0V, Collision Pressure: 1.5 mTorr Ar.
Representative metformin and atorvastatin metabolites following microwave reaction in the presence of Octabromo tetrakis(2,6-dichlorophenyl)porphyrin Fe(III)Cl are provided in Table 13.
Metformin and Pioglitazone Mixture Microwave Protocol:
Metformin Hydrochloride (10.0 mg, 0.07743 mmol) and Pioglitazone Hydrochloride (27.6 mg, 0.07743 mmol) in 2:0.25 mL acetonitrile:water were reacted with potassium carbonate (26.8 mg, 0.193575 mmol) and stirred at 40° C. for 30 minutes in a microwave tube. Octabromo tetrakis(2,6-dichlorophenyl)porphyrin Fe(III)Cl (12.47 mg, 0.00743 mmol) then added, followed by sodium hypochlorite (191.2 uL, 0.38715 mmol). Reaction run in the microwave at 80° C. for 30 minutes (CC-03-147A).
(For reaction optimization, identical reactions were run at 80° C. for 15 minutes (CC-03-147B) and 60° C. for 15 minutes (CC-03-147C).)
Workup: Reaction concentrated, diluted with 10 mL chloroform. Washed 3×10 mL water. Washed 3×10 mL brine. Back-extracted aqueous layer with 10 mL chloroform. Organic layers combined and dried over MgSO4, filtered and concentrated in vacuo. Samples prepped for LC/MS/MS analysis crude.
HPLC-ESI-MS Parameters:
HPLC Parameters: Agilent 1200 HPLC, Binary pump, DAD, 100 tray autosampler
Column: Waters Xterra C18-MS, 4.6×5 cm 3.5 um particle size, mobile phase A: water+0.1% formic acid, mobile phase B: ACN+0.1% formic acid, Flow rate: 1.0 mL/min,
Injection volume: 25 uL, Gradient 0 min 10% B hold for 1 minute, 10-80% B in 20 min. hold for 2 min.
Positive mode ESI parameters: Thermo TSQ Quantum Ultra, standard ESI source, Spray voltage: 4000V, Sheath gas pressure: 50 psi N2, Ion sweep gas pressure: 0.0 psi, Aux gas pressure: 0 psi, Capillary temperature: 325 C, Capillary offset: 35V, Tune lens offset: 117V, Skimmer offset: 0V, Collision Pressure: 1.5 mTorr Ar.
Metformin and Saxagliptin Mixture Microwave Protocol:
Metformin Hydrochloride (8.19 mg, 0.06341 mmol) in 1:0.25 mL acetonitrile:water was reacted with potassium carbonate (10.96 mg, 0.07926) and stirred at 40° C. for 30 minutes in a microwave tube. Saxagliptin API (20.0 mg, 0.06341 mmol) extracted using 40 mL 1:1 methanol:ethanol, filtered and concentrated in vacuo. The resulting solid taken up in 2:0.25 mL acetonitrile:water and transferred to microwave tube. Octabromo tetrakis(2,6-dichlorophenyl)porphyrin Fe(III)Cl (10.21 mg, 0.006341 mmol) then added, followed by sodium hypochlorite (156.6 uL, 0.3171 mmol). Reaction run in the microwave at 80° C. for 30 minutes (CC-03-149A).
(For reaction optimization, identical reactions were run at 80° C. for 15 minutes (CC-03-149B) and 60° C. for 15 minutes (CC-03-149C).)
Workup: Reaction concentrated, diluted with 10 mL chloroform. Washed 3×10 mL water. Washed 3×10 mL brine. Back-extracted aqueous layer with 10 mL chloroform. Organic layers combined and dried over MgSO4, filtered and concentrated in vacuo. Samples prepped for LC/MS/MS analysis crude.

HPLC-ESI-MS Parameters:
HPLC Parameters: Agilent 1200 HPLC, Binary pump, DAD, 100 tray autosampler
Column: Waters Xterra C18-MS, 4.6×5 cm 3.5 um particle size, mobile phase A: water+0.1% formic acid, mobile phase B: ACN+0.1% formic acid, Flow rate: 1.0 mL/min,
Injection volume: 25 uL, Gradient 0 min 10% B hold for 1 minute, 10-80% B in 20 min. hold for 2 min.
Positive mode ESI parameters: Thermo TSQ Quantum Ultra, standard ESI source, Spray voltage: 4000V, Sheath gas pressure: 50 psi N2, Ion sweep gas pressure: 0.0 psi, Aux gas pressure: 0 psi, Capillary temperature: 325 C, Capillary offset: 35V, Tune lens offset: 117V, Skimmer offset: 0V, Collision Pressure: 1.5 mTorr Ar.

Results

Representative metformin metabolites following microwave reaction in the presence of Octabromo tetrakis(2,6-dichlorophenyl)porphyrin Fe(III)Cl are provided in Table 13.

TABLE 13

Presence of Metformin metabolites:

| | Metformin | Atorvastatin | Pioglitazone | Saxagliptin |
|---|---|---|---|---|
| Metformin (MET) MW = 129.10 129.60→130.60 | rt = 0.51 | rt = 0.51 | rt = 0.51 | rt = 0.68 |
| Desmethyl-Metformin MW = 115.09 115.59→116.59 | rt = 0.59 | rt = 0.55 | rt = 0.59 | rt = 0.59 |
| Didesmethyl-Metformin MW = 101.07 101.57→102.57 | rt = 0.59 | Not Detected | rt = 0.64 | rt = 0.68 |
| N-Oxide Metformin MW = 145.01 145.60→146.60 | rt = 0.47 | Not Detected | Not Detected | Not Detected |
| Desmethyl N-oxide Metformin MW = 131.08 131.58→132.58 | rt = 2.11 | rt = 2.11 | rt = 2.07 | rt = 2.07 |

Representative atorvastatin metabolites following microwave reaction in the presence of Octabromo tetrakis(2,6-dichlorophenyl)porphyrin Fe(III)Cl are provided in Table 14.

TABLE 14

Presence of Atorvastatin metabolites:

| | Atorvastatin | Metformin |
|---|---|---|
| Atorvastatin Acid MW = 558.25 558.75→559.75 | rt = 13.10 | rt = 13.10 |
| Atorvastatin Lactone MW = 540.25 540.74→541.74 | rt = 7.31 | rt = 7.31 |
| o-Hydroxy ATR Acid MW = 574.25 574.75→575.75 | rt = 12.56 | rt = 12.60 |
| o-Hydroxy ATR Lactone MW = 556.24 556.74→557.74 | rt = 13.10 | rt = 13.10 |
| p-Hydroxy ATR Acid MW = 574.25 574.75→575.75 | rt = 13.04 | rt = 13.07 |

TABLE 14-continued

Presence of Atorvastatin metabolites:

| | Atorvastatin | Metformin |
|---|---|---|
| p-Hydroxy ATR Lactone MW = 556.24 556.74→557.74 | rt = 13.58 | rt = 13.24 |

Representative saxagliptin metabolites following microwave reaction in the presence of Octabromo tetrakis(2,6-dichlorophenyl)porphyrin Fe(III)Cl are provided in Table 15.

TABLE 15

Presence of Saxagliptin metabolites:

| | Saxagliptin | Metformin |
|---|---|---|
| Saxagliptin MW = 315.19 315.90→316.90 | rt = 3.24 | rt = 3.19 |
| Hydroxy-Saxagliptin MW = 331.19 331.90→316.90 | rt = 7.78 | Not Detected |

Representative pioglitazone metabolites following microwave reaction in the presence of Octabromo tetrakis(2,6-dichlorophenyl)porphyrin Fe(III)Cl are provided in Table 16.

TABLE 16

Presence of Pioglitazone metabolites:

| | Pioglitazone | Metformin |
|---|---|---|
| Pioglitazone MW = 356.12 356.60→357.60 | rt = 6.17 | rt = 6.15 |
| 2/9-Hydroxy Pioglitazone MW = 372.11 372.30→373.30 | rt = 7.55 | rt = 7.51 |
| 2/9-Carbonyl Pioglitazone MW = 370.10 370.60→371.60 | rt = 7.61 | rt = 7.54 |
| 2/9-Hydroxy Pioglitazone MW = 372.11 372.30→373.30 | rt = 8.57 | Not Detected |
| 2/9-Carbonyl Pioglitazone MW = 370.10 370.60→371.60 | rt = 8.81 | Not Detected |

Example 14

Furosemide API (12.5 mg, 0.0378 mmol) in DMSO (0.1 M) was added to octabromo tetrakis(2,6-dichlorophenyl) porphyrin Fe(III)Cl (0.6 mg, 0.000378 mmol), followed by imidazole (0.13 mg, 0.00189 mmol). Over a 1 hour period, 50% w/w hydrogen peroxide (6.44 uL, 0.1134 mg) was added dropwise. An additional amount of hydrogen peroxide was added after 2 hours. The reaction was monitored by LC and stopped after 24 hours.

A control reaction was run under the exact parameters as stated above, without the addition of imidazole as a co-catalyst.

Samples analyzed according to parameters in Example 1.

Figure 18A:
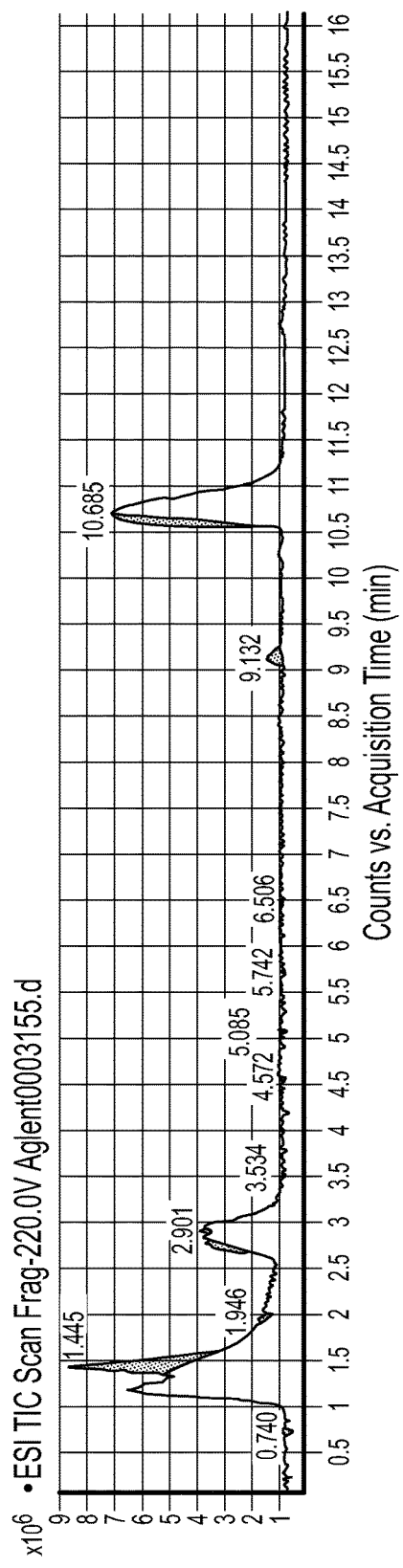
FIG. 18A-B are representative LC/MS-ESI chromatograms demonstrating the difference in furosemide metabolites produced when incorporating a nitrogen-containing co-catalyst in addition to the primary octabromo tetrakis(2,6-dichlorophenyl)porphyrin Fe(III)Cl catalyst, under conventional conditions, and when a co-catalyst is not employed.
Figure 18A:
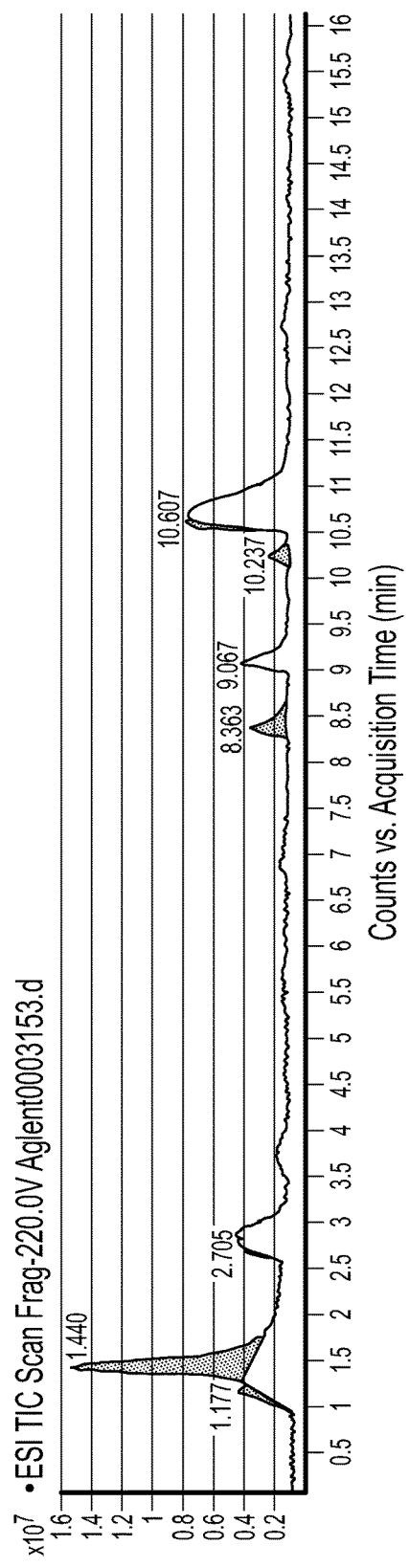
Figure 18B:
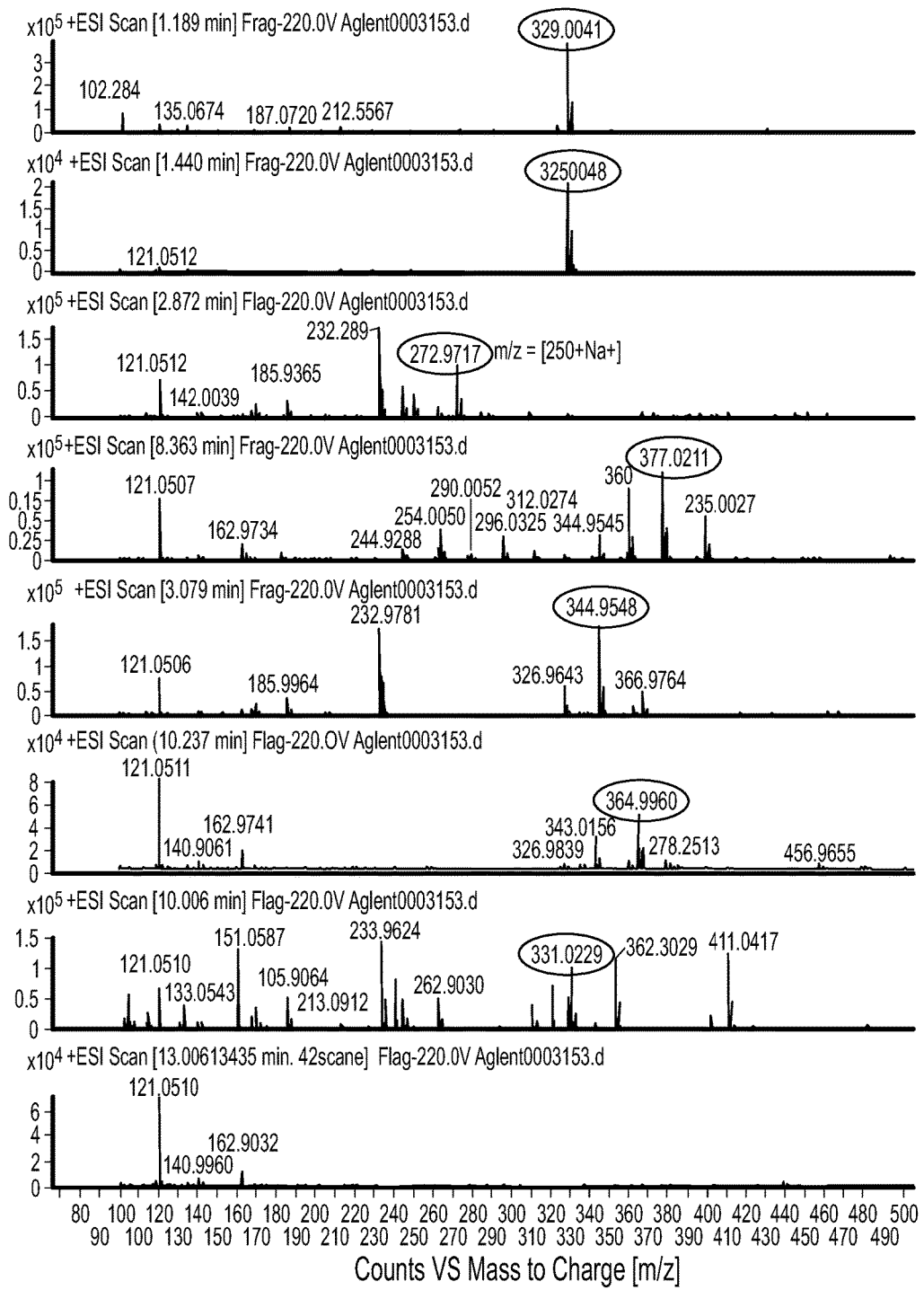

Identification of furosemide metabolites following conventional method in the presence of Octabromo tetrakis(2, 6-dichlorophenyl)porphyrin Fe(III)Cl are provided in Table 17 and FIG. 18A-B.

TABLE 17

Comparison of furosemide metabolites produced in the presence or absence of a co-catalyst.

| Spec. Reference | [M + H]: Respective Metabolite | MS MODE | Retention Time (min) | Imidazole Co-Catalyst | No Co-Catalyst |
|---|---|---|---|---|---|
| 1 | m/z 329.0011: FUR1 | ESI | 1.189 | Present | Present |
| 2 | m/z 329.0048: FUR2 | ESI | 1.440 | Present | Present |
| 3 | m/z 272.9717 [+Na⁺] FUR3 | ESI | 2.872 | Present | Present |
| 4 | m/z 377.0211: FUR4 | ESI | 8.363 | Present | Not observed |
| 5 | m/z 344.9948: FUR5 | ESI | 9.079 | Present | Not observed |
| 6 | m/z 364.9980: FUR6 | ESI | 10.237 | Present | Not observed |
| 7 | m/z 331.0228: Furosemide | ESI | 10.666 | N/A | N/A |

Furosemide Metabolite Structures:

| Compound | Structure |
|---|---|
| FUR1 Chemical Formula: $C_{12}H_9ClN_2O_5S$ Exact Mass: 327.99 | 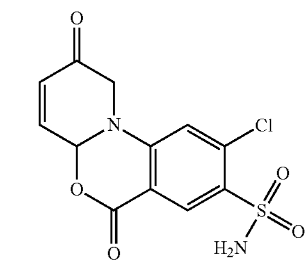 [SMILES: NS(=O)(=O)c1cc2c(cc1Cl)N1CC(=O)C=CC1OC2=O] |
| FUR2 Chemical Formula: $C_{12}H_9ClN_2O_5S$ Exact Mass: 327.99 | 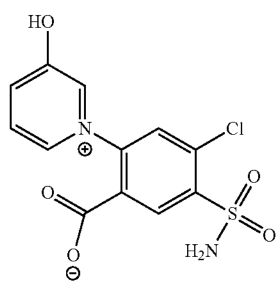 [SMILES: NS(=O)(=O)c1cc(C(=O)[O-])c(-[n+]2cccc(O)c2)cc1Cl] |
| FUR3 Chemical Formula: $C_7H_7ClN_2O_4S$ Exact Mass: 249.98 | 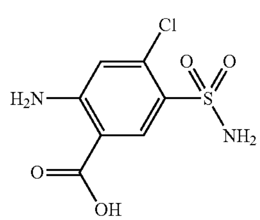 [SMILES: Nc1cc(Cl)c(S(N)(=O)=O)cc1C(=O)O] |
| FUR4 Chemical Formula: $C_{12}H_9ClN_2O_8S$ Exact Mass: 375.98 | 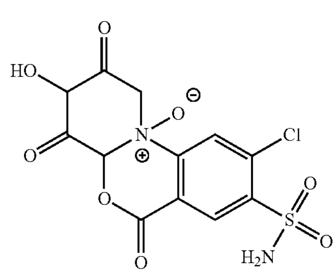 [SMILES: NS(=O)(=O)c1cc2c(cc1Cl)[N+]1(O)CC(=O)C(O)C(=O)C1OC2=O] |
| FUR5 Chemical Formula: $C_{12}H_9ClN_2O_6S$ Exact Mass: 343.99 | |
| FUR6 Chemical Formula: $C_{12}H_{13}ClN_2O_7S$ Exact Mass: 364.01 | |
| Furosemide Chemical Formula: $C_{12}H_{11}ClN_2O_5S$ Exact Mass: 330.01 | |

METABOLITE REFERENCES

GLM: Gurjar, M. K., et al. *Tetrahedron Letters*, 44, 4853-485 (2003).
SPI: Los, L., et al. *Drug Metabolism and Disposition*, 22(6), 904-908 (1994).
NIF: Snedden, W., et al. *Can. J. Physiol. Pharmacol.*, 64, 290-296 (1986).
AML: Stopher, D. A., et al. *Journal of Cardiovascular Pharmacology*, 12(Suppl. 7). S55-S59 (1988).
ATR: Narwal, et al. *Clin. Pharmacokinet.*, 49(10), 2010.
ATR: Park, J. E., et al. *Xenobiotica.* 38(9), 1240-1251 (2008).
ROS: Macwan. J. et al. *Anal Bioanal Chem.*, 402, 1217-1227 (2012).
SIM: Prueksaritanont, T., et al. *Drug Metabolism and Disposition*, 25(10), 1191-1199 (1997).
SAX: Fura, A. et al. *Drug Metabolism and Disposition*, 37, 1164-1171 (2009).
PIO: Tanis, S. P., et al. *Journal of Medicinal Chemistry*, 39(26), 5053-5063 (1996).
FUR: Williams, P., et al. *The journal of pharmacology and experimental therapeutics*, 322, 1208-1220 (2007).
Mansuy, D. C. R. *Chimie*, 10, 392-413 (2007).
Groves, J. T. *Nature*, 6, 89-91 (2014).
Yosca, T. H., et al. *Science*, 342, 825-829 (2013).

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. An ex vivo method for predicting an in vivo interaction between two or more pharmaceutically active compounds, the method comprising
contacting a first pharmaceutically active compound with (1) an oxidizing agent; (2) a catalyst selected from the group consisting of sterically hindered and electronically activated metallotetraphenylporphyrins, metallophthalocyanines and metallosalen complexes; and (3) a co-catalyst comprising a nitrogen- or sulfur-containing amino acid derivative in an aqueous solution under conditions suitable for the formation of oxidative metabolites, and identifying the oxidative metabolites formed, to produce a compound metabolite profile;
contacting, in combination, the first pharmaceutically active compound and at least one other pharmaceutically active compound with (1) an oxidizing agent; (2) a catalyst selected from the group consisting of sterically hindered and electronically activated metallotetraphenylporphyrins, metallophthalocyanines and metallosalen complexes; and (3) a co-catalyst comprising a nitrogen- or sulfur-containing amino acid derivative in an aqueous solution under conditions suitable for the formation of oxidative metabolites, and identifying the oxidative metabolites formed, to produce a combination metabolite profile;
comparing the compound metabolite profile with the combination metabolite profile; and
predicting an in vivo interaction between the pharmaceutically active compounds based on the presence of a difference between the compound metabolite profile as compared with the combination metabolite profile.

2. The method of claim 1, wherein the catalyst is a sterically hindered and electronically activated metallotetraphenylporphyrin of formula 1:

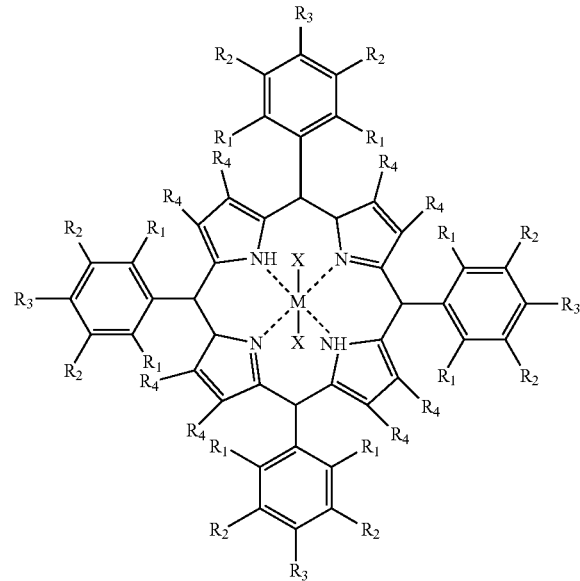

wherein $R_1$ is selected from the group consisting of Cl, Br, $CH_3$, $SO_3^-$, CN, $[N(R')_3]^+$, COOR', —OCONR'$_2$, —OMOM, CON-R', CONR'$_2$, CH=NR', $SO_2NR'_2$, $SO_2R$, CF and $NO_2$;

$R_2$ is selected from the group consisting of H, Cl, Br, $CH_3$, $SO_3^-$, CN, $[N(R')_3]^+$, COOR', —OCONR'$_2$, —OMOM, CON-R', CONR'$_2$, CH=NR', $SO_2NR'_2$, $SO_2R$, CF and $NO_2$;

$R_3$ is selected from the group consisting of H, Cl, Br, $CH_3$, $SO_3^-$, CN, $[N(R')_3]^+$, COOR', —OCONR'$_2$, —OMOM, CON-R', CONR'$_2$, CH=NR', $SO_2NR'_2$, $SO_2R$, CF and $NO_2$;

$R_4$ is selected from the group consisting of H, Cl, Br, $CH_3$, $SO_3^-$, CN, $[N(R')_3]^+$, COOR', —OCONR'$_2$, —OMOM, CON-R', CONR'$_2$, CH=NR', $SO_2NR'_2$, $SO_2R$, CF and $NO_2$;

R' is H or a C1-C6 alkyl; and

M is a transition metal, such as Fe, Zn, Co, Ni, Cu, Mn, Rh, Mg, Ru, Pt, and Pd; and wherein one or more axial ligands X selected from the group halogens (F, Cl, Br), OH, OCl, CO, $[N(R')_3]^+$, substituted or unsubstituted nitrogen- or sulfur-containing amino acid derivatives selected from the group consisting of imidazole, alkyl-substituted imidazoles, mercapto-substituted imidazoles, trifluoromethyl-substituted imidazoles, pyridine, alkyl-substituted pyridines, mercapto-substituted pyridines, trifluoromethyl-substituted pyridines, pyrimidine, alkyl-substituted pyrimidines, mercapto-substituted pyrimidines, trifluoromethyl-substituted pyrimidines, isoquinoline, alkyl-substituted isoquinolines, mercapto-substituted isoquinolines, trifluoromethyl-substituted isoquinolines, acridine, alkyl-substituted acridines, mercapto-substituted acridine, trifluoromethyl-substituted acridine, quinoline, benzoquinolines, alkyl-substituted quinolines, mercapto-substituted quinolines, trifluoromethyl-substituted quinolines, benzylmercaptan and thiophenold and/or a counter ion is included to maintain charge neutrality.

3. The method of claim 2, wherein $R_1$ is Cl, $R_2$ is H, $R_3$ is H, $R_4$ is Cl, M is Fe and X is Cl.

4. The method of claim 2, wherein $R_1$ is Cl, $R_2$ is H, $R_3$ is H, $R_4$ is Br, M is Fe and X is Cl.

5. The method of claim 2, wherein $R_1$ is Cl, $R_2$ is H and one $R_2$ is $SO_3Na$, $R_3$ is H, $R_4$ is Br, M is Fe and X is Cl.

6. The method of claim 2, wherein $R_1$ is Cl, $R_2$ is H, $R_3$ is H, $R_4$ is Cl or Br, M is Ru and X is Cl.

7. The method of claim 1, wherein the metallotetraphenylporphyrin is encapsulated in a polystyrene matrix.

8. The method of claim 1, wherein the metallotetraphenylporphyrin is immobilized to a polymeric resin solid support.

9. The method of claim 1, wherein the catalyst is a metallophthalocyanine compound of formula 2:

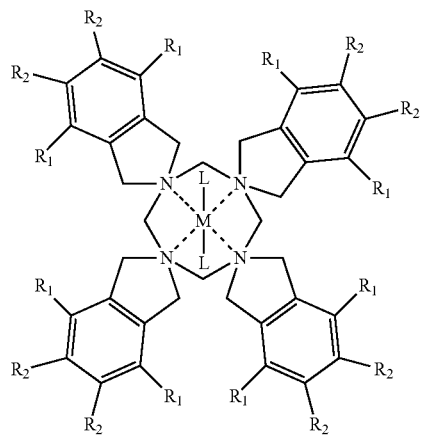

wherein R₁ is selected from the group consisting of Cl, Br, CH₃, SO₃⁻, CN, [N(R')₃]⁺, COOR', —OCONR'₂, —OMOM, CON-R', CONR'₂, CH=NR', SO₂NR'₂, SO₂R, CF and NO₂;

R₂ is selected from the group consisting of H, Cl, Br, CH₃, SO₃⁻, CN, [N(R')₃]⁺, COOR', —OCONR'₂, —OMOM, CON-R', CONR'₂, CH=NR', SO₂NR'₂, SO₂R, CF and NO₂;

R₃ is selected from the group consisting of H, Cl, Br, CH₃, SO₃⁻, CN, [N(R')₃]⁺, COOR', —OCONR'₂, —OMOM, CON-R', CONR'₂, CH=NR', SO₂NR'₂, SO₂R, CF and NO₂;

R₄ is selected from the group consisting of H, Cl, Br, CH₃, SO₃⁻, CN, [N(R')₃]⁺, COOR', —OCONR'₂, —OMOM, CON-R', CONR'₂, CH=NR', SO₂NR'₂, SO₂R, CF and NO₂;

wherein R' is H or a C1-C6 alkyl,

M is a transition metal, such as Fe, Zn, Co, Ni, Cu, Mn, Rh, Mg, Ru, Pt, and Pd; and wherein one or more axial ligands L selected from the group consisting of halogens (F, Cl, Br), OH, OCl, CO, [N(R')₃]⁺, and substituted or unsubstituted nitrogen- or sulfur-containing amino acid derivatives selected from the group consisting of imidazole, alkyl-substituted imidazoles, mercapto-substituted imidazoles, trifluoromethyl-substituted imidazoles, pyridine, alkyl-substituted pyridines, mercapto-substituted pyridines, trifluoromethyl-substituted pyridines, pyrimidine, alkyl-substituted pyrimidines, mercapto-substituted pyrimidines, trifluoromethyl-substituted pyrimidines, isoquinoline, alkyl-substituted isoquinolines, mercapto-substituted isoquinolines, trifluoromethyl-substituted isoquinolines, acridine, alkyl-substituted acridines, mercapto-substituted acridine, trifluoromethyl-substituted acridine, quinoline, benzoquinolines, alkyl-substituted quinolines, mercapto-substituted quinolines, trifluoromethyl-substituted quinolines, benzylmercaptan and thiophenol and/or a counter ion is included to maintain charge neutrality.

10. The method of claim 9, wherein R₁ and R₂ are Cl.

11. The method of claim 9, wherein R₁ and R₂ are H.

12. The method of claim 9, wherein the metallophthalocyanine is encapsulated in a polystyrene matrix.

13. The method of claim 9, wherein the metallophthalocyanine is immobilized to a polymeric resin solid support.

14. The method of claim 1, wherein the catalyst is a metallophthalocyanine compound of formula 2:

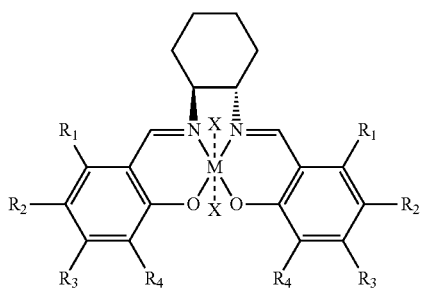

wherein R¹ is selected from the group consisting of Cl, Br, CH₃, SO₃⁻, CN, [N(R')₃]⁺, COOR', —OCONR'₂, —OMOM, CON-R', CONR'₂, CH=NR', SO₂NR'₂, SO₂R, CF and NO₂, R² is the same or different and is selected from the group consisting of H, Cl, Br, CH₃, —C(CH₃)₃, SO₃⁻, CN, [N(R')₃]⁺, COOR', —OCONR'₂, —OMOM, CON-R', CONR'₂, CH=NR', SO₂NR'2, SO₂R, CF and NO₂, R₃ is selected from the group consisting of H, Cl, Br, CH₃, SO₃⁻, CN, [N(R')₃]⁺, COOR', —OCONR'₂, —OMOM, CON-R', CONR'₂, CH=NR', SO₂NR'₂, SO₂R, CF and NO₂;

R₄ is selected from the group consisting of H, Cl, Br, CH₃, SO₃⁻, CN, [N(R')₃]⁺, COOR', —OCONR'₂, —OMOM, CON-R', CONR'₂, CH=NR', SO₂NR'₂, SO₂R, CF and NO₂;

wherein R' is H or a C1-C6 alkyl,

M is a transition metal, such as Fe, Zn, Co, Ni, Cu, Mn, Rh, Mg, Ru, Pt, and Pd, and wherein one or more axial ligands X selected from the group consisting of halogens (F, Cl, Br), OH, OCl, CO, [N(R')₃]⁺, and substituted or unsubstituted nitrogen- or sulfur-containing amino acid derivatives selected from the group consisting of imidazole, alkyl-substituted imidazoles, mercapto-substituted imidazoles, trifluoromethyl-substituted imidazoles, pyridine, alkyl-substituted pyridines, mercapto-substituted pyridines, trifluoromethyl-substituted pyridines, pyrimidine, alkyl-substituted pyrimidines, mercapto-substituted pyrimidines, trifluoromethyl-substituted pyrimidines, isoquinoline, alkyl-substituted isoquinolines, mercapto-substituted isoquinolines, trifluoromethyl-substituted isoquinolines, acridine, alkyl-substituted acridines, mercapto-substituted acridine, trifluoromethyl-substituted acridine, quinoline, benzoquinolines, alkyl-substituted quinolines, mercapto-substituted quinolines, trifluoromethyl-substituted quinolines, benzylmercaptan and thiophenol is included and/or a counter ion is included to maintain charge neutrality.

15. The method of claim 14, wherein the catalyst is present at less than 5% wt/wt catalyst/organic substrate.

16. The method of claim 15, wherein the catalyst is present at less than 1% wt/wt catalyst/organic substrate.

17. The method of claim 15, wherein the catalyst is present at less than 0.5% wt/wt catalyst/organic substrate.

18. The method of claim 1, wherein the catalyst is a homogenous catalyst.

19. The method of claim 1, wherein the catalyst is a heterogeneous catalyst.

20. The method of claim 1, wherein the oxidizing agent is selected from the group consisting of organic and inorganic peroxides, oxygen donor molecules, peracids, hypochlorites, ozone, potassium hydrogen persulfate, 2,6-dichloropyridine-N-oxide and molecular oxygen.

21. The method of claim 1, wherein the first pharmaceutically active compound and at least one other pharmaceutically active compound are selected from the group consisting of acetylcholine receptor stimulants and antagonists; adrenoreceptor-activated compounds, adrenoreceptor-blocking compounds, antihypertensive agents, vasodilators, cardiac glycosides, diuretics, histamine, serotonin, antihistamines, antihypertensives, polypeptides, antibiotics, anti-infective agents, antimicrobials, anticonvulsants, antidiabetic agents, antiemetics, steroids, sedatives, antiepileptic compounds, anesthetics, skeletal muscle relaxants, antidepressants, antipsychotics, analgesics, lithium, anticoagulants, cholinesterase inhibitors, procoagulants, HMG-CoA reductase inhibitors (statins), nonsteroidal anti-inflammatory agents, antimitotic agents, protease inhibitors, thyroid and antithyroid compounds, hypnotics, fibrinolytic agents, recombinant proteins, peptides, adrenocorticosteroids, gonadal hormones and inhibitors, immunomodulators, immunosuppressives, erectile dysfunction therapeutics, penicillins, cephalosporins, chloramphenicol, tetracyclines, polymyxins, antimyobacterial compounds, sulfonamides, narcotics, trimethoprim, antifungal agents, antiviral agents, non-steroidal anti-inflammatory compounds, anticancer agents, vaccines, antiprotozoal compounds, antacids, antiarythmics, and antihelminthic compounds.

22. The method of claim 1, wherein first pharmaceutically active compound and at least one other pharmaceutically active compound are selected from the lovastatin, amlodipine, atorvastatin, rosuvastatin, simvastatin, fluvastatin, pitavastatin, pravastatin, pioglitazone, lidocaine, odipipam, aminopyrine, metformin, glimepiride, spironolactone, nifedipine, furosemide, saxagliptin, clarithromycin, erythromycin, fluconazole, itraconazole, telithromycin, voriconazole, amiodarone, ticagrelor, imatinib, aprepitant, delavirdine, efavirenz, indinavir, nelfinavir, ritonavir, saquinavir, fluvoxamine, nefazodone, cyclosporine A, and quinine.

23. The method of claim 1, wherein the compound metabolite profile and the combination metabolite profiles are produced by NMR, $C^{13}$ NMR, MS, HRMS, IR, or UV spectroscopy.

24. The method of claim 1, further comprising isolating the resulting oxidative metabolites by HPLC, UPLC, Flash Chromatography or other preparative chromatographic techniques.

25. The method of claim 1, wherein the one or more pharmaceutically active compounds are selected from the lovastatin, amlodipine, atorvastatin, rosuvastatin, simvastatin, fluvastatin, pitavastatin, pravastatin, pioglitazone, lidocaine, odipipam, aminopyrine, metformin, glimepiride, spironolactone, nifedipine, furosemide, saxagliptin, clarithromycin, erythromycin, fluconazole, itraconazole, telithromycin, voriconazole, amiodarone, ticagrelor, imatinib, aprepitant, delavirdine, efavirenz, indinavir, nelfinavir, ritonavir, saquinavir, fluvoxamine, nefazodone, cyclosporine A, and quinine.

26. The method of claim 1, wherein the first pharmaceutically active compound is contacted with at least two other pharmaceutically active compounds to produce the combination metabolite profile.

27. The method of claim 1, wherein the first pharmaceutically active compound is contacted with at least three other pharmaceutically active compounds to produce the combination metabolite profile.

28. The method of claim 8, wherein the polymeric resin solid support comprises a polymeric resin selected from the group consisting of polyethylene, polystyrene, polycarbonate, polypropylene, polyimide, phenolic resin, epoxy resin, polycarbodiimide resin, polyvinyl chloride, polyvinylidene fluoride, polyethylene fluoride, polyimide, and acrylic resin.

29. The method of claim 1, wherein the nitrogen- or sulfur-containing amino acid derivative is selected from the group consisting of imidazole, alkyl-substituted imidazoles, mercapto-substituted imidazoles, trifluoromethyl-substituted imidazoles, pyridine, alkyl-substituted pyridines, mercapto-substituted pyridines, trifluoromethyl-substituted pyridines, pyrimidine, alkyl-substituted pyrimidines, mercapto-substituted pyrimidines, trifluoromethyl-substituted pyrimidines, isoquinoline, alkyl-substituted isoquinolines, mercapto-substituted isoquinolines, trifluoromethyl-substituted isoquinolines, acridine, alkyl-substituted acridines, mercapto-substituted acridine, trifluoromethyl-substituted acridine, quinoline, benzoquinolines, alkyl-substituted quinolines, mercapto-substituted quinolines, trifluoromethyl-substituted quinolines, benzylmercaptan and thiophenol.

30. The method of claim 1, further comprising further comprising contacting the solution containing the first pharmaceutically active compound with a phase-transfer agent in cases where the solution is a biphasic mixture.

31. The method of claim 30, wherein the phase transfer agent is selected from the group consisting of quaternary-ammonium salts, tetra-n-butylammonium bromide (TBAB), tricaprylylmethylammonium chloride, hexadecyltributyl-phosphonium bromide, tetrabutylphosphonium bromide, 18-crown-6, aliquat 336, benzyltriethylammonium chloride (TEBA), methyltrioctylammonium hydrogen sulfate (TOMAHS), cetylpyridinium chloride, tetrahexylammonium bromide, N-benzylcinchonidinium bromide, and N-benzylcinchoninium bromide.

32. An ex vivo method for predicting an in vivo interaction between two or more pharmaceutically active compounds, the method comprising
   contacting a first pharmaceutically active compound with an oxidizing agent and a catalyst selected from the group consisting of sterically hindered and electronically activated metallotetraphenylporphyrins, metallophthalocyanines and metallosalen complexes in an aqueous solution under conditions suitable for the formation of oxidative metabolites, and identifying the oxidative metabolites formed, to produce a compound metabolite profile;
   contacting, in combination, the first pharmaceutically active compound and at least one other pharmaceutically active compound with an oxidizing agent and a catalyst selected from the group consisting of sterically hindered and electronically activated metallotetraphenylporphyrins, metallophthalocyanines and metallosalen complexes in an aqueous solution under conditions suitable for the formation of oxidative metabolites, and identifying the oxidative metabolites formed, to produce a combination metabolite profile;
   comparing the compound metabolite profile with the combination metabolite profile; and
   predicting an in vivo interaction between the pharmaceutically active compounds based on the presence of a difference between the compound metabolite profile as compared with the combination metabolite profile,
   wherein the catalyst comprises one or more axial ligands X selected from the group halogens (F, Cl, Br), OH, OCl, CO, [N(R')$_3$]+, substituted or unsubstituted nitrogen- or sulfur-containing amino acid derivatives selected from the group consisting of imidazole, alkyl-substituted imidazoles, mercapto-substituted imidazoles, trifluoromethyl-substituted imidazoles, pyridine, alkyl-substituted pyridines, mercapto-substituted pyridines, trifluoromethyl-substituted pyridines, pyrimidine, alkyl-substituted pyrimidines, mercapto-substituted pyrimidines, trifluoromethyl-substituted pyrimidines, isoquinoline, alkyl-substituted isoquinolines, mercapto-substituted isoquinolines, trifluoromethyl-substituted isoquinolines, acridine, alkyl-substituted acridines, mercapto-substituted acridine, trifluoromethyl-substituted acridine, quinoline, benzoquinolines, alkyl-substituted quinolines, mercapto-substituted quinolines, trifluoromethyl-substituted quinolines, benzylmercaptan and thiophenold.

* * * * *

UNITED STATES PATENT AND TRADEMARK OFFICE
CERTIFICATE OF CORRECTION

PATENT NO. : 10,265,692 B2  
APPLICATION NO. : 15/101088  
DATED : April 23, 2019  
INVENTOR(S) : Mukund Chorghade and Chiara Chapman Page 1 of 1

It is certified that error appears in the above-identified patent and that said Letters Patent is hereby corrected as shown below:

In the Claims

Column 62, Line 31-32, Claim 2, delete "thiophenold" and insert -- thiophenol --

Column 64, Line 2, Claim 14, delete "$SO_2NR'2$," and insert -- $SO_2NR'_2$, --

Column 65, Line 5-6, Claim 21, delete "antiarythmics," and insert -- antiarrhythmics, --

Column 65, Line 49, Claim 28, delete "polyimide," and insert -- polyamide, --

Column 66, Line 62, Claim 32, delete "thiophenold." and insert -- thiophenol. --

Signed and Sealed this  
Second Day of July, 2019

Andrei Iancu  
*Director of the United States Patent and Trademark Office*